United States Patent
Valente et al.

(10) Patent No.: US 9,682,994 B2
(45) Date of Patent: Jun. 20, 2017

(54) INHIBITORS OF RETROVIRAL REPLICATION

(71) Applicants: Susana Valente, Stuart, FL (US); Phil S. Baran, San Diego, CA (US)

(72) Inventors: Susana Valente, Stuart, FL (US); Phil S. Baran, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 14/755,426

(22) Filed: Jun. 30, 2015

(65) Prior Publication Data

US 2016/0016971 A1 Jan. 21, 2016

Related U.S. Application Data

(63) Continuation of application No. 13/978,672, filed as application No. PCT/US2012/020741 on Jan. 10, 2012, now abandoned.

(60) Provisional application No. 61/431,198, filed on Jan. 10, 2011.

(51) Int. Cl.

| | | |
|---|---|---|
| A61K 31/47 | (2006.01) |
| C07D 495/04 | (2006.01) |
| A61K 31/4725 | (2006.01) |
| A61K 31/58 | (2006.01) |
| A61K 31/4709 | (2006.01) |
| A61K 45/06 | (2006.01) |
| C07D 405/04 | (2006.01) |

(52) U.S. Cl.
CPC ........ *C07D 495/04* (2013.01); *A61K 31/4709* (2013.01); *A61K 31/4725* (2013.01); *A61K 31/58* (2013.01); *A61K 45/06* (2013.01); *C07D 405/04* (2013.01)

(58) Field of Classification Search
CPC .................................................. A61K 31/4725
USPC .......................................................... 514/307
See application file for complete search history.

(56) References Cited

U.S. PATENT DOCUMENTS

2008/0207677 A1* 8/2008 Muller ................ C07D 471/04
514/300

FOREIGN PATENT DOCUMENTS

WO WO 2009/137335 A1 * 11/2009

OTHER PUBLICATIONS

Cee et al. "Cortistatin A is a high-affinity ligand of protein kinase ROCK, CDK8, and CDK11", Angew. Chem. Int. Ed. 2009, vol. 48, pp. 8952-8957.*
Yu et al. "Cyclin T1-dependent genes in activated CD4+ T and macrophage cell lines appear enriched in HIV cofactors," PLoS One (www.plosone.org), 2008, vol. 3, No. 9, e3146.*
Sato et al. "inhibition of human immunodeficiency virus type 1 replication by a bioavailable serine/threonine kinase inhibitor, fasudil hydrochloride," AIDS Research and human retroviruses, 1998, vol. 14, No. 4, pp. 293-298.*

* cited by examiner

*Primary Examiner* — Shengjun Wang
(74) *Attorney, Agent, or Firm* — Hugh Wang; Thomas Fitting

(57) ABSTRACT

Methods for preventing or treating retroviral infection, such as human immunodeficiency virus, in vivo utilize transcriptional inhibitory compounds. These include cortistatin A and analogs of the cortistatin family.

14 Claims, 23 Drawing Sheets

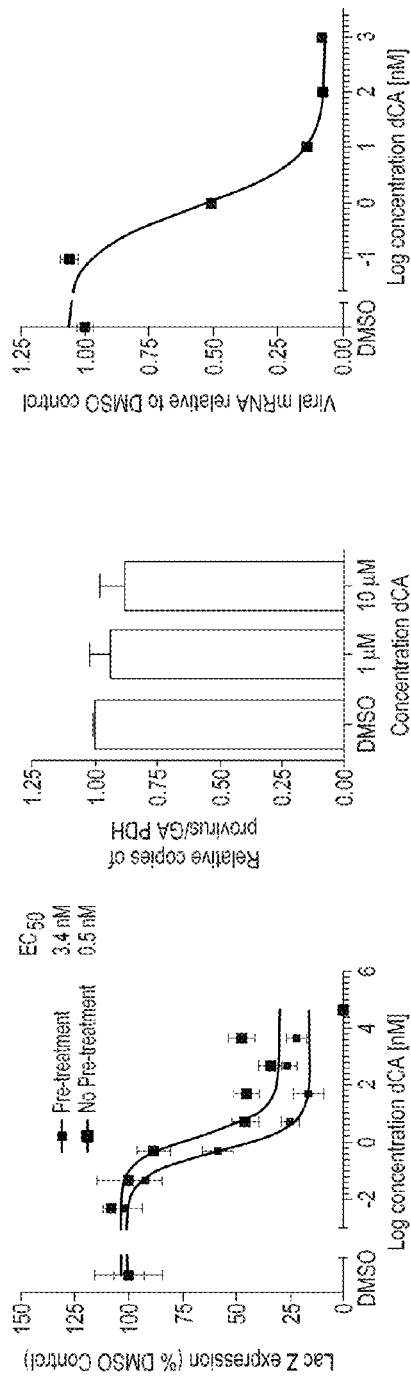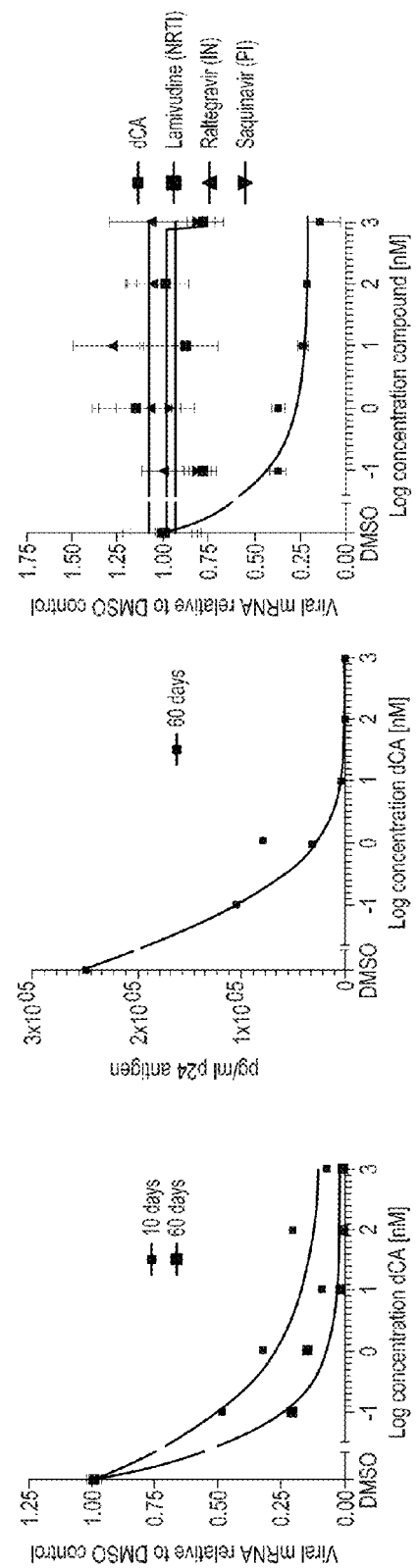

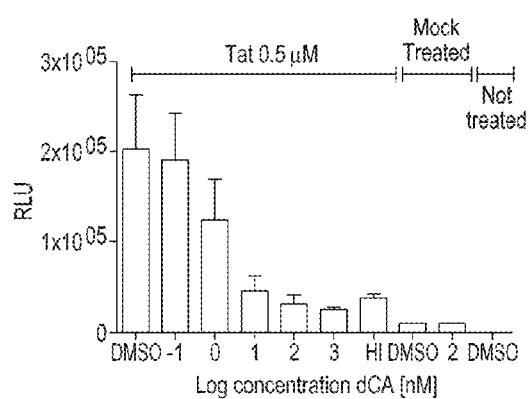
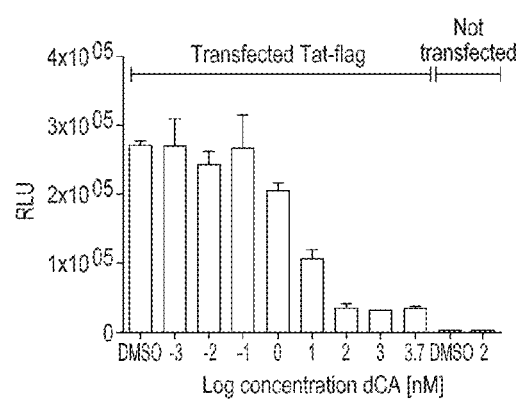
FIG. 2A
FIG. 2B
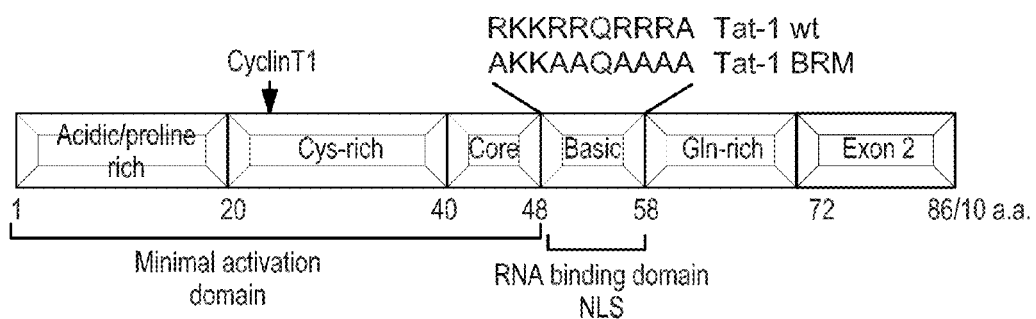
FIG. 2C

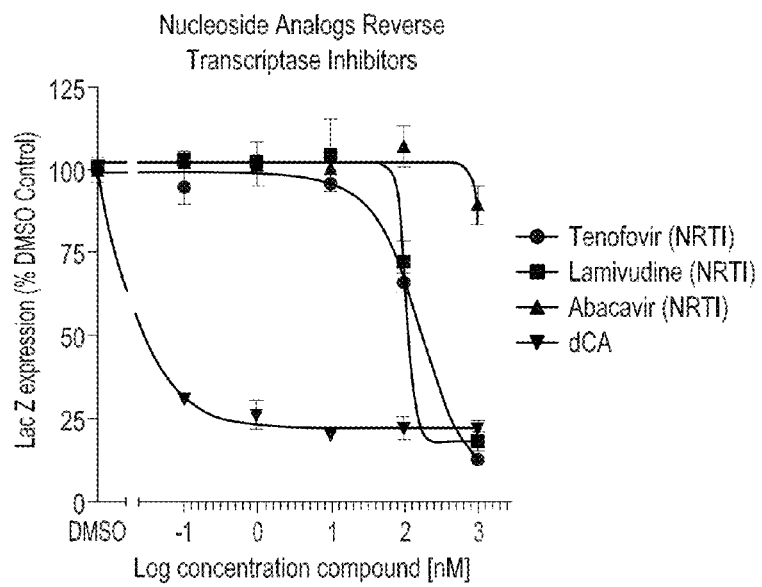
FIG. 5C
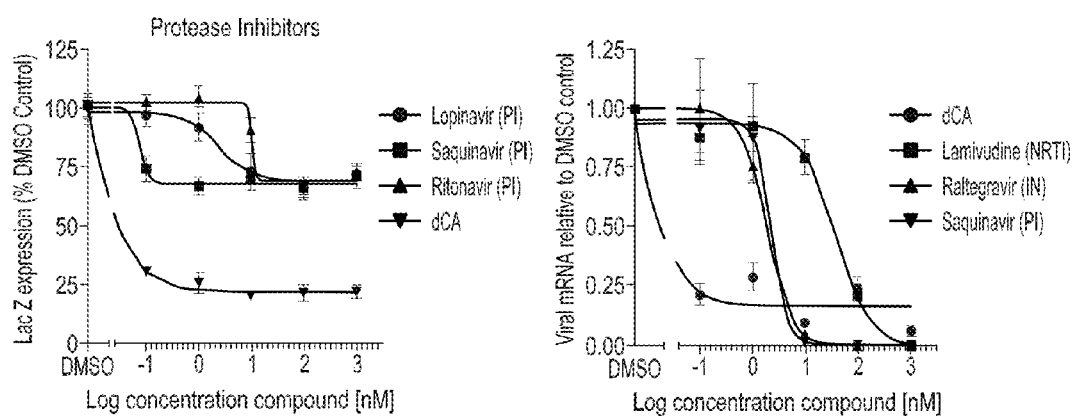
FIG. 5D
FIG. 5E

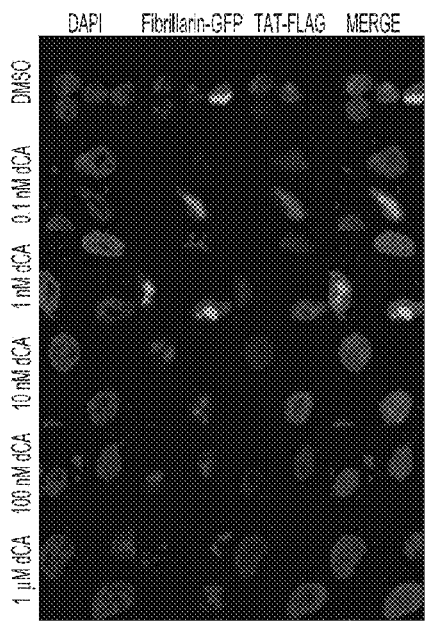
FIG. 11A
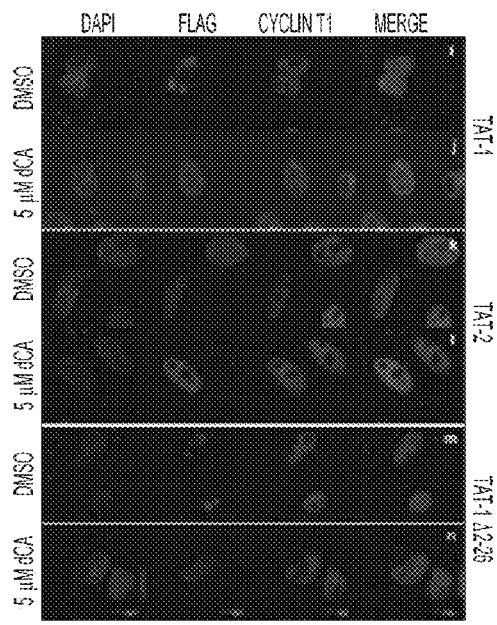
FIG. 11C
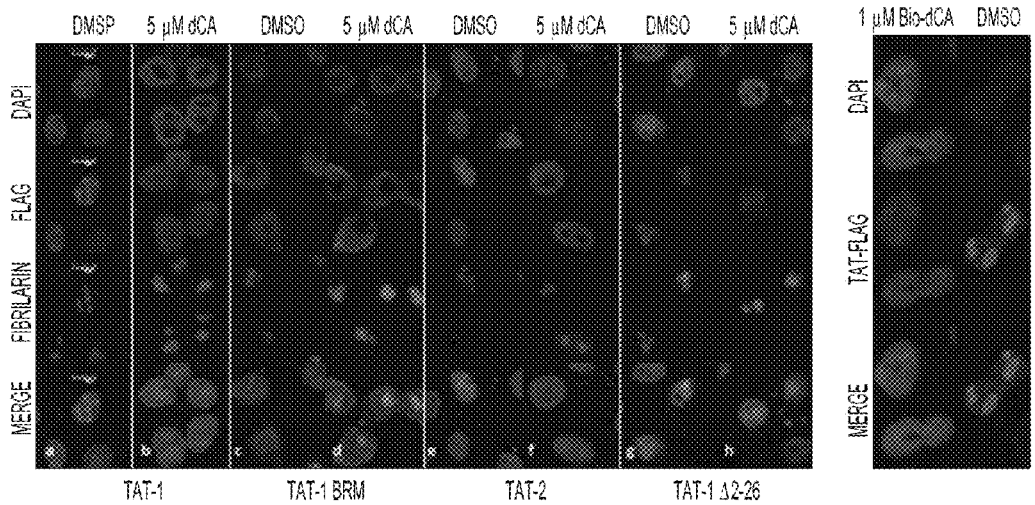
FIG. 11B
FIG. 11D

SEQUENCE LISTING

```
<160> NUMBER OF SEQ ID NOS: 22

<210> SEQ ID NO 1
<211> LENGTH: 23
<212> TYPE: DNA
<213> ORGANISM: Artificial sequence
<220> FEATURE:
<223> OTHER INFORMATION: Synthetic sequence

<400> SEQUENCE: 1
caacagcctc aagatcatca gca                                          23

<210> SEQ ID NO 2
<211> LENGTH: 26
<212> TYPE: DNA
<213> ORGANISM: Artificial sequence
<220> FEATURE:
<223> OTHER INFORMATION: Synthetic sequence

<400> SEQUENCE: 2
agggatgacc ttgcccacag ccttgg                                       26

<210> SEQ ID NO 3
<211> LENGTH: 25
<212> TYPE: DNA
<213> ORGANISM: Artificial sequence
<220> FEATURE:
<223> OTHER INFORMATION: Synthetic sequence

<400> SEQUENCE: 3
gacaagagat ccttgatctg tggat                                        25

<210> SEQ ID NO 4
<211> LENGTH: 24
```

<212> TYPE: DNA
<213> ORGANISM: Artificial sequence
<220> FEATURE:
<223> OTHER INFORMATION: Synthetic sequence

<400> SEQUENCE: 4
ccttgtagaa agctcgatgt cagc                                          24

<210> SEQ ID NO 5
<211> LENGTH: 21
<212> TYPE: DNA
<213> ORGANISM: Artificial sequence
<220> FEATURE:
<223> OTHER INFORMATION: Synthetic sequence

<400> SEQUENCE: 5
ggctaactag ggaacccact g                                             21

<210> SEQ ID NO 6
<211> LENGTH: 24
<212> TYPE: DNA
<213> ORGANISM: Artificial sequence
<220> FEATURE:
<223> OTHER INFORMATION: Synthetic sequence

<400> SEQUENCE: 6
ctgctagaga ttttccacac tgac                                          24

<210> SEQ ID NO 7
<211> LENGTH: 35
<212> TYPE: DNA
<213> ORGANISM: Artificial sequence
<220> FEATURE:
<223> OTHER INFORMATION: Synthetic sequence

<400> SEQUENCE: 7
tgtatccttt agcttccctc agatcactct ttggc                              35

<210> SEQ ID NO 8
<211> LENGTH: 19
<212> TYPE: DNA
<213> ORGANISM: Artificial sequence
<220> FEATURE:
<223> OTHER INFORMATION: Synthetic sequence

<400> SEQUENCE: 8 cctttccat ttctgtaca                                                 19

<210> SEQ ID NO 9
<211> LENGTH: 22
<212> TYPE: DNA
<213> ORGANISM: Artificial sequence
<220> FEATURE:
<223> OTHER INFORMATION: Synthetic sequence

<400> SEQUENCE: 9
acttacgggg atacttgggc ag                                            22

<210> SEQ ID NO 10
<211> LENGTH: 24
<212> TYPE: DNA
<213> ORGANISM: Artificial sequence
<220> FEATURE:
<223> OTHER INFORMATION: Synthetic sequence

<400> SEQUENCE: 10
ctccatttct tgctctcctc tgtc                                              24

<210> SEQ ID NO 11
<211> LENGTH: 34
<212> TYPE: DNA
<213> ORGANISM: Artificial sequence
<220> FEATURE:
<223> OTHER INFORMATION: Synthetic sequence

<400> SEQUENCE: 11
gaaaaacatg gagcaatcac aagtagcaat acag                                   34

<210> SEQ ID NO 12
<211> LENGTH: 35
<212> TYPE: DNA
<213> ORGANISM: Artificial sequence
<220> FEATURE:
<223> OTHER INFORMATION: Synthetic sequence

<400> SEQUENCE: 12
cagatcaagg atatcttgtc ttctttggga gtgaa                                  35

<210> SEQ ID NO 13
<211> LENGTH: 20
<212> TYPE: DNA
<213> ORGANISM: Artificial sequence
<220> FEATURE:
<223> OTHER INFORMATION: Synthetic sequence

<400> SEQUENCE: 13
atggttgcca ctggggatct                                                   20

<210> SEQ ID NO 14
<211> LENGTH: 20
<212> TYPE: DNA
<213> ORGANISM: Artificial sequence
<220> FEATURE:
<223> OTHER INFORMATION: Synthetic sequence

<400> SEQUENCE: 14
tgccaaagcc tagggaaga                                                    20

<210> SEQ ID NO 15
<211> LENGTH: 21
<212> TYPE: DNA
<213> ORGANISM: Artificial sequence
<220> FEATURE:
<223> OTHER INFORMATION: Synthetic sequence

<400> SEQUENCE: 15
ggaggtggcc tagggctgct c                                                 21

<210> SEQ ID NO 16
<211> LENGTH: 19
<212> TYPE: DNA
<213> ORGANISM: Artificial sequence
<220> FEATURE:
<223> OTHER INFORMATION: Synthetic sequence

<400> SEQUENCE: 16
ggtggaatca tattggaac                                                    19

<210> SEQ ID NO 17

```
<211> LENGTH: 42
<212> TYPE: DNA
<213> ORGANISM: Artificial sequence
<220> FEATURE:
<223> OTHER INFORMATION: Synthetic sequence

<400> SEQUENCE: 17
atgccacgta agcgaaactc tggctaacta gggaacccac tg        42

<210> SEQ ID NO 18
<211> LENGTH: 18
<212> TYPE: DNA
<213> ORGANISM: Artificial sequence
<220> FEATURE:
<223> OTHER INFORMATION: Synthetic sequence

<400> SEQUENCE: 18
agctccctgc ttgcccat                                   18

<210> SEQ ID NO 19
<211> LENGTH: 18
<212> TYPE: DNA
<213> ORGANISM: Artificial sequence
<220> FEATURE:
<223> OTHER INFORMATION: Synthetic sequence

<400> SEQUENCE: 19
atgccacgta agcgaaac                                   18

<210> SEQ ID NO 20
<211> LENGTH: 25
<212> TYPE: DNA
<213> ORGANISM: Artificial sequence
<220> FEATURE:
<223> OTHER INFORMATION: Synthetic sequence

<400> SEQUENCE: 20
gctagagatt ttccacactg actaa                           25

<210> SEQ ID NO 21
<211> LENGTH: 27
<212> TYPE: DNA
<213> ORGANISM: Artificial sequence
<220> FEATURE:
<223> OTHER INFORMATION: Synthetic sequence

<400> SEQUENCE: 21
cacaacagac gggcacacac tacttga                         27

<210> SEQ ID NO 22
<211> LENGTH: 25
<212> TYPE: DNA
<213> ORGANISM: Artificial sequence
<220> FEATURE:
<223> OTHER INFORMATION: Synthetic sequence

<400> SEQUENCE: 22
cactcaaggc aagctttatt gaggc                           25
```

INHIBITORS OF RETROVIRAL REPLICATION

CROSS-REFERENCE TO RELATED APPLICATIONS

The present application is a continuation of U.S. patent application Ser. No. 13/978,672 (filed Aug. 20, 2013), which is a §371 U.S. national phase filing of PCT International Patent Application No. PCT/US2012/020741 (filed Jan. 10, 2012), which claims the benefit of priority to U.S. Provisional Patent Application No. 61/431,198 (filed Jan. 10, 2011). The disclosure of each of the aforementioned priority applications is incorporated herein by reference in its entirety and for all purposes.

STATEMENT OF GOVERNMENT SUPPORT

This invention was made with government support under AI077353 awarded by the National Institutes of Health. The government has certain rights in the invention.

FIELD OF THE INVENTION

Embodiments of the invention comprise methods for preventing or treating retroviral infection, such as human immunodeficiency virus (HIV), human T-cell leukemia virus (HTLV). Further embodiments comprise compounds which modulate Tat-TAR interactions, the functions or activities of Trans-Activator of Transcription (Tat) or Transactivation Responsive elements (TAR), molecules associated with Trans-Activator of Transcription (Tat) or Transactivation Responsive element (TAR).

BACKGROUND

Although treatment with antiretroviral drugs (ARVs) has extended the quality and expectancy of life for people infected with human immunodeficiency virus (HIV), they have been unsuccessful in curing HIV infection. Highly active antiretroviral therapy (HAART) is based on triple or quadruple combinations of ARVs, however while reducing HIV to very low levels, this treatment fails to eliminate the infection completely (Clavel F. & Hance A. J. (2004) *N Engl J Med* 350, 1023-1035; Arhel N. & Kirchhoff F. (2010) *Biochim Biophys Acta* 1802, 313-321). Ultrasensitive assays revealed that HIV persists in latently and productively infected CD4$^+$ T cells in the peripheral blood of individuals receiving HAART who have maintained undetectable plasma viremia for prolonged periods of time (Chun T W, et al. (2005) *J Clin Invest* 115, 3250-3255; Yukl S, et al. (2010) 17$^{th}$ *Conference on Retroviruses and Opportunistic Infections*, San Francisco; Palmer S, et al. (2008) *Proc Natl Acad Sci USA* 105, 3879-3884). Residual viremia is not affected by the addition of an integrase or a fusion inhibitor to a stable HAART regimen, suggesting that it originates from long-lived stable reservoirs that contain an integrated provirus that continuously produces viral particles despite HAART. Since viral production from these cellular reservoirs results from the continuous transcription of an integrated viral genome, they are not affected by NRTI, NNRTI, PIs, INIs or FIs.

SUMMARY

This Summary is provided to present a summary of the invention to briefly indicate the nature and substance of the invention. It is submitted with the understanding that it will not be used to interpret or limit the scope or meaning of the claims.

Embodiments are directed to pharmaceutical compositions comprising anti-Tat drugs and anti-Tat drug candidates.

In other preferred embodiments, methods of preventing a viral infection or treating patients suffering from a viral infection, such as for example, human immunodeficiency virus (HIV) are provided.

In one embodiment, a method of preventing viral infection or treating a viral infection in a patient, comprises administering to the patient a therapeutically effective amount of an inhibitor of retroviral transcription wherein the inhibitor inhibits retroviral transcription as compared to a control. In one embodiment, the retrovirus is a human immunodeficiency virus (HIV). In another embodiment, the retrovirus is a human T-cell leukemia virus (HTLV). However, any retrovirus is contemplated.

In preferred embodiments, the inhibitor of retroviral transcription inhibits function or activity of a Trans-Activator of Transcription (Tat), a molecule associated with Trans-Activator of Transcription (Tat), a molecule associated with Transactivation Responsive element (TAR) a Transactivation Responsive element (TAR) and/or interaction between a Trans-Activator of Transcription (Tat) and a Transactivation Responsive element (TAR), DNA-PK or combinations thereof. Preferably, the inhibitor of retroviral transcription comprises: cortistatins, cortistatin derivatives, analogs, substituted cortistatins or salts thereof. An example of a cortistatin is cortistatin A. An example of a cortistatin analog is didehydro-Cortistatin A (dCA).

Other aspects are described infra.

BRIEF DESCRIPTION OF THE DRAWINGS

FIGS. 1A-1H show the structure and activity of dCA on HIV-1 expression.

FIG. 1A: Structure of Cortistatin A and of its analog didehydro-Cortistatin A (dCA).

FIG. 1B: Activity of dCA on acute replication of HIV-1 at three different MOIs. HeLa-CD4 cells were plated at $1 \times 10^4$ cells per well of a 96-well plate, and 24 h later the indicated dilutions of HIV-1 pNL4-3 were added to the cells in the presence of dCA or DMSO. Forty-eight hours post infection a quantitative chlorophenol red-β-D-galactopyranoside (CPRG) assay was performed.

FIG. 1C: Effect of pre-treating cells with dCA on acute HIV-1 replication. HeLa-CD4 cells were either treated or not with increasing concentrations of dCA. Twenty-four hours later HIV-1 pNL4-3 was added to the cells of both experiment sets (MOI>>10) in the presence of testing compound or DMSO control. CPRG assay performed 48 h later.

FIG. 1D: dCA does not block HIV-1 proviral integration into host cells. HeLa-CD4 cells were infected with pNL4-3 (MOI>>1) in the presence of dCA. Total DNA was extracted 24 hours later and integrated provirus was determined by quantitative PCR (qPCR).

FIG. 1E: Analysis of viral mRNA expression. Total RNA was extracted three days after acute infection with pNL43 (MOI>>1) in the presence of dCA. First-strand cDNA was synthesized with random primers and target DNA was quantified by qPCR using primers recognizing the env and LTR regions. Results were normalized as copies of viral mRNA per copy of GAPDH mRNA. The arbitrary value of 1 was assigned to the amount of viral mRNA generated in the absence of dCA. RNA samples not reverse transcribed were used as negative control. Error bars represent standard deviations.

FIG. 1F: Viral mRNA expression levels upon dCA treatment of chronically infected cells. HeLa-CD4 cells chronically infected with pNL4-3 were treated with dCA for 10 or 60 days, total RNA was extracted, reverse transcribed using random primers, and the quantification of viral cDNA was performed as in FIG. 1E.

FIG. 1G: p24 antigen quantification. Viral supernatants recovered from cells described in FIG. 1B, grown for 60 days, were assayed for their p24 antigen content using a sandwich ELISA kit. Error bars represent standard deviations.

FIG. 1H: Viral RNA levels upon treatment of CEM SS cells with dCA and known antiviral drugs. CEM SS cells chronically infected with pNL4-3 were treated with the indicated compounds for 7 days. Quantification of viral RNA was performed as in FIG. 1E.

FIGS. 2A-2G show that dCA binds to Tat and inhibits Tat transactivation of the HIV-1 LTR.

FIG. 2A: dCA prevents transactivation of the HIV-1 promoter by recombinant Tat. HeLa-CD4-LTR-Luc cells were treated with 0.5 µM recombinant Tat protein with increasing concentrations of dCA. Chloroquine 100 µM was added to increase Tat uptake was added to all points except untreated wells. Luciferase activity was measured 24 h later using the Luciferase Assay System (Promega). Luciferase activity per protein concentration of each sample is shown as relative light units (RLU). HI: Heat Inactivated.

FIG. 2B: HeLa-LTR-Luc cells were transfected with 2 µg of a construct expressing Tat-flag driven by the thymidine kinase (TK) promoter. Twenty-four hours later cells were split and treated or not with dCA at the indicated concentrations. Forty hours later RLU determined as in FIG. 2A. RLU at 0 nM dCA set as 100% activation.

FIG. 2C: Schematic diagram of the HIV-1 Tat protein. Indicated are known domains involved in either transactivation or interaction with host factors. Depicted above is the amino acid sequence of the wild-type basic domain or a mutated form that is deficient in binding to the TAR loop.

FIG. 2D: Structure of biotinylated cortistatin A.

FIG. 2E: dCA binds to TAR but not to TAR non-binding mutant of Tat. HEK293T cells were transfected with flag-tagged Tat 101 a.a. (Tat-F-101-wt), a shorter Tat version with 86 a.a. (Tat-F-86-wt), Tat 86 a.a. mutated in the basic domain (Tat-F-BRM), flag-tagged CDK11 (CDK11-F), flag-tagged 9G8 (9G8-F) and empty vector control. Forty hours later, protein extracts were incubated with DYNABEADS MYONE™ Streptavidin T1 coated with either Biotin or Bio-dCA. Pulled-down proteins were revealed by Western blotting with the indicated antibodies.

FIG. 2F: dCA interacts with purified recombinant Tat protein. Recombinant Tat protein was incubated with Bio-dCA streptavidin-coated beads in the presence or absence of an excess of non-biotinylated dCA (represented as molar equivalent [eq.] of Bio-dCA). Raltegravir and recombinant GST-9G8 were used as a negative control competitor or as negative protein-binding control, respectively. Pulled-down proteins were revealed by Western blot with anti-Tat and anti-GST antibodies.

FIG. 2G: dCA alters Tat-Flag cellular localization. Confocal microscopy analysis of the sub-cellular localization of transfected Tat-F-86-F and Tat-F-86-BRM and where indicated treated (24 h) or not with dCA. Flag epitope-tagged Tat was recognized with anti-flag and AlexaFluor 568 anti-IgG. Transfections were performed in HeLa-CD4 cells. Magnification 300×.

FIG. 3A: Schematic representation of the HIV genome and localization of primers.

FIG. 3B: HIV-1 elongation from HIV-1 promoter measured by qPCR. Left panel: Total RNA was recovered from chronically infected HeLa cells treated with increasing amounts of dCA for 60 days, reverse transcribed using random primers and viral cDNA was measured by relative qRT-PCR using the indicated primers located either at 100 bp, 5.3 kb or 8.5 kb downstream from the transcript start site. All messages were normalized relative to GAPDH mRNA. The 100% value was arbitrarily assigned to the amounts of viral mRNA generated in the absence of compound, measured at 100 bp from start site. Right panel: Plotting of data obtained in left panel, setting each data point obtained with the 100 bp primer set at 100% and comparing to results obtained with 5.3 kb primer set.

FIG. 3C: ChIP assay of the HIV promoter. HeLa-CD4 cells chronically infected with pNL4-3 were treated with dCA for 4 days and flavopiridol (Flav) for 6 h followed by protein-DNA crosslinking. Lysates were sonicated, the crosslinks were reversed and RNAPII was immunoprecipitated. DNA was measured by qPCR using the indicated set of primers. ChIP values are represented as percentages of input. Error bars, ±s.d. (n=3). *P<0.05; **P<0.01 (unpaired t-test).

FIG. 4A: HeLa-CD4-LTR-LacZ cells chronically infected with pNL43 were treated with dCA for 60 days and treated with dCA for another 10 days (dCA) or stopped dCA treatment for 10 days (dCA Stop). Total RNA was extracted and reverse transcribed with random hexamer primers. The viral mRNA copies were quantified by qPCR and normalized with GAPDH mRNA. Viral mRNA output from untreated cells was assigned as 1. RNA extracts were used in the qPCR as negative control for the presence of genomic DNA contamination, 0.1% of the amplification of the cDNA samples is due to genomic DNA. The error represents a covariance of less than 5%.

FIG. 4B: Same as in FIG. 4A however the treatment was stopped for 27 days before harvest of the cells.

FIGS. 5A-5I: Potency of dCA and activity of dCA in primary cells.

FIGS. 5A-5D: Effect of dCA on acute replication of HIV-1 compared with known retroviral inhibitors. HeLa-CD4 cells were infected with HIV-1 pNL4-3 in the presence of the indicated compounds or DMSO. Forty hours post infection a CPRG assay was performed. Same dCA curve plotted in graphs FIGS. 5A-5D. Error bars represent standard deviation.

FIG. 5E: Analysis of viral mRNA expression upon treatment with dCA and retroviral inhibitors. Total RNA extracted four days after acute infection with pNL4-3 (MOI>>1) in the presence of drugs. First-strand cDNA was synthesized with random primers, and quantified by qPCR using primers recognizing the env and LTR regions. Results were normalized as copies of viral mRNA per copy of GAPDH mRNA. The arbitrary value of 1 was assigned to the DMSO control. RNA samples that were not reverse transcribed were used as negative control. Error bars represent standard deviation.

FIG. 5F: Activity of dCA on acute HIV-2 replication. HeLa-CD4 cells infected with ROD/A in the presence of the indicated concentrations of dCA. Antigen p24 in the supernatant measured using a sandwiched ELISA kit, 5 days post-infection.

FIG. 5G: Activity of dCA on chronic HIV-2 replication. HeLa-CD4 cells chronically infected with ROD/A in the presence of the indicated concentrations of dCA. Antigen p24 in the supernatant measured as in FIG. 5F, 7 days post-infection.

FIGS. 5H-5I: Activity of dCA on primary cells. Freshly isolated uninfected human PBMCs were stimulated with PHA for two days, washed, and grown from then on in IL-2 alone. Cells were infected with pNL43 in the presence of increasing concentrations of dCA and raltegravir. Antigen p24 was measured 5 days post infection using a sandwich ELISA kit.

FIG. 6A: dCA effect on $CD4^+$ T cells isolated from viremic subjects. Viral production from $CD4^+$ T cells isolated from five viremic subjects and grown in IL-2 was measured in the presence or absence of ARVs (RAL+AZT+EFV) supplemented or not with 100 nM dCA. Viral production was measured in the supernatant by a sensitive in-house ELISA for capsid p24 and normalized to the negative control (Mock). Statistical significance was assessed by a paired t-test.

FIG. 6B: dCA effect on $CD4^+$ T cells isolated from aviremic subjects. $CD4^+$ T cells isolated from PBMCs from four subjects who had been treated with HAART for at least 3 years were cultured for 6 days without IL-2 in the presence of ARVs to block de novo infection. dCA (100 nM) effect on the spontaneous release of HIV particles was assessed by measuring viral RNA in culture supernatants by ultrasensitive RT-PCR.

FIG. 8A: HeLa-CD4-LTR-Luciferase cells were treated with dCA and/or PMA at 10 nM for 8 hours. Luciferase activity measured and results adjusted per protein concentration of each sample, relative light units (RLU).

FIG. 8B: TE671 cells were transfected with an NF-kB luciferase reporter plasmid. The following day cells were treated with TNF-α in presence or absence of dCA. Cells were lysed 5 hours later and Luciferase activity was measured as in FIG. 8A.

FIG. 8C: Luciferase assays of TE671 cells transfected with the indicated promoter or promoter portion driving Luciferase expression. Main consensus bonding sites for transcription factors are indicated. 24 h post transfection cells were split and treated or not with CA. Forty hours later cells were lysed and luciferase activity measured as in FIG. 8A.

FIG. 8D: CEM SS and HeLa-CD4 cells stained for CD4, CXCR4 or isotype control expression followed by flow cytometry analysis.

FIG. 9A: Activity of Bio-dCA and dCA on acute HIV-1 infection, HeLa-CD4-LTR-LacZ cells reporter assay.

FIG. 9B: Mitochondrial Metabolic activity of HeLa-CD4 cells in the presence of Bio-dCA.

FIG. 10A: Kinase activity of CDK11 tested in vitro with 9G8 as substrate in presence of dCA (0.1 to 10 μM) or DMSO equivalent. CDK11 DN is a kinase inactive mutant used as negative control.

FIG. 10B: Expression of endogenous CDK11 in TE671 cells was not disturbed by increasing concentrations of dCA treatment for 48 h. Western blot with the indicated antibodies.

FIGS. 11A-11D: Effect of dCA on Tat-Flag cellular localization. Confocal microscopy analysis of the sub-cellular localization of transfected wt Tat(101)-1-flag, Tat(86)-1-BRM-flag, Tat-2-flag, Δ2-26-Tat(101)-1-flag and where indicated treated (24 h) or not with dCA. Flag recognized with anti-flag and AlexaFluor 568 anti-IgG antibodies. Endogenous fibrillarin stained with anti-fibrillarin and FITC-anti-IgG antibodies.

FIG. 11A: dCA dose response to Tat-flag and fibrillarin-GFP localization.

FIG. 11B: Effect of dCA on Tat or variants and fibrillarin.

FIG. 11C: No effect of dCA on cyclin T1. Endogenous cyclinT1 stained with anti-CyclinT1 and FITC-anti-IgG antibodies.

FIG. 11D: Bio-dCA affects Tat sub-cellular localization. All Transfections performed in HeLa cells. Magnification 300×.

FIG. 13A: Mitochondrial metabolic activity. MTT (3-[4,5-dimethylthiazol-2-yl]-2,5-diphenyltetrazolium bromide) assay on uninfected stimulated PBMCs incubated with increasing concentrations of dCA for 4 days.

FIG. 13B: Uninfected PBMCs staining with violet fluorescence amine-reactive viability dye (ViViD) or Annexin V. ViViD-AnnexinV-cells represent viable cells in the presence of increasing concentrations of dCA upon incubation with dCA for 1 or 3 days.

DETAILED DESCRIPTION

Figure 1A:
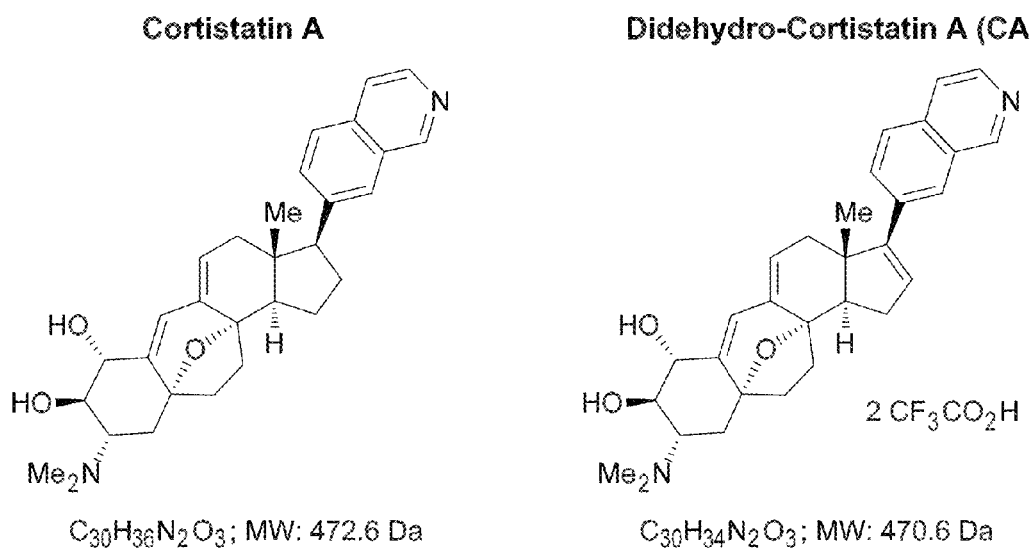

HIV drug therapy is based on the administration of drugs in combinations, in order to minimize development of mutations that can confer single-drug resistance to the virus. For optimal efficacy, drugs should target different stages of the virus life cycle. The viral protein Tat, a potent activator of HIV gene expression, is a potential antiviral target. Tat is required for viral gene expression during the exponential growth of the virus, as well as for transcription of the integrated proviral genome that gives rise to the mutation-rich genomic RNA from which drug-resistant strains of HIV-1 emerge. Because Tat is crucial for virus replication, it is the target for the development of several active compounds; however these showed low efficacy and none has yet been reported to have completed clinical trials.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

DEFINITIONS

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Treating" or "treatment" of a state, disorder or condition includes: (1) Preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; or (2) Inhibiting the state, disorder or condition, i.e., arresting, reducing or delaying the development of the disease or a relapse thereof (in case of maintenance treatment) or at least one clinical or sub-clinical symptom thereof; or (3) Relieving the disease, i.e., causing regression of the state, disorder or condition or at least one of its clinical or sub-clinical symptoms. The benefit to a subject to be treated is either statistically significant or at least perceptible to the patient or to the physician. Thus, "treating a retroviral infection", for example HIV should be understood as treating a patient who is at any one of the several stages of HIV infection progression, which, for example, include acute primary infection syndrome (which can be asymptomatic or associated with an influenza-like illness with fevers, malaise, diarrhea and neurologic symptoms such as headache), asymptomatic infection (which is the long latent period with a gradual decline in the number of circulating $CD4^+$ T cells), and AIDS (which is defined by more serious AIDS-defining illnesses and/or a decline in the circulating CD4 cell count to below a level that is compatible with effective immune function).

"Patient" or "subject" refers to mammals and includes human and veterinary subjects. The terms include any organism at risk of having or actually having a retroviral infection such as, for example, HIV, SIV, or SHIV, such as an mammal, including a macaque or human.

The term "HIV infection" generally encompasses infection of a host, particularly a human host, by the HIV family of retroviruses including, but not limited to, HIV I (also known as HTLV-III, LAV-1, LAV-2), and HIV II and the like. "HIV" can be used herein to refer to any strains, forms, subtypes, clades and variations in the HIV family. Thus, treating HIV infection will encompass the treatment of a person who is a carrier of any of the HIV family of retroviruses or a person who is diagnosed of active AIDS, as well as the treatment or prophylaxis of the AIDS-related conditions in such persons.

The term "SHIV" generally refers to a number of chimeric viruses constructed by recombinant DNA technology from parental viruses, simian immunodeficiency virus ("SIV") and HIV.

The term "preventing" refers to a process by which an initial HIV infection is prophylactically obstructed or the progression of which is inhibited or delayed. The term "preventing HIV infection" may also encompass treating a person who has not been diagnosed as having HIV infection but is believed to be at risk of infection by HIV.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, the terms "cortistatin(s)", "cortistatin agents", "cortistatin molecules" are used interchangeably herein and the terms are meant to include any cortistatin, cortistatin derivatives, analogs, substituted cortistatins or salts thereof. See, also for example, compounds having structures corresponding to Formulae I through XIII.

As used herein, "function" of a certain molecule (e.g. Tat, TAR) refers to any function that the molecule performs. Modulation of the function (e.g. binding to a molecule, transcription, translation, etc) is measured in the presence or absence of cortistatin agents as compared to controls.

As used herein, "activity" of a certain molecule refers to expression of or efficiency or degree to which that specific function is performed by the molecule in the presence or absence of the cortistatin agent as compared to a control. For example, if the function of the molecule is transcription, then the transcriptional activity can be measured. See, for example, the examples section which follow.

As used herein, the term "associated with" refers to any interactions one molecule may have with another either directly (e.g. binding to, enzymatic activity, etc.) or indirectly (e.g. modulates another molecule which has an effect on a different molecule (e.g. biochemical pathways, transcription pathways, enzymatic pathways, signaling etc.).

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, or flow cytometry.

Anti-Viral Agents

Although treatment with antiretroviral drugs has dramatically benefitted HIV-infected individuals, it has had a negligible impact on the global AIDS epidemic. AZT (zidovudine), introduced 25 years ago, was the first of approximately 30 antiretroviral drugs that have been licensed and are now in clinical use. Antiretroviral drugs fall in the following major classes: Fusion inhibitors (FIs), nucleoside reverse transcriptase inhibitors (NRTIs), non-nucleoside reverse transcriptase inhibitors (NNRTIs), nucleotide reverse transcriptase inhibitors (NtRTIs), protease inhibitors (PIs) and integrase inhibitors (INIs). Highly active antiretroviral therapy (HAART) is based on triple or quadruple combinations of NRTIs, NNRTIs and PIs and while reducing HIV to very low levels, fails to eliminate the infection completely and ultimately leads to the emergence of drug-resistant mutant strains. Thus, it is highly desirable to develop new anti-HIV agents with superior efficacy and safety profiles. Identification of compounds that repress HIV transcription activation is important, not only because it would constitute a new class of antiretroviral drugs, but also, due to the nature of their mode of action they could drastically reduce the emergence of drug-resistant strains.

In a preferred embodiment, an anti-viral agent comprises cortistatins, cortistatin derivatives, analogs, substituted cortistatins or salts thereof. An example of a cortistatin analog is a didehydro-cortistatin A (dCA). Cortistatins constitute a family of eleven steroidal alkaloids, isolated from the marine sponge *Corticium simplex*. The results obtained and described in the examples section which follows, evidence that cortistatin A is a promising anti-Tat drug candidate. Briefly, it was found that didehydro-cortistatin A (dCA) was a very potent inhibitor of Tat-activated transcription of the HIV-1 provirus. dCA was extremely efficient at reducing viral output from acutely infected cells, as well as from chronically infected cultured cells or freshly isolated peripheral blood lymphocytes (PBLs). The $EC_{50}$ of dCA for abrogating chronic HIV infection was less than 0.1 nM, a value>10 times lower than that for AZT (zidovudine; 5.2 nM), an antiviral currently used clinically. The cytotoxic concentration ($CC_{50}$) for dCA in cultured cell lines or freshly isolated PBLs was 20 μM, which confers on dCA a therapeutic index of approximately 200 000. Using biotinylated dCA, it was further demonstrated that dCA interacted directly with Tat, but not with a mutant version of Tat that fails to bind to its viral RNA target, TAR. Also identified was the interaction between dCA and the DNA-dependent protein kinase (DNA-PK) catalytic subunit by mass spectrometry in both infected and uninfected cells. Upon HIV infection DNA-PK tightly associates with Tat to promote the phosphorylation of the transcription factor Sp1, which results in increased HIV-1 transcription initiation, via three Sp1 binding sites in the core of the HIV-1 promoter. Without wishing to be bound by theory, it was hypothesized that dCA represses HIV replication in two ways; on the one hand inhibiting Tat-TAR interaction, and consequently inhibiting elongation by RNA Polymerase II (Pol II) from the HIV promoter; and on the other inhibiting DNA-PK activation of Sp1, and initiation of transcription by Pol II. Both routes would result in repression of HIV-1 transcriptional activation. DNA-PK is an example of one molecule which is associated with Tat.

Treatment of the viral infected cells in the viral infection with cortistatin molecules or agents results in inhibition of viral replication. Inhibition of viral replication with the method of the present invention results in suppression or a slowing down of the development of the disease and the elimination of the virus due to its inability to replicate, for example. Treatment can also provide a decrease of any symptoms of the viral infection that are present. The methods of the present invention are particularly useful in treating patients suffering from HIV infection to prevent the development of full blown AIDS. The methods of the present invention are also useful for treating a patient having AIDS. The methods of the present invention are particularly useful for treating patients having both an HIV infection and any associated disorders.

Retroviral Replication:

A determinant step in the replication of all retroviruses, including HIV-1, is the reverse transcription of the viral genomic RNA into cDNA and integration of the proviral genome into the host chromosome. The HIV-1 5' Long Terminal Repeat (5'LTR) becomes an eukaryotic transcription unit and transcription is then regulated by an interplay between a combination of viral and cellular transcription factors with binding sites present in the LTR. The LTR contains two tandem NF-kB elements followed by three tandem Sp1 binding sites and the TATA box sequence. NF-kB sites are required for basal transcription and Sp1 binding sites and the TATA box are required for basal transcription and Tat-mediated transactivation. After integration, RNA Polymerase II (Pol II) is recruited to the 5'LTR promoter and the viral genome is transcribed back into RNA. During the early phases of transcription, when the HIV transactivator Tat has not been yet made, cellular Pol II assembles at the promoter, and is initially phosphorylated at the C-terminal domain (CTD) by CDK7 kinase, which is part of the general transcription factor TFIIH. The modified Pol II clears the promoter and starts transcription of TAR, but Pol II stalls right after initiation and is inefficiently converted into the processive form. Only short non polyadenylated transcripts are produced (+1 to +59). Eventually Pol II is able to transcribe the entire proviral genome and the transcript is spliced producing an mRNA that encodes the viral Tat protein. Efficient elongation requires the recruitment by Tat of the positive transcription elongation factor b (P-TEFb) to a promoter proximal element (TAR), an RNA stem loop structure that spontaneously forms at the 5' extremities of the viral pre-mRNA. P-TEFb is composed of cyclin T1 and of cyclin dependent kinase 9 (CDK9), and is used at many promoters, including HIV-1, to phosphorylate serine 2 residues of the Pol II CTD, converting a nonphosphorylated form (Pol IIa) to a hyperphosphorylated form (Pol IIo) that engages in productive elongation. It has recently been found that Tat assembles first with P-TEFb before binding to TAR. The HIV-2 LTR is organized similarly to HIV-1 LTR and it contains a TAR element located downstream of the transcriptional initiation start site. Unlike the HIV-1 TAR element, which contains a single stem-loop, the HIV-2 TAR element consists of 2 characteristic stem-loop structures, both of which participate in optimal Tat response. While the HIV-1 TAR responds to HIV-1 and HIV-2 Tat equally well, the HIV-2 TAR element responds to HIV-2 tat somewhat more efficiently than to HIV-1 tat.

Tat protein contains 101 residues, with 1-72 amino acids encoded by a first exon and residues 73-101 encoded by a second exon, is considered as containing several domains. It should be noted that whereas an 86 amino acid form of Tat, which exists for a few laboratory-passaged virus strains (e.g. LAI, HXB2, pNL43), has been frequently used, this version represents a truncated and not naturally occurring full-length protein. In fact, a single nucleotide change in LAI, XB2 and/or pNL43 at putative residues 87 unmasks the conserved 101 amino acid protein.

When the provirus is integrated into the host chromosome it is packaged into chromatin and the LTR activity in the absence of any stimuli is silent. Tat-associated histone deacetylases TAHs (which include p300/CBP and p300/CBP-associating factor, PCAF) induce activation of chromatinized HIV-1 LTRs presumably through acetylation of histones. TAHs also directly acetylate Tat protein, regulating its association/dissociation to TAR that allow for Tat to bind to nascent TARs and to other cellular factors.

Tat also facilitates enhanced transcriptional initiation. Tat activation may be facilitated through protein-protein interactions with the transcription factor Sp1. Sp1 factors binding to the GC rich region of the HIV LTR may facilitate Tat recruitment proximal to the basal transcription machinery. Sp1 serves basal and activated functions at the HIV-1 promoter. In the absence of Tat, the HIV-1 LTR has a clear dependence on Sp1 for basal expression. At a later stage of virus replication, Sp1 cooperates synergistically with Tat to enhance further transcription from the LTR. Sp1 has been shown to interact with the TATA-binding protein (TBP), TBP tightly associated factor TAF110. TBP and TAF110 may function as coactivators that are essential for activated, but not basal, transcription. Additionally, mutational analysis of Sp1 and NF-kB binding sites may indicate functional cooperation between these two molecules. Sp1 is post-transcriptionally modified by glycosylation and phosphorylation in a manner that correlates with function. Double stranded DNA-dependent protein kinase (DNA-PK) has been identified as an SP1 kinase. DNA-PK is a serine/threonine multiprotein kinase comprised of a 350-kD catalytic subunit, p350, and Ku subunits (p70 and p80), which bind to nucleic acids. DNA-PK plays a role in DNA double strand break repair and in mediating V(D)J recombination events. Tat has been shown to interact directly with Sp1 and DNA-PK and this interaction seems to promote Sp1 phosphorylation, which consequently increases transcription from the HIV LTR.

In a preferred embodiment, an agent, such as for example, dCA inhibits HIV replication. The inhibition of replication could be due to any number of mechanisms, including, for example, inhibition of transcription initiation and/or elongation and/or possible dCA inhibition of Tat-TAR interaction in vivo. The various mechanism(s) of action include whether CA or dCA affect initiation of RNPII from the viral promoter and/or the elongation stimulated by Tat. The 5' terminal region (+1 to +59) of all HIV mRNAs forms an identical stem-bulge-loop structure called the Transactivation Responsive (TAR) element. Tat binds to TAR and activates transcription from the HIV LTR promoter. Basal transcription from the integrated HIV LTR is very low and Tat and host factors increase the mRNA production from the integrated viral genome up to 100 fold. Mutations in the TAR sequence usually affect Tat function and HIV replication, indicating a strong requirement for conservation of this structure. Without wishing to be bound by theory, it is hypothesized that TAR is a potential therapeutic target and anti-Tat drugs would have a synergistic effect with other inhibitors.

Screening based on Tat-TAR interaction has identified a number of compounds, however further characterization demonstrated these were only inhibitors of viral entry. Other molecules such as trans-dominant Tat mutants, TAR RNA analogs, antisense oligonucleotides, ribozymes, and polypeptides have all been used to inhibit the interaction between Tat and TAR or Tat and other cellular co-activators; but none of them is currently used in therapeutics partly because some of these strategies may not easily be delivered for an efficient therapy, emphasizing the need for small molecule compounds.

In the examples section which follows, the pharmacokinetics data demonstrated that CA and dCA could be dosed intraperitoneally or orally and plasma drug levels after 24 h post dose were still above the $EC_{50}$ value found in cell-based assays. The data shown herein, CA $EC_{50}$ for the inhibition of HIV activity is in the picomolar to low nanomolar range while $CC_{50}$ is 20 µM, conferring to CA an extremely high therapeutic index. CA specifically binds to Tat and this molecular interaction is probably at the basis of the inhibition of the TAR-mediated transactivation of the viral promoter. The data herein also show that CA and/or dCA binds DNA-dependent protein kinase. This interaction may result in reduced phosphorylation of Sp1, which might translate into a reduction of the basal activity of the promoter. Both events lead to an extremely efficient reduction of HIV viral transcription that in turn limits drastically the emergence of drug resistant mutants, rendering CA and/or dCA a very exciting and attractive anti-HIV compound.

In another preferred embodiment, a method of preventing viral infection or treating a viral infection in a patient, comprises administering to the patient a therapeutically effective amount of a cortistatin, including, for example, analogs, substituted cortistatin molecules, derivatives and the like. Preferably, the viral infection is a human immunodeficiency virus (HIV) infection. In some embodiments, the cortistatins can be administered with one or more pharmaceuticals used in treating HIV-infected patients. In a preferred embodiment, the cortistatin is cortistatin A and/or dCA. The administration of the cortistatin agents can be part of an antiviral therapy or can be administered alone. For example, HIV infected patients who are undergoing HAART therapy protocols can have any of the cortistatin agents administered pre-HAART, in conjunction with or after HAART therapy. In some embodiments, the doses and times of administration can be modified to tailor the therapy depending on the patient's condition, e.g. viral load, age, years of infection, weight, sex, and the like.

The antiviral drugs comprise one more of: fusion inhibitors (FIs), nucleoside reverse transcriptase inhibitors (NRTIs), non-nucleoside reverse transcriptase inhibitors (NNRTIs), nucleotide reverse transcriptase inhibitors (NtRTIs), protease inhibitors (PIs) or integrase inhibitors (INIs).

In another preferred embodiment, a method of modulating retroviral replication in vitro or in vivo comprises administering to a cell or patient an effective amount of cortistatin A and/or dCA. Preferably, the retroviral replication is modulated by at least 20% as compared to a baseline control, more preferably, the retroviral replication is modulated by about 90%, 95%, 96%, 97%, 98%, 99% or 100% as compared to a baseline control.

The inhibition or retroviral replication can be measured by any means known in the art e.g. pfu. Inhibitors of retroviral transcription can be measured by any methods known in the art. Exemplary methods are described in the examples section which follows. Modulators of Tat-TAR interactions, modulators of Tat or TAR functions or activities and identification of any molecules associated with these can be measured by any number of assays, e.g. pull-down assays, immunoassays, and the like. See, examples section which follows.

In another preferred embodiment, a method of inhibiting interaction of human immunodeficiency virus Trans-Activator of Transcription (Tat)-Transactivation Responsive element (TAR) in a cell or patient, comprises administering to the cell or patient an effective amount of cortistatin A and/or dCA. Preferably, the cortistatin agent inhibits retroviral transcription by modulating the function or activity of a Trans-Activator of Transcription (Tat), a Transactivation Responsive element (TAR), a molecule associated with Trans-Activator of Transcription (Tat) (e.g. binds to Tat or modulates the function or activity of Tat), a molecule associated with Transactivation Responsive element (TAR) (e.g. binds to TAR or modulates the function or activity of TAR), and/or interaction between a Trans-Activator of Transcription (Tat) and a Transactivation Responsive element (TAR) in patients.

In another preferred embodiment, a method of modulating function or activity of a human immunodeficiency virus (HIV) transcriptional promoter in vitro or in vivo comprises administering a therapeutically effective amount of an agent which modulates function or activity of a Trans-Activator of Transcription (Tat), a Transactivation Responsive element (TAR), a molecule associated with Trans-Activator of Transcription (Tat) (e.g. binds to Tat or modulates the function or activity of Tat), a molecule associated with Transactivation Responsive element (TAR) (e.g. binds to TAR or modulates the function or activity of TAR), and/or interaction between a Trans-Activator of Transcription (Tat) and a Transactivation Responsive element (TAR). An example of a molecule t binds to Tat is DNA-PK. Preferably the agent is a cortistatin agent comprising: a cortistatin, cortistatin derivatives, analogs, substituted cortistatins or salts thereof.

In another embodiment, the cortistatin agent modulates HTLV replication. The HTLV Tax protein has some features which resemble HIV Tat. In one embodiment, the cortistatin agent modulates activities, molecules associated with Tax or functions of Tax.

In another preferred embodiment, the cortistatin agent or molecule reduces or inhibits neurotoxicity. Tat released from infected lymphoid cells causes neuronal dysfunction associated with HIV-1 associated neurocognitive disease (HAND) in 50-70% of infected individuals, despite control of HIV replication in the periphery. CA binds within the neurotoxic domain of Tat (amino acids 31-61) and thereby reduce HAND.

In one embodiment, a method of preventing or treating neurotoxicity in a patient infected with a retrovirus, comprises administering to the patient a therapeutically effective amount of an agent which modulates function or activity of a Trans-Activator of Transcription (Tat), a molecule associated with Trans-Activator of Transcription (Tat), a molecule associated with Transactivation Responsive element (TAR) a Transactivation Responsive element (TAR) and/or interaction between a Trans-Activator of Transcription (Tat) and a Transactivation Responsive element (TAR), or DNA-PK.

Candidate Retroviral Inhibitors

Natural products have always been a valuable resource for the pharmaceutical industry, and many drugs derived from natural products have been of great benefit in virtually all clinical therapeutic areas. The Kobayashi group (S. Aoki et al., *J Am Chem Soc* 128, 3148 (Mar. 15, 2006)) isolated CA a novel steroidal alkaloid from the marine sponge *Corticium simplex*, which exhibits anti-angiogenic properties against human umbilical vein endothelial cells (HUVECs). The scarce natural supply prompted the chemical synthesis of CA. The Baran's laboratory route to CA synthesis departs from the cheap and abundant steroid, prednisone and requires only 13 chemical steps to the synthesis of didehydro-CA, the equipotent analog of CA (J. Shi et al., *Angew Chem Int Ed Engl* 48, 4328 (2009)). This synthesis approach is the only known route that can provide large (>gram) quantities of material in a cost-effective manner.

The data, shown in the examples section which follows, evidences that cortistatin A, a steroid drug like molecule, is a novel inhibitor of Tat transcriptional activation of HIV. No natural compounds have ever been previously shown to inhibit HIV replication in human test subjects. Briefly, the preliminary pharmacokinetics data demonstrated that CA could be dosed intraperitoneally or orally and plasma drug levels after 24 h post dose were still above the $EC_{50}$ value found in cell-based assays. CA $EC_{50}$ for the inhibition of HIV activity is in the picomolar to low nanomolar range while $CC_{50}$ is higher than 20 μM, conferring to CA an extremely high therapeutic index. CA specifically binds to Tat and this molecular interaction is probably at the basis of the inhibition of the TAR-mediated transactivation of the viral promoter. The data also show that CA binds DNA-dependent protein kinase. This interaction may result in a reduction of the accrued phosphorylation of Sp1 mediated by Tat and of Tat itself, which might translate into a reduction of the basal activity of the promoter. Both events lead to an extremely efficient reduction of HIV viral transcription that in turn limits drastically the emergence of drug resistant mutants, rendering CA and any derivative, analog, and substituted CA molecule, a very exciting and attractive anti-HIV compound. In a preferred embodiment, a pharmaceutical composition comprises cortistatin, cortistatin derivatives, analogs, substituted cortistatins or salts thereof. The cortistatin is preferably cortistatin A. An example of a cortistatin analog is a didehydro-cortistatin A (CA or dCA).

Candidate agents, such as for example, cortistatin derivatives, analogs, substituted cortistatins or salts thereof can be screened to determine whether they would be effective therapeutic agents. The candidate agents are not limited to cortistatins, but can be any type of molecule which may inhibit retroviral replication, such as, for example, HIV-1.

In some embodiments, the agents comprise aryl substituted compounds. See, for example, Shenvi et al., WO 2009/137335 incorporated herein by reference in its entirety).

In an embodiment, a cortistatin agent comprises a compound having a general structure of Formula I:

Formula I

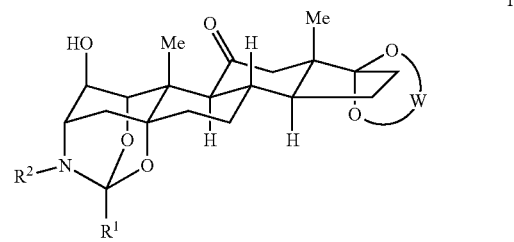

Wherein

W is the residuum of a saturated or unsaturated diol of 2 to about 12 carbon atoms that has been reacted with a ketone group to form the depicted ketal;

$R^2$ is COR, $CO_2R$, $SO_2R$, or $P(O)(OR)_2$, where R is hydrido (H), a straight chain, branched chain or cyclic alkyl, alkenyl, or alkynyl moiety, an aromatic, heterocyclic or alicyclic moiety that contains 1 to about 24 carbon atoms, in which a heterocyclic moiety contains 1 to four rings that each contain up to four ring atoms other than carbon that can be oxygen, nitrogen or sulfur; and $R^1$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur.

In one embodiment, a compound of Formula I comprises a structure corresponding to Formula II when W comprises 2 carbon atoms:

Formula II

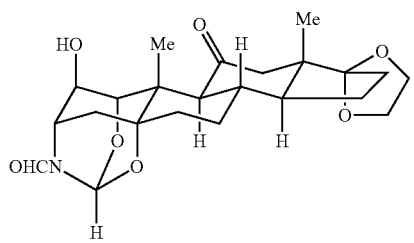

In another preferred embodiment, a cortistatin agent comprises a compound having a general structure of Formula VII:

Formula VII

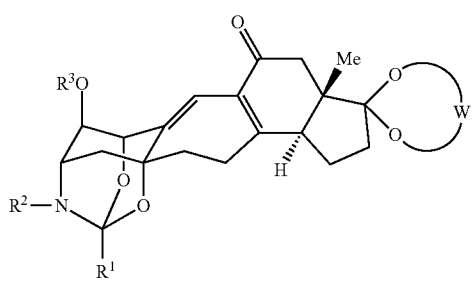

Wherein:

W is the residuum of a saturated or unsaturated diol of 2 to about 12 carbon atoms that has been reacted with a ketone group to form the depicted ketal;

$R^2$ is COR, $CO_2R$, $SO_2R$, or $P(O)(OR)_2$, where

R is hydrido (H), a straight chain, branched chain or cyclic alkyl, alkenyl, or alkynyl moiety, an aromatic, heterocyclic or alicyclic moiety that contains 1 to about 24 carbon atoms, in which a heterocyclic moiety contains 1 to four rings that each contain up to four ring atoms other than carbon that can be oxygen, nitrogen or sulfur;

$R^1$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur; and $R^3$ is a removable C1-C21 hydroxyl protecting group.

In another preferred embodiment, a cortistatin agent comprises a compound having a general structure corresponding to Formula VIII:

Formula VIII

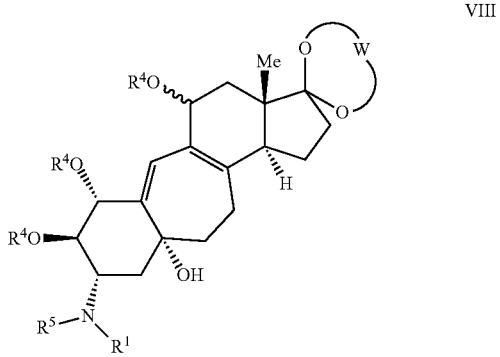

Wherein:

W is the residuum of a saturated or unsaturated diol of 2 to about 12 carbon atoms that has been reacted with a ketone group to form the depicted ketal;

$R^1$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur, —$R^4$ is an acyl group COR, $CO_2R$, $SO_2R$, or $P(O)(OR)_2$ that contains 1 to about 24 carbon atoms that can be a C1-C24 straight chain, branched chain or cyclic alkyl, alkenyl, or alkynyl moiety, an aromatic, heterocyclic or alicyclic moiety, in which a heterocyclic moiety can contain 1 to four rings that each contain up to four ring atoms other than carbon that can be oxygen, nitrogen or sulfur; and $R^5$ is hydrido (H), a straight chain, branched chain or cyclic alkyl, alkenyl, or alkynyl moiety, an aromatic, heterocyclic or alicyclic moiety that contains one to about 24 carbon atoms in which the heterocyclic moiety contains 1 to four rings that each contain up to four ring atoms other than carbon that can be oxygen, nitrogen or sulfur.

In one embodiment, a cortistatin agent of Formula VIII comprises a compound having a structure corresponding to Formula III when W contains 2 carbon atoms:

Formula III

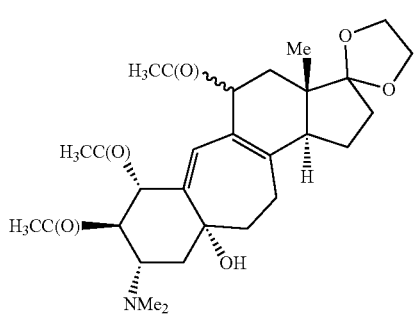

In another preferred embodiment, a cortistatin agent comprises a compound having a general structure corresponding to Formula IX:

Formula IX

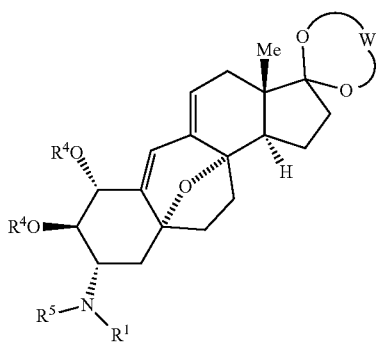

Wherein:

W is the residuum of a saturated or unsaturated diol of 2 to about 12 carbon atoms that has been reacted with a ketone group to form the depicted ketal;

$R^1$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur;

$R^4$ is an acyl group COR, $CO_2R$, $SO_2R$, or P(O) $(OR)_2$ that contains 1 to about 24 carbon atoms that can be a $C^\wedge$-$C_24$ straight chain, branched chain or cyclic alkyl, alkenyl, or alkynyl moiety, an aromatic, heterocyclic or alicyclic moiety, in which a heterocyclic moiety can contain 1 to four rings that each contain up to four ring atoms other than carbon that can be oxygen, nitrogen or sulfur; and, $R^5$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur.

In another preferred embodiment, a cortistatin agent comprises a compound having a general structure corresponding to Formula X:

Formula X

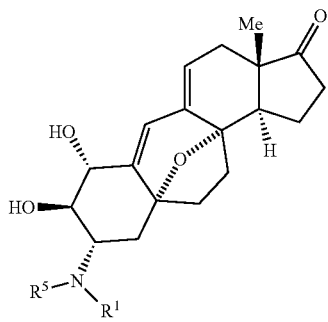

Wherein:

$R^1$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur; and $R^5$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur.

In one embodiment, a cortistatin agent of Formula X comprises a compound structure corresponds to the Formula IV when W contains 2 carbon atoms:

Formula IV

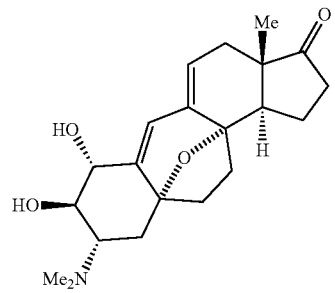

In another preferred embodiment, a cortistatin agent comprises a compound having a general structure corresponding to Formula XI:

Formula XI

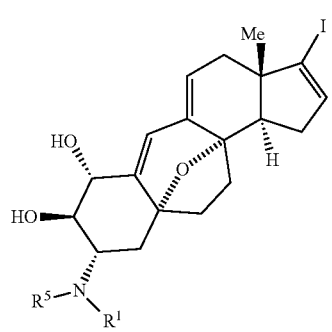

Wherein:

$R^1$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur; and, $R^5$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur.

In one embodiment, a cortistatin agent comprises a compound having a structure corresponding to the Formula V:

Formula V

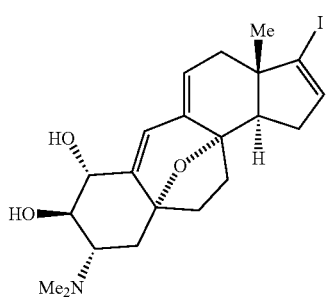

In another preferred embodiment, a cortistatin agent comprises a compound having a general structure corresponding to Formula XII:

Formula XII

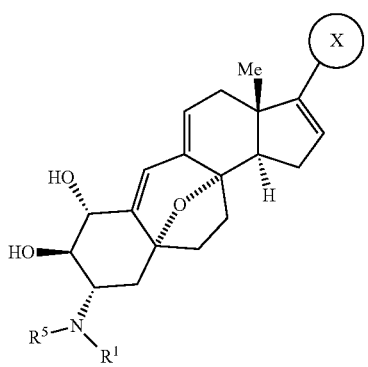

Wherein:

$R^1$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur;

$R^5$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur; and the circled X is a cyclic or heterocyclic substituent that contains 4 to about 15 carbon atoms, contains one to three saturated or unsaturated rings and up to three atoms per ring that are other than carbon and can be oxygen, nitrogen or sulfur.

In one embodiment, the compound according to Formula XII wherein the circled X group is aromatic.

In one embodiment, the cortistatin agent comprises a compound whose structure corresponds to Formula VI:

Formula VI

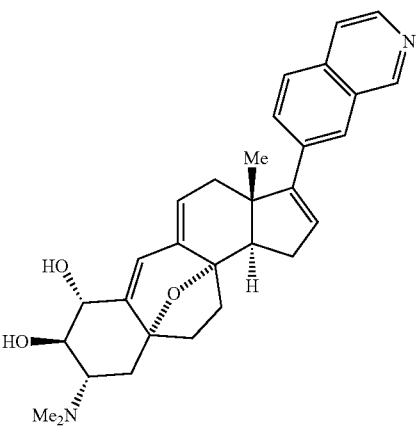

In another preferred embodiment, a cortistatin agent comprises a compound having a general structure corresponding to Formula XIII:

Formula XIII

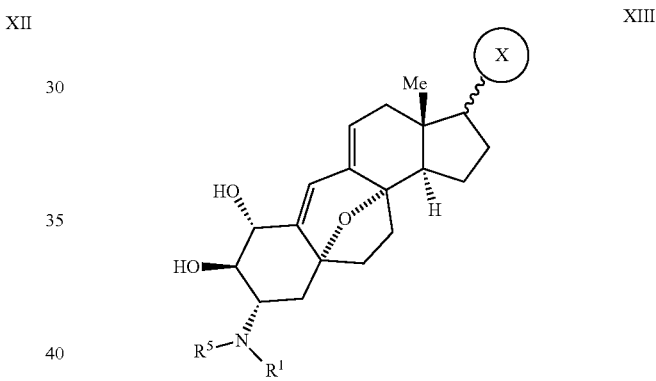

Wherein:

$R^1$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur;

$R^5$ is hydrido (H), a straight chain, branched chain or cyclic alkyl, alkenyl, or alkynyl moiety, an aromatic, heterocyclic or alicyclic moiety that contains one to about 24 carbon atoms, in which a heterocyclic moiety contains 1 to four rings that each contain up to four ring atoms other than carbon that can be oxygen, nitrogen or sulfur; and the circled X is a cyclic or heterocyclic substituent that contains 4 to about 15 carbon atoms, contains one to three saturated or unsaturated rings and up to three atoms per ring that are other than carbon and can be oxygen, nitrogen or sulfur; with the proviso that $R^1$ and $R^5$ are not both methyl when the circled X group is a 7-isoquinoline.

In one embodiment, the compound according to Formula XIII wherein the circled X group is aromatic. In one aspect, the circled X group is in the β-configuration.

Thus, in one preferred embodiment, candidate agents which inhibit replication of retroviruses, such as, for example, human immunodeficiency virus (HIV), comprises any one or more agents having structures corresponding to any one of Formulae I-XIII. These agents preferably modulate retroviral transcription by modulating the function or activity of a Trans-Activator of Transcription (Tat), a Trans-activation Responsive element (TAR), a molecule associated with Trans-Activator of Transcription (Tat) (e.g. binds to Tat or modulates the function or activity of Tat), a molecule associated with Transactivation Responsive element (TAR) (e.g. binds to TAR or modulates the function or activity of TAR), and/or interaction between a Trans-Activator of Transcription (Tat) and a Transactivation Responsive element (TAR), or other molecules involved or associated with transcription initiation and/or transcription of HIV in general.

In another preferred embodiment, candidate agents include any one or more agents which can modulate retroviral replication and can be identified by any number of ways. For example, in one embodiment, the agents are identified based on LTR-LacZ transactivation assays (cells express a β-galactosidase (lacZ) gene driven by the 5' LTR promoter of HIV-1 and this reporter cell line is responsive to Tat protein expressed by an incoming virus), and secondly by RB-FRET (fluorescence resonance energy transfer) of the Tat-TAR interaction. The method used herein "RNA-binding mediated FRET (RB-FRET)" allows special and temporal detection of specific RNA-protein complexes in living cells.

As discussed above, novel candidate agents can be substituted cortistatin A molecules, see for example, Formulae I to XIII. The term "substituted" means that a group in question may be unsubstituted or it may be substituted one or several times, such as 1 to 3 times or 1 to 5 times. For example, an alkyl group that is "substituted" with 1 to 5 fluoro atoms may be unsubstituted, or it may contain 1, 2, 3, 4, or 5 fluorine atoms. Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, haloalkyl including trifluoroalkyl, aralkyl, aryl, heteroaryl, heteroarylalkyl, spiroalkyl, heterocyclyl, heterocloalkyl, hydroxyl (—OH), alkoxyl, aryloxyl, aralkoxyl, nitro (—NO$_2$), cyano (—CN), amino (—NH$_2$), N-substituted amino (—NHR"), N,N-disubstituted amino (—N(R")R"), carboxyl (—COOH), —C(=O)R", —OR", —C(=O)OR", —C(=O)NHSO$_2$R", —NHC(=O)R", aminocarbonyl (—C(=O)NH$_2$), N-substituted aminocarbonyl (—C(=O)NHR"), N,N-disubstituted aminocarbonyl (—C(=O)N(R")R"), thiolato (SR"), sulfonic acid and its esters (—SO$_3$R"), phosphonic acid and its mono-ester (—P(=O)(OR")(OH) and di-esters (—P(=O)(OR")(OR"), —S(=O)$_2$R", —S(=O)$_2$NH$_2$, —S(=O)$_2$NHR", —S(=O)$_2$NR"R", —SO$_2$NHC(=O)R", —NHS(=O)$_2$R", —NR"S(=O)$_2$R", —CF$_3$, —CF$_2$CF$_3$, —NHC(=O)NHR", —NHC(=O)NR"R", —NR"C(=O)NHR", —NR"C(=O)NR"R", —NR"C(=O)R" and the like. In relation to the aforementioned substituents, each moiety "R" can be, independently, any of H, alkyl, cycloalkyl, alkenyl, aryl, aralkyl, heteroaryl, or heterocycloalkyl, or when (R"(R")) is attached to a nitrogen atom, R" and R" can be taken together with the nitrogen atom to which they are attached to form a 4- to 8-membered nitrogen heterocycle, wherein the heterocycloalkyl ring is optionally interrupted by one or more additional —O—, —S—, —SO, —SO$_2$—, —NH—, —N(alkyl)-, or —N(aryl)-groups, for example. In certain embodiments, chemical moieties are substituted by at least one optional substituent, such as those provided hereinabove. In the present invention, when chemical moieties are substituted with optional substituents, the optional substituents are not further substituted unless otherwise stated. For example, when R$^1$ is an alkyl moiety, it is optionally substituted, based on the definition of "alkyl" as set forth herein. In some embodiments, when R$^1$ is alkyl substituted with optional aryl, the optional aryl substituent is not further substituted.

When any variable occurs more than one time in any constituent or formula for a compound, its definition at each occurrence is independent of its definition at every other occurrence. Thus, for example, if a group is shown to be substituted with 0-2 substituents, then the group may optionally be substituted with up to two substituents and each substituents is selected independently from the definition of optionally substituted defined above. Also, combinations of substituents and/or variables are permissible only if such combinations result in stable compounds.

When a bond to a substituent is shown to cross a bond connecting two atoms in a ring, then such substituent may be bonded to any atom on the ring having an attached hydrogen atom. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In other embodiments, a cortistatin molecule may be chiral. The term "chiral" refers to molecules which have the property of non-superimposability of the mirror image partner, while the term "achiral" refers to molecules which are superimposable on their mirror image partner.

In other embodiments, a cortistatin molecule can be a stereoisomer. The term "diastereomers" refers to stereoisomers with two or more centers of dissymmetry and whose molecules are not mirror images of one another. The term "enantiomers" refers to two stereoisomers of a compound which are non-superimposable mirror images of one another. An equimolar mixture of two enantiomers is called a "racemic mixture" or a "racemate." The terms "isomers" or "stereoisomers" refers to compounds which have identical chemical constitution, but differ with regard to the arrangement of the atoms or groups in space.

Furthermore the indication of configuration across a carbon-carbon double bond can be "Z" referring to what is often referred to as a "cis" (same side) conformation whereas "E" refers to what is often referred to as a "trans" (opposite side) conformation. Regardless, both configurations, cis/trans and/or Z/E are contemplated for the compounds for use in the present invention. With respect to the nomenclature of a chiral center, the terms "d" and "1", "R" and "S", configuration are as defined by the IUPAC Recommendations. As to the use of the terms, diastereomer, racemate, epimer and enantiomer, these will be used in their normal context to describe the stereochemistry of preparations.

Unless specifically stated herein, the cortistatin, cortistatin derivatives, cortistatin analogs, substituted cortistatin A and salts thereof may contain any stereoisomer, racemate, or a mixture thereof.

In other embodiments, the cortistatin agent or molecule is labeled with a detectable moiety, including radionucleotides, enzymes, fluorescent agents, chemiluminescent agents, chromogenic agents, substrates, cofactors, inhibitors, magnetic particles, and the like.

In another preferred embodiment, the cortistatin molecule comprises a label for detecting the molecule in vivo (e.g. for imaging or diagnostic purposes) and/or to monitor the effects of the molecule during therapy.

In various embodiments, the cortistatin agents can be labeled with a detectable group. The detectable group can be any material having a detectable physical or chemical property. Such detectable labels have been well developed in the field of immunoassays and, in general, most labels useful in such methods can be applied to the present invention. Thus, a label is any composition detectable by spectroscopic, photochemical, biochemical, immunochemical, electrical, optical, or chemical means. In one embodiment, the CA is biotinylated. The biotinylated CA binds to streptavidin magnetic beads. Other useful labels in the present invention include magnetic beads (e.g., DYNABEADS™) which can be coated or conjugated to a desired molecule, fluorescent dyes (e.g., fluorescein isothiocyanate, Texas red, rhodamine, and the like), radiolabels (e.g., $^{3}H$, $^{125}I$, $^{35}S$, $^{14}C$, or $^{32}P$), enzymes (e.g., horseradish peroxidase, alkaline phosphatase and others commonly used in an ELISA), and colorimetric labels such as colloidal gold or colored glass or plastic beads (e.g., polystyrene, polypropylene, latex, etc.).

In one embodiment, is a radiolabeled compound of any of the molecules delineated herein. Such compounds have one or more radioactive atoms (e.g., $^{3}H$, $^{2}H$, $^{14}C$, $^{13}C$, $^{35}S$, $^{32}P$, $^{125}I$, $^{131}I$) introduced into the compound. Such compounds are useful for drug metabolism studies and diagnostics, as well as therapeutic applications.

In another embodiment, is a non-radiolabeled compound of the cortistatin molecules delineated herein. Some examples of non-radioactive labels include enzymes, chromophores, atoms and molecules detectable by electron microscopy, and metal ions detectable by their magnetic properties.

In another embodiment, is an enzymatic-labeled compound of the cortistatin molecules delineated herein. Some useful enzymatic labels include enzymes that cause a detectable change in a substrate. Some useful enzymes and their substrates include, for example, horseradish peroxidase (pyrogallol and o-phenylenediamine), β-galactosidase (fluorescein β-D-galactopyranoside), and alkaline phosphatase (5-bromo-4-chloro-3-indolyl phosphate/nitro blue tetrazolium). The use of enzymatic labels has been described in U.K. 2,019,404, EP 63,879, and by Rotman, Proc. Natl. Acad. Sci. USA, 47, 1981-1991 (1961).

In another embodiment, is a chromophore labeled compound of the cortistatin molecules delineated herein. Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

In another preferred embodiment, the cortistatin molecules are labeled for use in imaging. In imaging uses, the agents are labeled so that they can be detected outside the body. Typical labels are radioisotopes, usually ones with short half-lives. The usual imaging radioisotopes, such as $^{123}I$, $^{124}I$, $^{125}I$, $^{131}I$, $^{99m}Tc$, $^{186}Re$, $^{188}Re$, $^{64}Cu$, $^{67}Cu$, $^{212}Bi$, $^{213}Bi$, $^{67}Ga$, $^{90}Y$, $^{111}In$, $^{18}F$, $^{3}H$, $^{35}S$ or $^{32}P$ can be used. Nuclear magnetic resonance (NMR) imaging enhancers, such as gadolinium-153, can also be used to label the complex for detection by NMR. Methods and reagents for performing the labeling, either in the polynucleotide or in the protein moiety, are considered known in the art.

The labels may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label.

The present invention further encompasses salts, solvates, prodrugs and active metabolites.

The term "salts" can include acid addition salts or addition salts of free bases. Preferably, the salts are pharmaceutically acceptable. Examples of acids which may be employed to form pharmaceutically acceptable acid addition salts include, but are not limited to, salts derived from nontoxic inorganic acids such as nitric, phosphoric, sulfuric, or hydrobromic, hydroiodic, hydrofluoric, phosphorous, as well as salts derived from nontoxic organic acids such as aliphatic mono- and dicarboxylic acids, phenyl-substituted alkanoic acids, hydroxyl alkanoic acids, alkanedioic acids, aromatic acids, aliphatic and aromatic sulfonic acids, and acetic, maleic, succinic, or citric acids. Non-limiting examples of such salts include napadisylate, besylate, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, et al. "Pharmaceutical Salts," J. Pharma. Sci. 1977; 66:1).

The phrase "pharmaceutically acceptable," as used in connection with those compounds, materials, compositions, and/or dosage forms that are within the scope of sound medical judgment, suitable for contact with the tissues of human beings and animals without excessive toxicity, irritation, allergic response, or other problems or complications commensurate with a reasonable benefit/risk ratio. Preferably, as used herein, the term "pharmaceutically acceptable" means approved by a regulatory agency of the federal or a state government or listed in the U.S. Pharmacopoeia or other generally recognized pharmacopeias for use in mammals, and more particularly in humans.

Typically, a pharmaceutically acceptable salt of a compound such as one described herein or identified by the assays described, the compounds of the present invention may be prepared by using a desired acid or base as appropriate. The salt may precipitate from solution and be collected by filtration or may be recovered by evaporation of the solvent. For example, an aqueous solution of an acid such as hydrochloric acid may be added to an aqueous suspension of a compound of Formulae I to XIII and the resulting mixture evaporated to dryness (lyophilized) to obtain the acid addition salt as a solid. Alternatively, a compound may be dissolved in a suitable solvent, for example an alcohol such as isopropanol, and the acid may be added in the same solvent or another suitable solvent. The resulting acid addition salt may then be precipitated directly, or by addition of a less polar solvent such as diisopropyl ether or hexane, and isolated by filtration.

The acid addition salts of the compounds may be prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine.

The base addition salts of said acidic compounds are prepared by contacting the free acid form with a sufficient amount of the desired base to produce the salt in the conventional manner. The free acid form may be regenerated by contacting the salt form with an acid and isolating the free acid.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The salts of the Cortistatin A may form solvates (e.g., hydrates) and the invention also includes all such solvates. The meaning of the word "solvates" is well known to those skilled in the art as a compound formed by interaction of a solvent and a solute (i.e., solvation). Techniques for the preparation of solvates are well established in the art (see, for example, Brittain. Polymorphism in Pharmaceutical solids. Marcel Decker, New York, 1999.). Solvates may be represented, for example, by the formula R•(solvent), where R is a compound of the invention. A given compound may form more than one solvate including, for example, monosolvates (R(solvent)) or polysolvates $(R(solvent)_n)$ wherein n is an integer) including, for example, disolvates $(R(solvent)_2)$, trisolvates $(R(solvent)_3)$, and the like, or hemisolvates, such as, for example, $R(solvent)_{n/2}$, $R(solvent)_{n/3}$, $R(solvent)_{n/4}$ and the like wherein n is an integer. Solvents herein include mixed solvents, for example, methanol/water, and as such, the solvates may incorporate one or more solvents within the solvate.

The term "prodrug" includes compounds with moieties, which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19; Silverman (2004) The Organic Chemistry of Drug Design and Drug Action, Second Ed., Elsevier Press, Chapter 8, pp. 497-549). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halogen, or methoxy substituents) aryl and aryl-lower alkyl esters, amides, lower-alkyl amides, di-lower alkyl amides, and hydroxy amides. Other prodrug moieties include propionoic and succinic acid esters, acyl esters and substituted carbamates. Prodrugs which are converted to active forms through other mechanisms in vivo are also included.

As used herein, the term "hydrate" refers to a compound of the present invention which is associated with water in the molecular form, i.e., in which the H—OH bond is not split, and may be represented, for example, by the formula $R.H_2O$, where R is a compound of the invention. A given compound may form more than one hydrate including, for example, monohydrates $(R—H_2O)$ or polyhydrates $(R(H_2O)_n)$ wherein n is an integer>1) including, for example, dihydrates $(R(H_2O)_2)$, trihydrates $(R(H_2O)_3)$, and the like, or hemihydrates, such as, for example, $R(H_2O)_{n/2}$, $R(H_2O)_{n/3}$, $R(H_2O)_{n/4}$ and the like wherein n is an integer.

As used herein, the term "acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

A number of the compounds of the present invention and intermediates therefor exhibit tautomerism and therefore may exist in different tautomeric forms under certain conditions. As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is an imidazole moiety where the hydrogen may migrate between the ring nitrogens.

Valence tautomers include interconversions by reorganization of some of the bonding electrons. All such tautomeric forms (e.g., all keto-enol and imine-enamine forms) are within the scope of the invention. The depiction of any particular tautomeric form in any of the structural formulas herein is not intended to be limiting with respect to that form, but is meant to be representative of the entire tautomeric set.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both basic nitrogen atom and acidic groups often exist in equilibrium with their zwitterionic forms. Thus, any of the compounds described herein throughout that contain, for example, both basic nitrogen and acidic groups, also include reference to their corresponding zwitterions.

The invention has been described in detail with reference to preferred embodiments thereof. However, it will be appreciated that those skilled in the art, upon consideration of this disclosure, may make modifications and improvements within the spirit and scope of the invention. Embodiments of the invention may be practiced without the theoretical aspects presented.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1: Potent Suppression of HIV Viral Replication 1 by a Novel Inhibitor of Tat Although treatment with antiretroviral drugs (ARVs) has extended the quality and expectancy of life for people infected with HIV, it has been unsuccessful in curing HIV infection. ARVs fall into the following major classes: fusion inhibitors (FIs), nucleoside reverse transcriptase inhibitors (NRTIs), non nucleoside reverse transcriptase inhibitors (NNRTIs), nucleotide reverse transcriptase inhibitors (NtRTIs), protease inhibitors (PIs) and integrase inhibitors (INIs). Highly active antiretroviral therapy (HAART) is based on triple or quadruple combinations of ARVs, however while reducing HIV to very low levels, this treatment fails to eliminate the infection completely. Ultrasensitive assays revealed that HIV persists in latently and productively infected CD4$^+$ T cells in the peripheral blood of individuals receiving HAART who have maintained undetectable plasma viremia for prolonged periods of time. Residual viremia is not affected by the addition of an integrase or a fusion inhibitor to a stable HAART regimen suggesting that it originates from long-lived stable reservoirs that contain an integrated provirus that continuously produces viral particles despite HAART. Since viral production from these cellular reservoirs results from the continuous transcription of an integrated viral genome, they are not affected by NRTI, NNRTI, PIs, INIs or FIs.

The viral protein Tat, a potent activator of HIV gene expression, is a potential antiviral target. Tat is essential for the synthesis of full-length transcripts of the integrated viral genome by RNA polymerase II (RNAPII). Tat mediates association between the host positive transcription factor (pTEFb) complex and the trans-activation-responsive element (TAR) of the nascent viral RNA to promote transcriptional elongation from the viral promoter.

Cortistatin A (CA) is a recently discovered natural steroidal alkaloid isolated from the marine sponge *Corticium simplex*, and it has been reported to display anti-proliferative properties towards human umbilical vein endothelial cells (HUVECs) with an average half maximal inhibitory concentration ($IC_{50}$) of 0.35 µM. The scarce natural supply prompted the chemical synthesis of didehydro-Cortistatin A, the equipotent analog of Cortistatin A, starting from the inexpensive and abundant steroid prednisone and requiring only 13 steps for its synthesis (FIG. 1A). This synthetic route provides gram quantities of material in a cost-effective manner.

Here it is reported that didehydro-Cortistatin A (dCA) potently and selectively inhibits Tat-mediated trans activation of the integrated HIV provirus. dCA binds specifically to the TAR-binding domain of Tat and as a consequence, reduces cell-associated HIV-1 viral RNA and capsid p24 antigen production in acutely and chronically infected cultured and primary cells at an $EC_{50}$ as low as 0.7 pM. Moreover, in vitro dCA abrogates low-level virus replication from primary cells isolated from patients undergoing HAART treatment. In total, these results define dCA as a novel anti-HIV drug that could decrease residual viremia during HAART.

Materials and Methods

Cells:

HEK293T and CEM SS were obtained from the American Type Culture Collection (ATCC). Human peripheral blood mononuclear cells were obtained from the blood of healthy seronegative donors. HeLa, HeLa-CD4-LTR-Luc (PL11), HeLa-CD4-LTR-LacZ (P42), and HEK293T cells were cultured in DMEM supplemented with 5% FBS, L-glutamine (292 µg/ml) and antibiotics (100 units/ml penicillin and 100 µg/ml streptomycin). CEM SS, were cultured in Roswell Park Memorial Institut (RPMI) with 10% FetalcloneII (Hyclone) at 37° C. and 5% $CO_2$.

Viruses:

HIV particles were initially prepared by transient transfection of 293T cells with the proviral HIV-1 pNL4-3 DNA (Adachi A, et al. *J Virol.* 1986; 59(2):284-291) or ROD/A. Virus stocks for infections were produced by amplification of the virus by acutely infecting CEM SS cells with HIV-1 pNL4-3 and concentration by ultracentrifugation of the cell supernatant. Virus titers determined with HIV-1 p24 ELISA from Advances Bioscience Laboratories.

Plasmids:

pcDNA3.1 Tat-Flag-101 was generated by two-step PCR. The Tat sequence was amplified along with half of the Flag epitope via PCR and this product was then used to add the remaining Flag sequence. The final PCR product was cloned into pcDNA3.1-V5-HIS-B (Promega). pcDNA3.1 Δ2-26-Tat-Flag-101 was generated by PCR amplification from pcDNA3.1 Tat-Flag-101. pcDNA3.1 Tat-2-Flag-130 was generated using a similar two-step PCR approach as pcDNA3.1 Tat-Flag-101. NF-kB-Luc was purchased from Promega (Cat No. E8491).

Recombinant Tat Protein:

HIV-1 Tat protein, catalogue #2222 was obtained through the NIH AIDS Research and Reference Reagent Program, Division of AIDS, NIAID, NIH: HIV-1 Tat protein from Dr. John Brady and DAIDS, NIAID. GST-9G8 was purified using glutathion beads as previously described (Valente S T, et al., Mol Cell. 2009; 36(2):279-89).

Mitochondrial Metabolic Activity (MTT) Assay:

MTT (3-[4,5-dimethylthiazol-2-yl]-2,5-diphenyltetrazolium bromide) assay was performed on HeLa-CD4 cells in the presence of increasing concentrations of dCA according to the manufacturer's protocol (ATCC).

Evaluation of Toxicity by Flow Cytometry:

PBMCs from HIV negative subjects were incubated with increasing doses of dCA (0.1 dnM to 1 dμM). Viability was measured after 24 h and 72 h of culture. PBMCs were stained with FITC-labeled antibody to CD3 (555339), Alexa 700-labeled antibody to CD4 (557922), PerCP-Cy5.5-labeled antibody to CD8 (341051), V450-labeled antibody to CD14 (560349), V450-labeled antibody to CD19 (560353), APC-labeled antibody to AnnexinV (550474) and Live/Dead Aqua blue (L34957). All antibodies were purchased from BD Biosciences except for Live/Dead Aqua blue (Invitrogen). Analyses were performed on a LSRII (BD Bioscience) flow cytometer.

Tat Transactivation Assay—CPRG:

P42 cells were plated at $1 \times 10^4$ cells per well of 96 well. Twenty-four hours later HIV-1 pNL4-3 was added to the wells in the presence of testing compound or DMSO control in a total volume of 200 Forty hours post infection cells were disrupted in lysis buffer (60 mM Na$_2$HPO$_4$, 40 mM NaH$_2$PO$_4$, 10 mM KCl, 10 mM MgSO$_4$, 2.5 mM EDTA, 50 mM β-mercaptoethanol, 0.125% Nonidet P-40) and a quantitative chlorophenol red-β-D-galactopyranoside (CPRG)-based (Boehringer Mannheim) assay was performed. The cell extracts were incubated in a reaction buffer (0.9 M phosphate buffer [pH 7.4], 9 mM MgCl$_2$, 11 mM β-mercaptoethanol, 7 mM CPRG) until a red color developed (from approximately 10 min to 4 h) and measured with an LP400 (Becton Dickinson) plate reader at 572 nm. Experiments were performed in triplicate.

Isolation of Primary Lymphocytes:

To isolate PBMCs, 24 ml of total blood diluted two fold in RPMI or PBS were carefully layered over 12 ml of Ficoll-paque and centrifuged at 2000 rpm for 20 min (brakes off). Resultant layers are approximately from top to bottom: plasma-platelets-PBMC-Ficoll-red blood cells (with granulocytes). Most of the plasma was pipetted off and discarded. The buffy coat with PBMC's was carefully removed from 3 large (50 ml) tubes and transferred to a new 50 ml tube. The remaining Ficoll and red blood cells were discarded in closed tubes. Enough PBS was added to the PBMCs to make up 50 ml and centrifuged at 1200 rpm for 10 min, brakes on. The supernatant was decanted and the pellet was loosened and washed twice with PBS. Washed pellet was recovered in 30 ml of RPMI 1640 supplemented with 10% serum, 1% Penicillin-streptomycin and mixed well. PBMCs were counted and plated at $1 \times 10^6$ cells/ml. To activate the PBMCs, PHA (phytohaemagglutinin) was added at 3 μg/ml. Two to three days later add Interleukin 2 (IL2) at $3 \times 10^{-3}$ μg/ml.

Amplification of pNL4-3 in Primary PBMCs:

PHA activated PBMCs were centrifuged and recovered at $6 \times 10^6$ cells in 3 ml complete RPMI. Then 3 ml of viral supernatant was added and incubated for 4 h at 37° C. After this period, cells were centrifuged, washed 3 times with PBS and recovered in 3 ml complete RPMI. PBMCs were plated at 0.5 ml per well in a 6-well plate, and 0.5 ml media with DMSO control or anti-viral control at 2× final concentration was added. IL-2 was added at $3 \times 10^{-3}$ μg/ml. Supernatant was recovered for p24 assay every 3-4 days post infection. Cells were split at $1 \times 10^6$ cell per ml every 5-7 days.

HIV Production in CD4 T Cells from Viremic and Virally Suppressed Subjects:

All patients provided written informed consent, according to the guidelines of the ethics committee of the Oregon Health and Science University. CD4$^+$ T cells were isolated from PBMCs of HIV-infected subjects by negative magnetic selection (StemCell) and cultured for 9 days in the presence of IL-2 (30 UI/mL), antiretroviral drugs (AZT (180 nM), EFV (100 nM), RALT (200 nM)) and exposed to dCA 100 nM or 1 μM. Viral production was measured in the supernatant by a sensitive in-house ELISA specific for the viral capsid protein, p24. CD4$^+$ T cells from virally suppressed subjects were cultured for 9 days in the presence of antiretroviral drugs (ARVs) and exposed to dCA 100 nM or 1 μM. Viral production was measured by quantification of viral particle-associated RNA by ultra-sensitive two-step quantitative real-time reverse transcription-PCR (RT-qPCR). Briefly, viral particles in the cell culture supernatant were pelleted by centrifugation (60 min, 25000 g at 4° C.). To generate the standard curve, a sample of LAI-HIV with known titer was pelleted in the same run. After centrifugation, viral RNA was extracted with the QIAamp viral RNA extraction kit (Qiagen) according to the manufacturer's instructions.

RT-qPCR of Viral Particles:

Total viral RNA was reverse-transcribed into cDNA with gag gene-specific primers (25 pmol each), LM667 and GagR according to manufacturer's instructions (RT-PCR One Step kit—Invitrogen). Pre-amplified products were diluted in DNase-RNase free water, then subjected to quantitative real-time PCR on Rotor-Gene Q (Qiagen) in a reaction 25 pmol of the sense primer Lambda T, 25 pmol of the antisense primer AA55M, and 4 pmol of each hybridization probes (TIB MolBiol).

Cellular RNA Extraction:

Cells were trypsinized and washed twice with PBS. Total RNA was extracted using the RNA extraction kit (Qiagen) following the manufacturers instruction.

Real-Time PCR:

First-strand cDNA from RNA for qPCR was prepared using SUPERSCRIPTIII™ first-strand cDNA kit (Invitrogen), following the manufacturer's instructions, using approximately 5 μg of RNA as starting material and random hexamers as first-strand primers. Quantitative PCR was performed with an aliquot of cDNA as template, using LIGHTCYCLER® 480 SYBR Green I Master (Roche) in a 20 μL reaction according to the manufacturer's instructions. All reactions had a negative control in which no RT was added. The primers used were as follows:

5'GAPDH-
(5'-CAACAGCCTCAAGATCATCAGCA-3'; SEQ ID NO: 1),

3'GAPDH-
(5'-AGGGATGACCTTGCCCACAGCCTTGG-3'; SEQ ID NO: 2),

P1-
(5'-GACAAGAGATCCTTGATCTGTGGAT-3'; SEQ ID NO: 3),

P2-
(5'-CCTTGTAGAAAGCTCGATGTCAGC-3'; SEQ ID NO: 4),

P3-
(5'-GGCTAACTAGGGAACCCACTG-3'; SEQ ID NO: 5),

P4-
(5'-CTGCTAGAGATTTTCCACACTGAC-3'; SEQ ID NO: 6),

P5-
(5'-TGTATCCTTTAGCTTCCCTCAGATCACTCTTTGGC-3';
SEQ ID NO: 7),

P6-
(5'-CCTTTTCCATTTCTGTACA-3'; SEQ ID NO: 8),

P7-
(5'-ACTTACGGGGATACTTGGGCAG-3'; SEQ ID NO: 9),

P8-
(5'-CTCCATTTCTTGCTCTCCTCTGTC-3'; SEQ ID NO: 10),

P9-
(5'-GAAAAACATGGAGCAATCACAAGTAGCAATACAG-3';
SEQ ID NO: 11),

P10-
(5'-CAGATCAAGGATATCTTGTCTTCTTTGGGAGTGAA-3';
SEQ ID NO: 12),

GAPDH-Promoter-S:
(5'-ATGGTTGCCACTGGGGATCT-3'; SEQ ID NO: 13),

GAPDH-Promoter-AS:
(5'-TGCCAAAGCCTAGGGGAAGA-3'; SEQ ID NO: 14),

GAPDH-ORF-S:
(5'-GGAGGTGGCCTAGGGCTGCTC-3'; SEQ ID NO: 15),

GAPDH-ORF-AS:
(5'-GGTGGAATCATATTGGAAC-3'; SEQ ID NO: 16).

RT-qPCR of Viral Particles:

Total viral RNA (17 μL) was first treated with 1 unit DNase I (Invitrogen) for 10 min at 25° C. followed by DNase I inactivation with 1 μL 25 mM EDTA for 10 min at 65° C. Total viral RNA was then reverse-transcribed into cDNA for quantitative PCR analysis. RT-PCR was performed in a final volume of 50 μL containing 22 of DNase I treated RNA, gag gene-specific primers (25 pmol each), LM667 (5'-ATG CCA CGT AAG CGA AAC TCT GGC TAA CTA GGG AAC CCA CTG-3'; SEQ ID NO: 17) and GagR (5'-AGC TCC CTG CTT GCC CAT A-3'; SEQ ID NO: 18) and 2 μL of Superscript III RT/Platinum Taq mix (RT-PCR One Step kit—Invitrogen). Cycling conditions included reverse transcription (50° C. 30 min) followed by denaturation (94° C. 2 min), 20 cycles of amplification (94° C. 15 s, 62° C. 30 s, 68° C. 60 s) and a final elongation step (68° C. 5 min). The pre-amplified products were diluted (1:10) in DNase/RNase-free water, then subjected to quantitative real-time PCR on Rotor-Gene Q (Qiagen) in a 25 μl reaction containing 2× Rotor-Gene Probe PCR mix (Qiagen), 25 pmol of the sense primer Lambda T (5'-ATG CCA CGT AAG CGA AAC-3'; SEQ ID NO: 19), 25 pmol of the antisense primer AA55M (5'-GCT AGA GAT TTT CCA CAC TGA CTA A-3'; SEQ ID NO: 20), and 4 pmol of each hybridization probes 5'-CAC AAC AGA CGG GCA CAC ACT ACT TGA-3'-fluorescein (SEQ ID NO: 21) and LCred640-5'-CAC TCA AGG CAA GCT TTA TTG AGG C-3'-phosphate (SEQ ID NO: 22) (TIB MolBiol). The cycling conditions included an initial denaturation (95° C. 4 min), followed by 35 cycles of amplification (95° C. 10 s, 60° C. 10 s, 72° C. 9 s). Results were analyzed by using the RotorGene software (Qiagen).

Transfection and Protein Extraction:

HEK293T cells were transfected with 10 μg of the empty vector control pCDNA4, pFI-Tat-Flag-86WT or pCDNA3.1 9G8-Flag. Forty-eight hours post transfection, cells were washed twice with PBS and disrupted on ice with lysis buffer [20 mM Hepes (pH 7.4), 100 mM KCl, 0.2 mM EDTA, 5 mM β-mercaptoethanol, 0.1% IGEPAL CA-630, 10% glycerol and complete EDTA-free protease inhibitor cocktail (Roche)]. After centrifugation at 10000 g for 10 min at 4° C., supernatants were collected and protein concentration was determined by Bradford assay according to the manufacturer's instructions (Bio-Rad).

Bio-dCA Pull-Down:

DYNABEADS® MYONE™ Streptavidin T1 (12.5 μl slurry) (Invitrogen) were pre-saturated with 1.88 μl of 1 mM in DMSO of Biotin alone or Bio-dCA and incubated for 1 h at room temperature with orbital rocking, plus an additional 30 min with Biotin (0.63 μl of 1 mM in DMSO). Protein extracts (250 μg per sample) were incubated with the pre-saturated beads in lysis buffer supplemented with 0.1% BSA for 1 h at 4° C. with orbital rocking. After incubation, the beads were washed three times with lysis buffer. To elute the cellular proteins interacting with dCA, the beads were boiled 3 min in 2× Elution buffer [125 mM Tris-HCl (pH 6.8), 4% SDS, 5 mM β-mercaptoethanol, 20% glycerol, 0.004% Bromophenol Blue].

For the pull-down of recombinant Tat (#2222 of NIH) and GST-9G8, streptavidin-agarose beads (40 μl slurry) were pre-saturated with 1.5 μl of 1 mM in DMSO, Biotin alone, or Bio-dCA and incubated for 1 h at room temperature. Recombinant proteins were pre-incubated 10 min with DMSO, dCA, or Raltegravir in binding buffer (PBS 100 mM pH 73, 150 mM NaCl, BSA 0.1%, IGEPAL CA-630 0.001%) and then added to the beads for 1 h at 4° C. After incubation, the beads were washed three times with PBS and proteins were eluted as before.

Western Blot Analysis:

Cells were lysed in lysis buffer [20 mM Hepes (pH 8.0), 100 mM KCl, 0.2 mM EDTA, 5 mM β-mercaptoethanol, 0.1% IGEPAL CA-630, 10% glycerol and complete EDTA-free protease inhibitor cocktail (Roche)]. The lysate was centrifuged at 12,000 g for 5 min at 4° C. and the resulting supernatant was boiled in 6×SDS loading buffer. The protein extracts were separated by SDS-PAGE and transferred onto a polyvinylidene fluoride membrane. Membranes were probed with an anti-CDK11 (P2N) rabbit polyclonal antibody 1:1000, an anti-Flag M2 mouse monoclonal antibody 1:5000 (Sigma), an anti-GST rabbit polyclonal antibody 1:2000 (Bethyl), and/or an anti-ABCE1 (ab32270) rabbit polyclonal antibody 1:1000 (Abcam). The membranes were incubated in horseradish peroxidase-conjugated anti-mouse or anti-rabbit IgG goat polyclonal antibodies as secondary antibodies. Bands were visualized using the ECL Western blotting system (Amersham).

Luciferase Assay—Effect of Cortistatin A on TNF-α Activation of an NF-kB Reporter Construct:

TE671 cells were plated at $6.25 \times 10^4$ per well in a 24-well plate. Cells were transfected twenty-four hours later with either 200 ng or 400 ng of NF-kB-Luc (Promega, Cat No. E8491) using Fugene 6 (Roche) per manufacturer's instruction. The next day cells were split equally into two new wells and treated with TNF-α (30 ng/ml) and/or dCA (1 µM). Cells were lysed 5 hours later with 1× Lysis Buffer and luciferase activity was measured using the luciferase Assay System (Promega) on a Berthhold luminometer. Protein concentration was determined by Bradford assay. Results corresponding to the adjustment of the luciferase activity per protein concentration of each sample are shown as Relative light units (RLU). Experiments were performed in triplicate.

Tat Transactivation Assay:

PL11 cells were plated at $1 \times 10^5$ cells per well in a 6 well plate. The following day recombinant Tat protein (AIDS Research and Reference Reagent Program, Cat No. 11882) at 5 µg/ml and/or Cortistatin A at increasing concentrations were added to the cells, in culture media without serum and in the presence of 100 µM of chloroquine (increases Tat uptake). Five hours later, serum was added at 5% to the culture media. Forty hours later cells were lysed with 1× Lysis Buffer and luciferase activity was measured as before. Protein concentration was determined by Bradford assay. Results corresponding to the adjustment of the luciferase activity per protein concentration of each sample are shown as RLU.

In Vitro Kinase Assay:

Sixty ng of purified CDK11 wild-type (WT) or mutant (DN) were added to 2 µg of purified 9G8 in kinase buffer [50 mM Tris-HCl (pH 7.9), 20 mM MgCl2] and incubated 30 min on ice with dCA or the equivalent of DMSO. To the mixture, 100 µM of ATP and 5 µCi of γ-$^{32}$P-ATP (3000 Ci/mmol 10 mCi/ml) were added to a final volume of 30 µl in kinase buffer. Following 30 min at 30° C., the reaction was terminated by addition of 6 µl of 6× SDS loading buffer. After boiling for 10 min, proteins were separated by SDS-PAGE. The gel was dried and visualized by autoradiography.

Chromatin Immunoprecipitation (ChIP) Assay:

HeLa-CD4 cells chronically infected with pNL4-3 were seeded in 15 cm plates at $1 \times 10^6$ cells and treated 4-5 days with DMSO or dCA [0.1 and 10 nM] and 6-8 h with Flavopiridol[50 nM]. Cells were fixed with formaldehyde (1% [vol/vol]) to crosslink the chromatin and incubated at room temperature for 10 min. Crosslinking was arrested by adding glycine[0.125 M] and incubated for an additional 5 min at room temperature. Cells were then pelleted, washed twice with phosphate-buffered saline, ressuspended in SDS lysis buffer, and incubated 10 min on ice. All solutions used prior to the collection of chromatin-antibody complexes contained protease and phosphatase inhibitor cocktail. Cell lysates were sonicated 4 times for 10 s bursts on ice. The sheared chromatin was diluted by the addition of 3 volumes of ChIP dilution buffer (0.01% SDS, 1.1% Triton X-100, 1.2 mM EDTA, 16.7 mM Tris-HCl (pH 8.1), 167 mM NaCl) and pre-cleared with salmon sperm DNA-protein A/G agarose slurry for 2 h. Beads were removed by centrifugation, 10% of the pre-cleared chromatin supernatant was removed to serve as the pre-IP ('input') control, and the remaining pre-cleared chromatin was incubated with either 10 mg/ml of anti-RNAPII (Millipore #05-623) or non-specific rabbit IgG (Bethyl #P120-301) overnight. Chromatin-antibody complexes were collected by incubation with salmon sperm DNA-protein A/G agarose (50% slurry) and subsequent collection of beads by centrifugation. Bead pellets were washed in low-salt (0.1% SDS, 1% Triton X-100, 2 mM EDTA, 20 mM Tris-HCl (pH 8.0), 150 mM NaCl), high-salt (0.1% SDS, 1% Triton X-100, 2 mM EDTA, 20 mM Tris-HCl (pH 8.0), 500 mM NaCl), and LiCl (0.25M LiCl, 1% NP-40, 1% SDS, 1 mM EDTA, 10 mM Tris-HCl pH 8.0) immune complex wash buffers followed by two washes with TE buffer. Antibody-chromatin complexes were eluted from the beads by incubation with elution buffer (0.1% SDS, 0.1 M NaHCO$_3$). NaCl was added to eluates (final concentration of 0.2 M) and incubated at 65° C. for 4-6 h. The samples were then treated with RNase A and proteinase K, and the DNA was purified using the Qiaquick PCR purification kit (Qiagen) or by phenol/chloroform extraction followed by ethanol precipitation. The pre-IP input sample was purified in a manner similar to the bound ChIP fraction described above. Immunoprecipitated (IP) (2 µl) or input 10% (diluted 1:20) DNA was used in 20 µl qPCR mixtures with primers: P1(−426) and P2(−126) (LTR promoter), P5(1782) and P6(2207) (ORF pNL4-3). Primer sequences are shown above. A fraction of input was used to standardize the values obtained. The relative proportions of co-immunoprecipitated DNA fragments were determined on the basis of the threshold cycle (CT) for each PCR product.

The data sets were normalized to input values (percent input; 2CT(input)-CT(IP) 100).

Immunofluorescence:

HeLa cells were grown on fibronectin treated coverslips and transfected with the indicated plasmids. Following transfection, cells were treated with DMSO or dCA. Cells were then fixed with 3.7% formaldehyde. After fixation, the cells were permeabilized with 0.1% triton X-100 in PBS with 5% FBS. Primary antibodies (mouse α-FLAG M2 (Sigma), rabbit α-Fibrillarin C13C3 (Cell Signaling), and/or rabbit α-Cyclin T1 H-245 (Santa Cruz)) were added along with the permeabilization solution and incubated at room temperature for 1 hour. The cells were washed with PBS and incubated with 1:500 dilution of Alexa Fluor conjugated secondary antibodies in PBS containing 5% FBS for 1 hour in the dark. Following washing with PBS, the cells were placed on glass slides using mounting media containing DAPI and the coverslips were sealed for imaging on the FluoView FV 1000 laser scanning microscope.

Synthesis of Biotinylated dCA:

Compound 1-2 (4 mg, 5.7 µmol) and 3 (4 mg, 12 imp were dissolved in CH$_2$Cl$_2$:DMSO 10:1 (0.55 ml, 0.01 M). To this solution were added EDC (2.6 mg, 17 µmol, 3 equiv) and DMAP (1 mg, 9 µmol, 1.5 equiv). The reaction mixture was stirred at room temperature for 12 h, at which point it was quenched with sat. aq. NaHCO$_3$ (5 ml). The aqueous layer was extracted with EtOAc (4×5 ml). The combined organics were dried with MgSO$_4$, filtered, and concentrated in vacuo. The residue was then purified by HPLC, yielding 1a (1.2 mg, 25%) and 1b (1.7 mg, 25%) as a colorless oil.

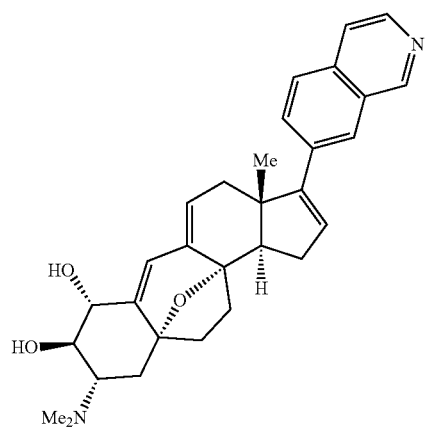

1.101

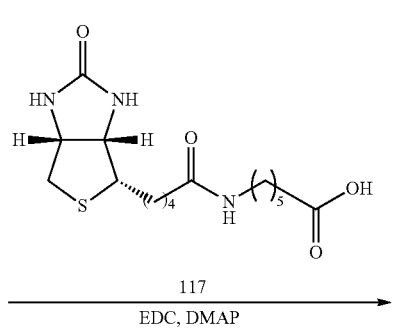

117
→
EDC, DMAP

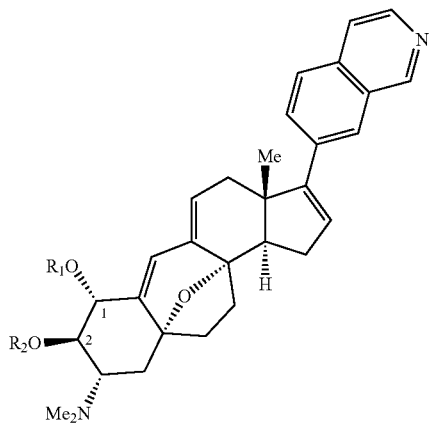

1.114a: R$_1$ = H, R$_2$ = R, 25%
1.114b: R$_1$ = R, R$_2$ = H, 34%

R = 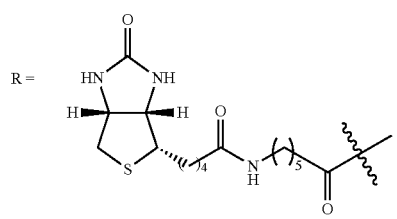

Results

Didehydro-Cortistatin A Inhibits HIV Transcriptional Activity:

Eukaryotic initiation factor 3 subunit f (eIF3f) mediates restriction of HIV-1 RNA 3' end-processing through the involvement of a set of factors that includes eIF3f, the SR protein 9G8, and cyclin-dependent kinase 11 (CDK11) (Valente S T, et al., (2009) *Proc Natl Acad Sci* USA 106, 4071-4078; Valente S T, et al., (2009) *Mol Cell* 36, 279-289). These data evidenced that a CDK11 inhibitor might possess anti-HIV activity. Given that Cortistatin A is a high affinity CDK11 ligand, the ability of its analog dCA to decrease HIV production by interfering with CDK11 activity was examined. While an effect of dCA on CDK11 activity was not confirmed, a potent activity as an inhibitor of HIV-1 transcription was identified.

Figure 1B:
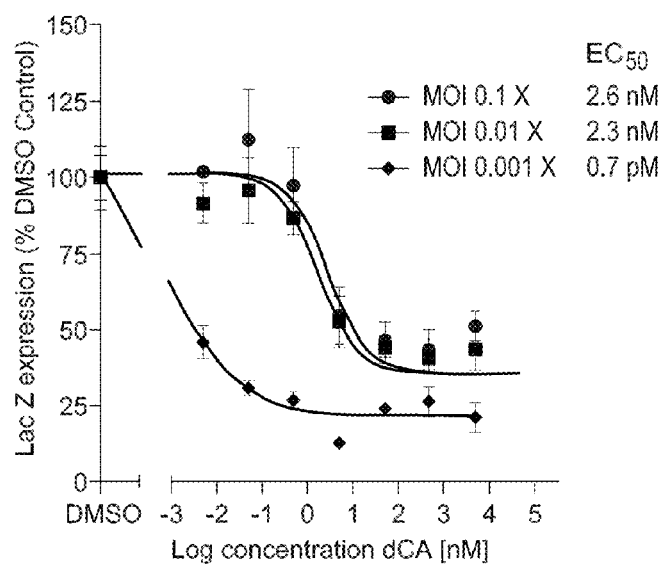
Figure 7:
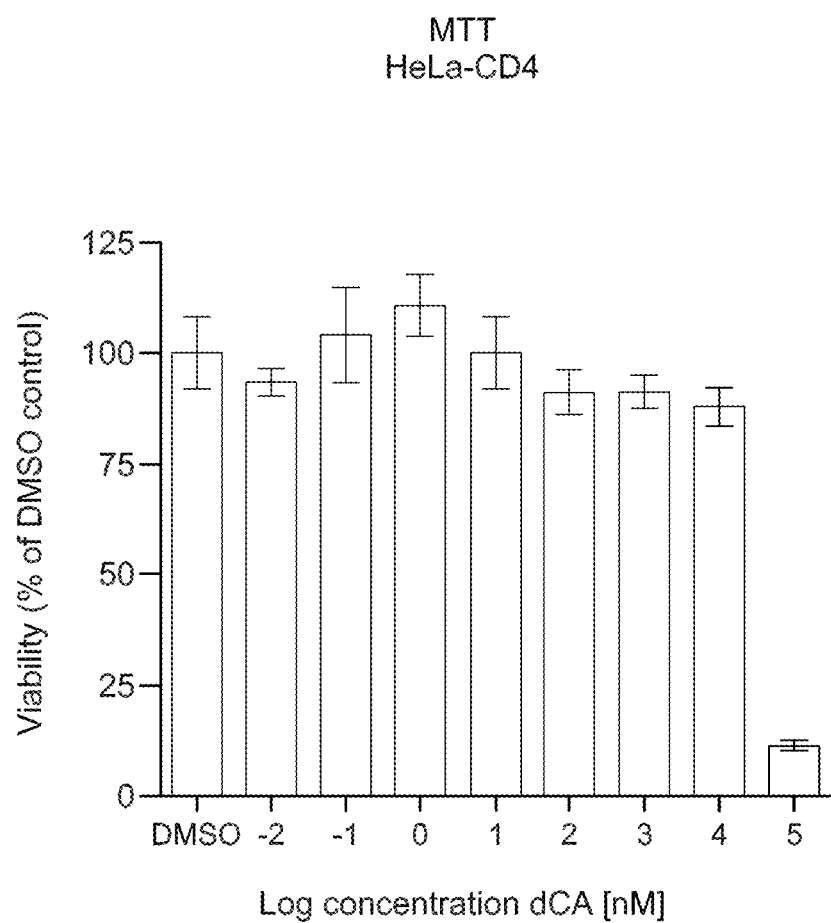
FIG. 7 shows the effect of dCA on cell viability. Mitochondrial metabolic activity. MTT (3-[4,5-dimethylthiazol-2-yl]-2,5-diphenyltetrazolium bromide) assay on HeLa-CD4 cells incubated with increasing concentrations of dCA for 4 days.

HIV-1 susceptibility to dCA was assayed using a reporter cell line that stably expresses β-galactosidase (LacZ) gene; LacZ expression is driven by the 5' long terminal repeat (LTR) promoter of HIV-1 and responds to Tat expressed by an incoming virus. HeLa-CD4-LacZ cells were infected with HIV-1 at different multiplicities of infection (MOIs) in the presence of increasing concentrations of dCA and β-gal activity was determined 48 h post infection (FIG. 1B). Inhibition of transcription was dose-dependent, with an EC$_{50}$ as low as 2.6 nM at the highest, and 0.7 pM at the lowest MOI; the lower MOI is more representative of biological amounts of virus found in infected subjects. Pre-treatment of cells with dCA for 24 h prior to infection resulted in a 7-fold reduction in the EC$_{50}$ (FIG. 1C), evidencing that dCA 92 potency depends on the time of addition or target concentration. Following acute infection, maximal inhibition leveled off at 75-85%, possibly due to the inability of dCA to block Tat-independent HIV transcription. Transcription of the HIV-1 provirus is regulated by both viral and cellular transcription factors. Before Tat is produced, low-level basal transcription from the viral promoter is initiated by cellular factors, such as the nuclear factor-kappa B (NF-kB), Sp1, TATA-binding protein and RNAPII. A desirable Tat inhibitor should block Tat-mediated activation of the viral promoter without affecting its basal transcription, which would result in cellular toxicity, given the shared transcription factors of the HIV promoter and cellular genes. The effective concentrations of dCA did not compromise HeLa-CD4 cell viability, as a half-maximal cytotoxic concentration (CC50) of 20 µM (FIG. 7) was observed.

To assess whether the viral block mediated by dCA occurs before or after integration of proviral DNA into the host cell chromosome, HeLa-CD4 cells were infected with HIV-1, treated with different concentrations of dCA and total cellular DNA was extracted 24 h later for quantification of proviral DNA by real time quantitative PCR (qPCR). Such an early time point rules out de novo infections. The presence of dCA did not change integrated HIV DNA copy number as compared with DMSO-treated cells (FIG. 1D). These results are consistent with a viral block by dCA at a step following-integration of the provirus into the host chromosome. Viral mRNA expression in cells treated with increasing concentrations of dCA was then measured by reverse transcription (RT) qPCR. A drastic dose-dependent reduction in the total amount of viral RNA in infected cells was detected (FIG. 1E), further evidencing that dCA inhibits transcription from the integrated viral promoter. This conclusion was further supported by the fact that treatment of cells that were chronically infected, and therefore continuously shedding the virus (without incurring new infections, due to down-regulation of CD4 from the cell surface), reduced virus production to undetectable levels (FIG. 1F). Treatment of chronically HIV-1 infected HeLa-CD4 cells with dCA for 10 or 60 days resulted in a drastic reduction of viral cellular RNA levels with an $EC_{50}$ as low as 0.1 nM and an $EC_{90}$ of less than 10 nM (FIG. 1F). Moreover, a continuous reduction in viral RNA levels was observed in the cell with increased treatment times with dCA, an expected result since Tat inhibition decreases Tat production. Results were similar when viral release from cells treated for 60 days were measured by p24 enzyme-linked immunosorbent assay (ELISA) (FIG. 1G). Furthermore dCA, but not other ARVs, reduced viral RNA levels in the lymphocytic cell line CEM SS chronically infected with pNL43 (FIG. 1H), demonstrating that the effect of dCA is not only cell-type independent but also that they extend to the reduction of viral expression from cells already infected, a result that none of the currently used ARVs is able to achieve.

Figure 8A:
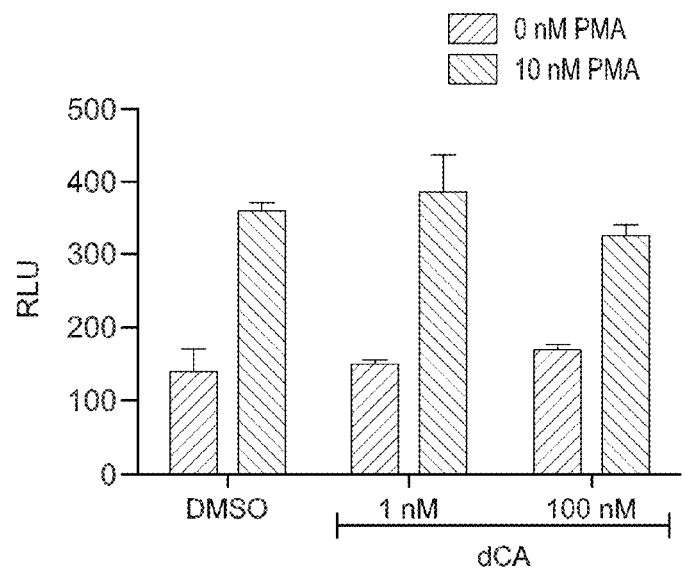
FIGS. 8A-8D show the transcriptional activity of the CXCR4, TK and CD4 promoters or NFκB reporter plasmid, not affected by dCA.
Figure 8B:
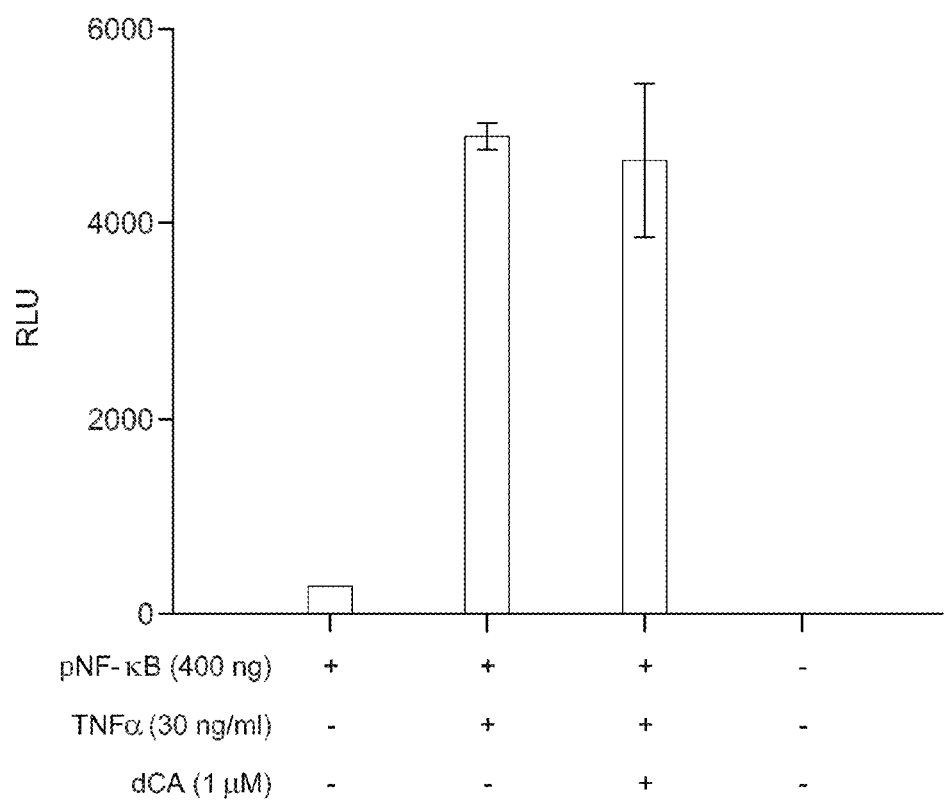
Figure 8C:
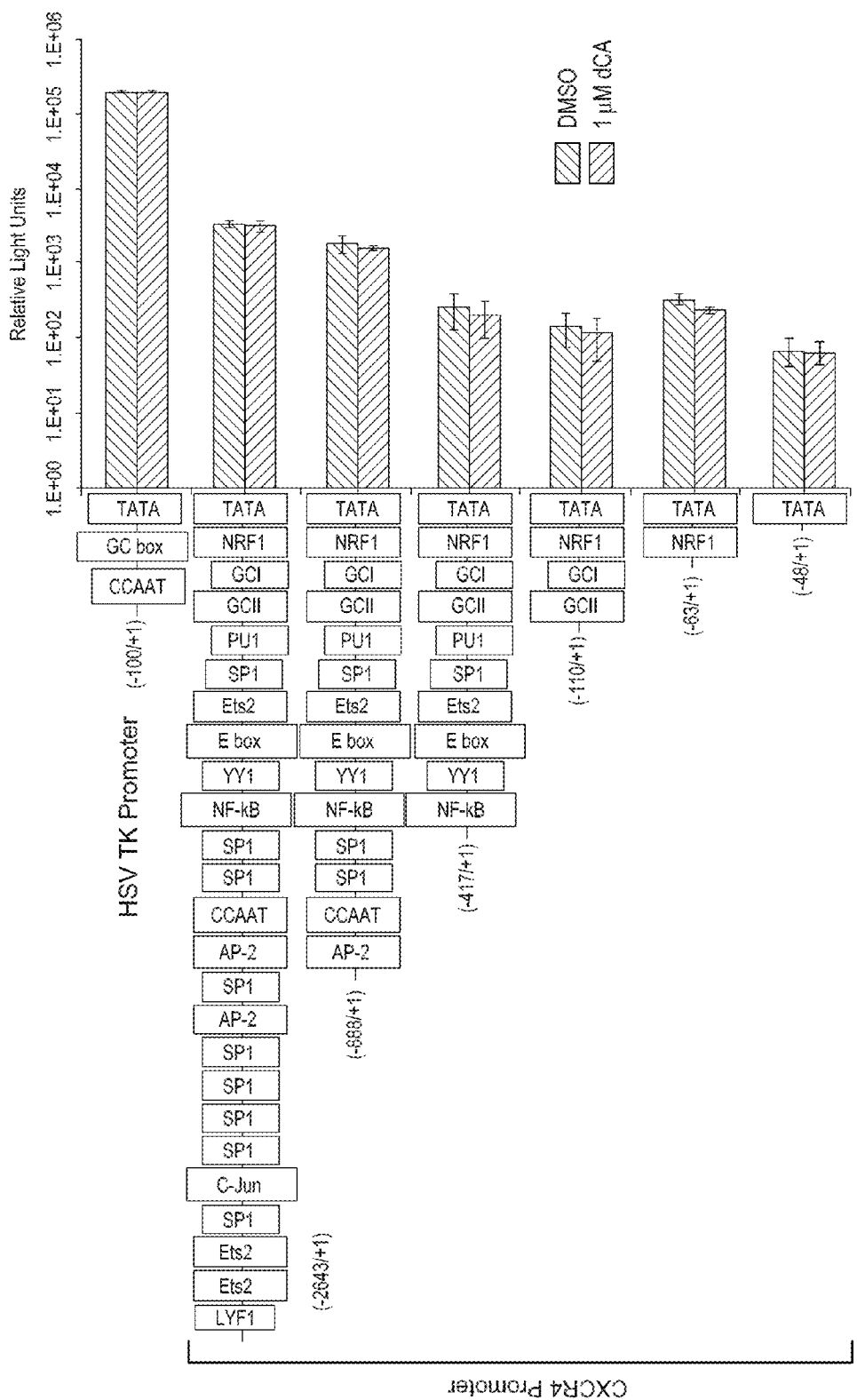
Figure 8D:
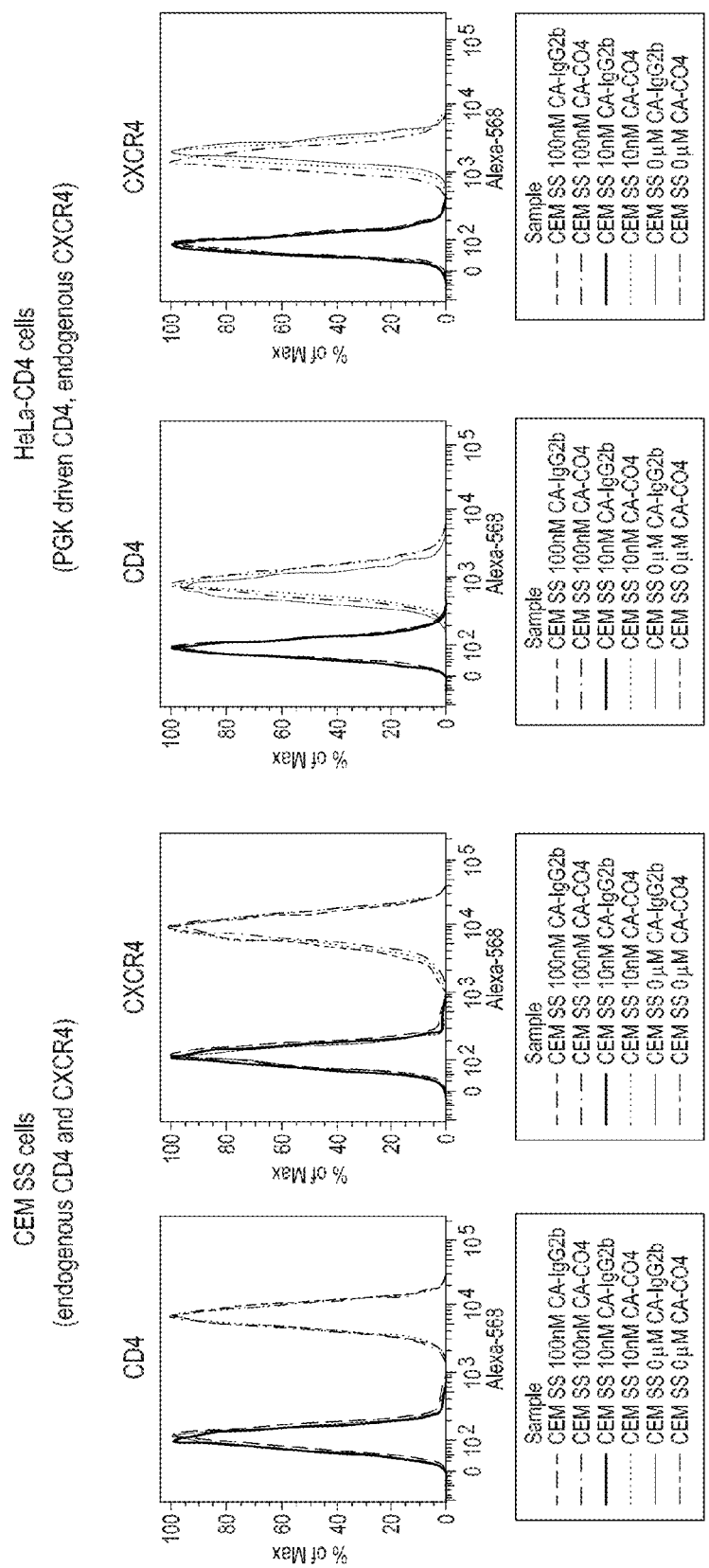

Didehydro-Cortistatin A is a Tat Inhibitor:

To determine whether dCA directly impacts Tat-mediated transcriptional activation from the viral promoter, a reporter system solely dependent on Tat activity was used. Recombinant Tat protein was added in the presence or absence of dCA to HeLa-CD4 cells stably expressing a construct containing the HIV-1 5'LTR promoter driving luciferase expression (LTR-Luc). Transcriptional repression was observed only in the presence of dCA (FIG. 2A). Similar results were obtained when a Tat-encoding plasmid was transfected into HeLa-CD4 expressing LTR-Luc (FIG. 2B). These results evidence that dCA blocks Tat transcriptional activation of the HIV-1 promoter. Reporter transcription from heat-inactivated recombinant Tat protein (FIG. 2A), which was used as negative control, reflects Tat-independent activation of the HIV promoter, and accounts for approximately 20% of maximal activation. This result supports the notion that the observed maximum inhibition plateau at 75-85% during acute infection is due to Tat-independent activity of the promoter. In line with these results, dCA did not alter basal transcription from the LTR promoter in the absence of Tat, nor when Phorbol 12-Myristate 13-Acetate (PMA) was used to activate promoter transcription via NF-kB (FIG. 2A). Furthermore, dCA showed no effect on TNFα activation of an NF-κB reporter construct (FIG. 8B), showing that inhibition by dCA is independent of NF-κB. Transcription from CXCR4, herpes simplex thymidine kinase (TK), phosphoglycerate kinase (PGK) or CD4 promoters was also not affected by dCA (FIGS. 8C, 8D).

Figure 2D:
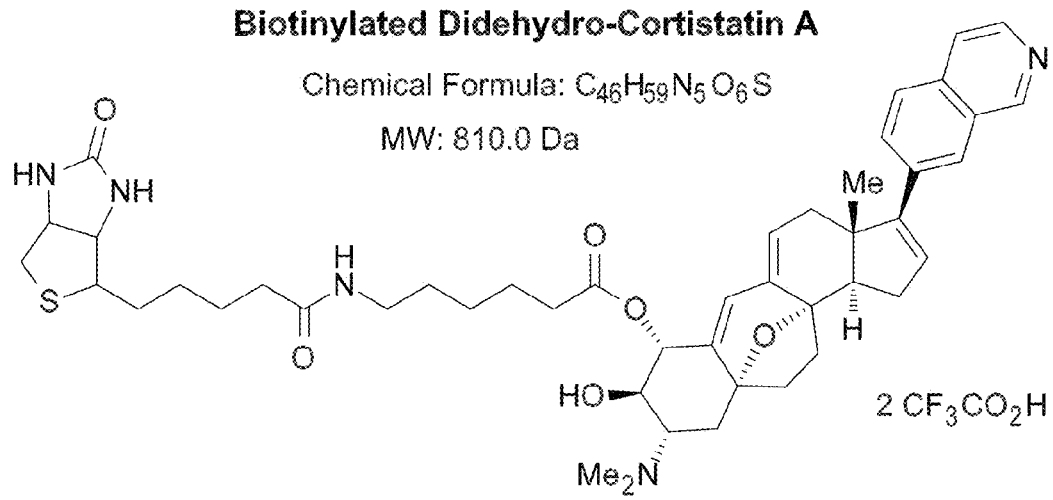
Figure 2E:
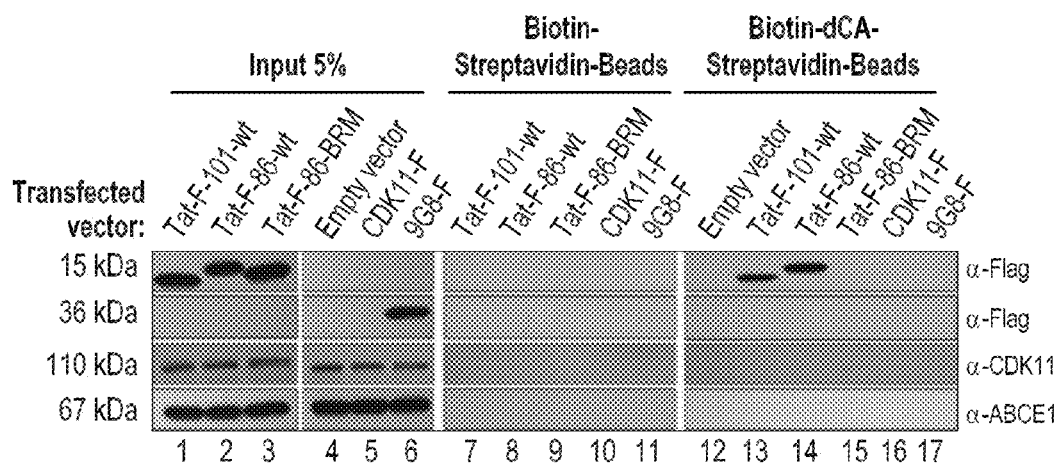
Figure 9A:
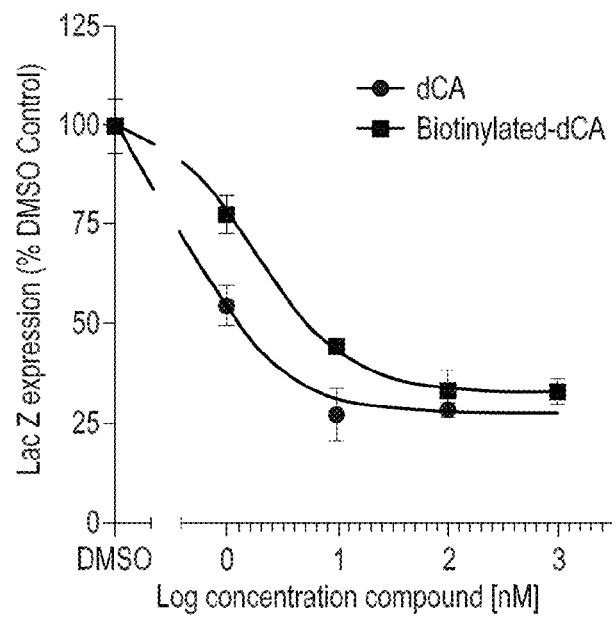
FIGS. 9A-9B: Biotinylated dCA activity and cell viability.
Figure 9B:
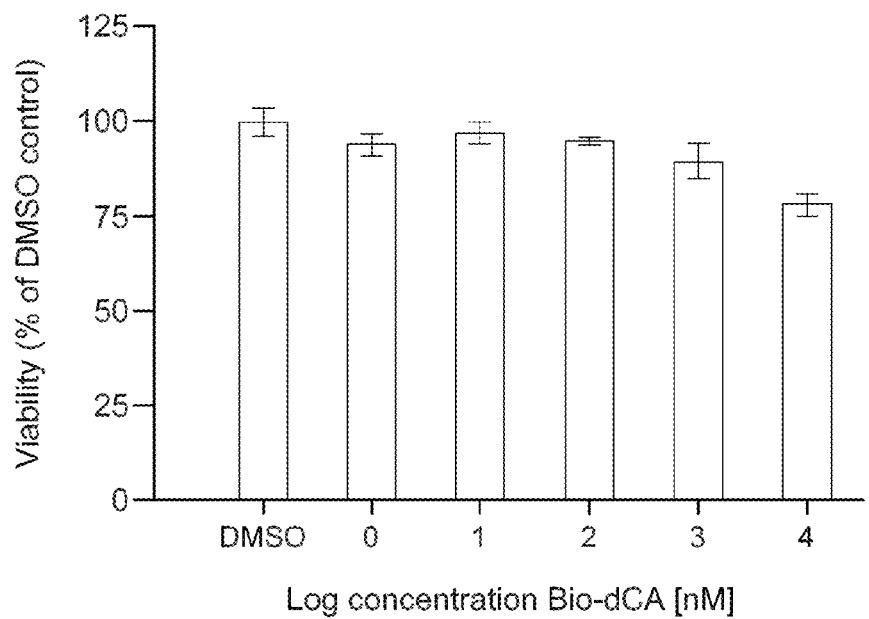
Figure 10A:
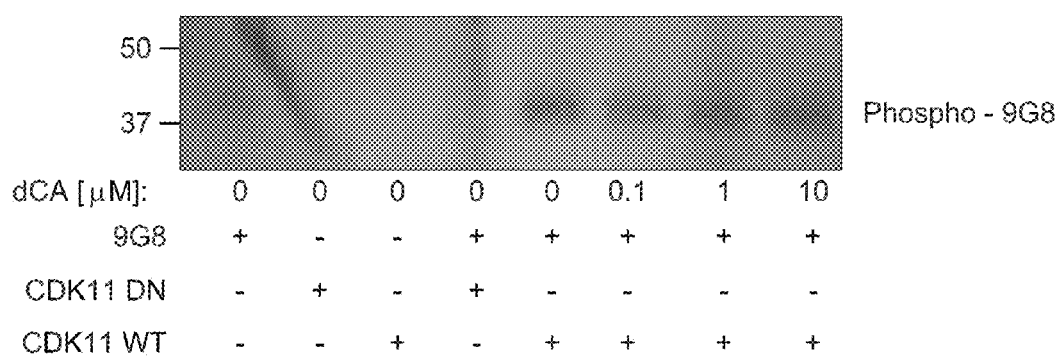
FIGS. 10A-10B: dCA does not inhibit CDK11 activity in vitro.
Figure 10B:
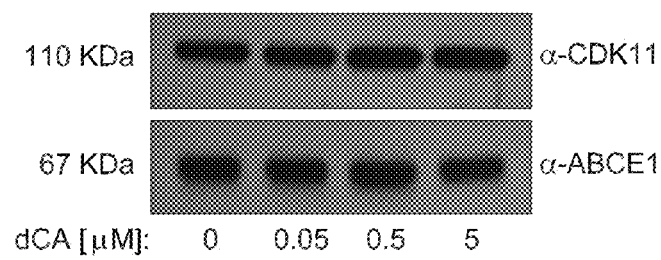

Tat is a 14 kDa, 101 residue protein with several functional domains (FIG. 2C). Domains II and III are essential for transactivation and domain IV mediates TAR RNA binding and nuclear localization. An 86-amino acid form of Tat (encompassing residues 1-86) is produced in a few laboratory-passaged virus strains and has been frequently used to study Tat. To determine whether Tat binds dCA a biotinylated form of the compound (Bio-dCA) (FIG. 2D) was synthesized. Notwithstanding, that this derivative displayed a tenfold higher $EC_{50}$ than dCA, at higher concentrations showed the same efficacy and did not compromise the viability of the cells (FIGS. 9A, 9B). Bio-dCA coupled to streptavidin-coated magnetic beads retained flag-tagged Tat (86 a.a.) or Tat (101 a.a.) transiently expressed in cells, but not a basic region Tat mutant (Tat-1 BRM) that no longer binds TAR and was therefore transactivation-incompetent (FIGS. 2C, 2E). Bio-dCA did not interact with the RNA-binding protein 9G8, ABCE1 protein (used as negative controls), nor with CDK11, which had been reported to interact with its analog CA in vitro. In line with the lack of interaction between dCA and CDK11, dCA was unable to block in vitro CDK11 kinase activity, and failed to alter the cellular expression profile of CDK11 (FIGS. 10A, 10B). In summary, an interaction between dCA and CDK11 was not found as possibly expected from the report suggesting an interaction between CDK11 and CA (Cee V J, et al., (2009) *Angew Chem Int Ed Engl* 48, 8952-8957).

Figure 2F:
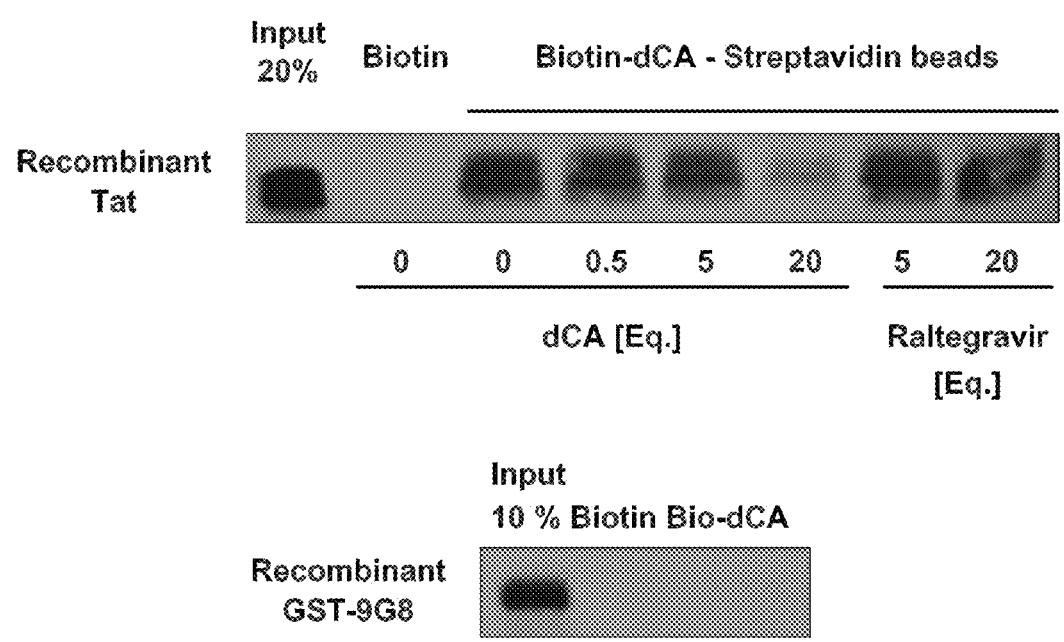

To confirm that Bio-dCA interacts directly with Tat pull-down experiments were performed with recombinant purified protein (FIG. 2F). Recombinant Tat protein bound directly to Bio-dCA and was competed by CA but not by Raltegravir, used as negative control, demonstrating the specificity of the interaction. As expected, Bio-dCA did not associate with purified recombinant 9G8 used as negative control.

While it is well known that Tat accumulates in the nucleolus via its basic region, Tat function in this compartment is still largely unknown. The nucleolus, a highly organized, non-membrane-bound-subcompartment, is involved in transcription and maturation of rRNA and ribosome biogenesis as well as in apoptosis and cell cycle contro. Some studies suggest that the nucleolus plays a role in HIV-1 infection. First, lymphocytes isolated from infected patients show abnormal nucleolar structure, and second, nucleolar localization of TAR impairs virus replication.

Figure 2G:
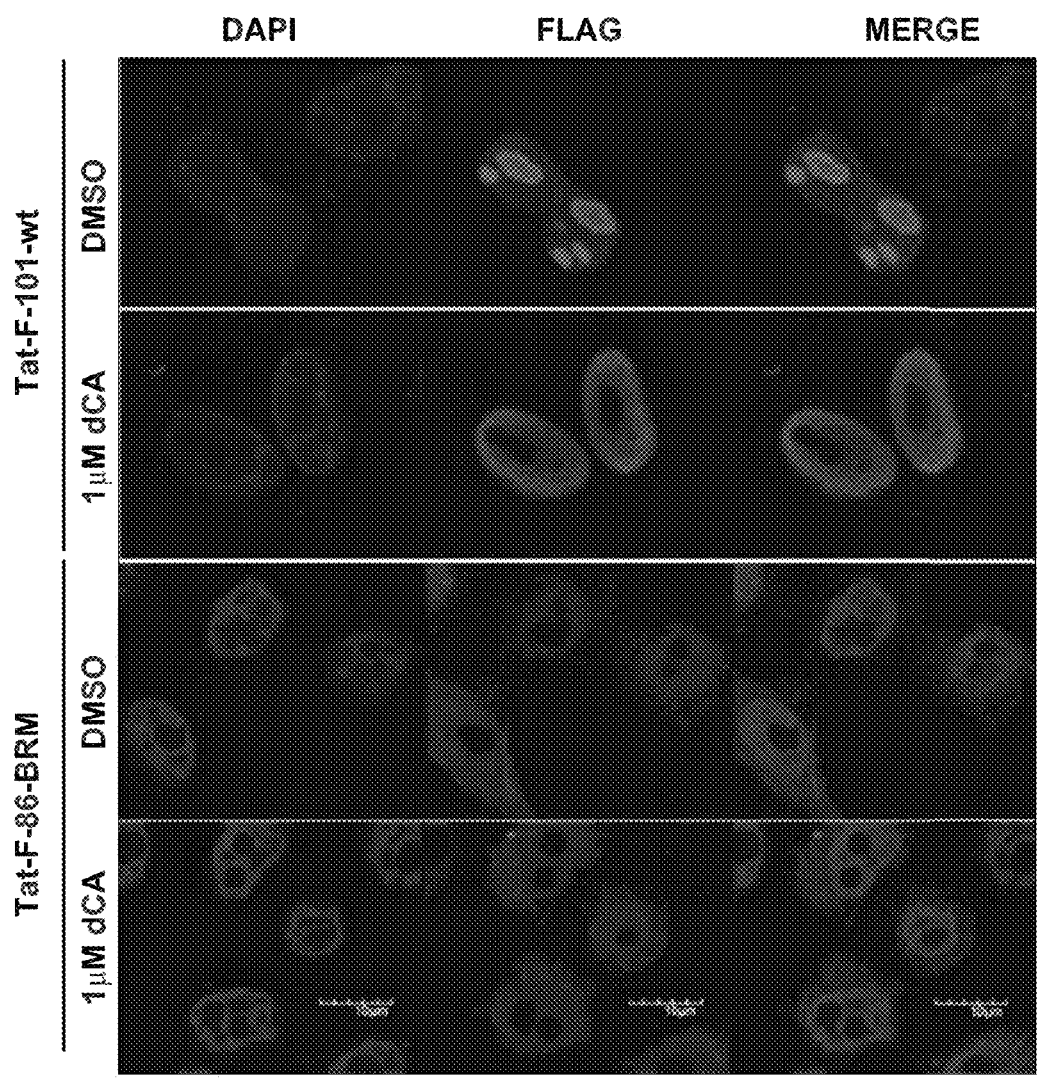

Given that dCA interacts with Tat via its basic domain, which is also the nucleolar localization signal (NoLS), it was questioned whether dCA impacts Tat localization. To address this possibility, HeLa-CD4 cells were transfected with a plasmid expressing Tat-flag and assessed Tat localization in the presence or absence of dCA by fluorescence microscopy upon immunostaining with an anti-flag antibody (FIG. 2G). dCA caused a redistribution of Tat to the periphery of the nucleolus, forming a distinctive ring-like structure (FIG. 2G), in a dose-dependent manner (FIG. 11A). The Tat basic mutant was analyzed in parallel, and this protein was completely excluded from the nucleolus both in the presence or absence of dCA. The effect of dCA on wild-type Tat appears to mimic the phenotype caused by the basic domain mutation (FIG. 2G and FIG. 11B). The Δ2-26-Tat mutant lacks the transactivation domain but retains the basic domain and shows a predominantly nucleolar localization. In the presence of dCA, this mutant was like wild-type Tat, excluded from the nucleolus, consistent with the presence of the basic domain (FIGS. 11B, 11C). The localization of fibrillarin, a component of small nucleolar ribonucleoproteins (snoRNPs) or of cyclin T1, a Tat-binding protein, was not altered by dCA (FIGS. 11A, 11B, 11C). The biotinylated form of dCA had the same effect on Tat localization (FIG. 11D). As Tat localizes to the nucleolus via the basic region, these results support the biochemical data showing a direct interaction of dCA with Tat via the TAR binding domain.

Didehydro-Cortistatin A Blocks Transcriptional Initiation/Elongation:

p-TEFb is composed of cyclin T1 and cyclin-dependent kinase 9 (CDK9) and is recruited by Tat to the HIV TAR region. pTEFb is used at many promoters, including HIV-1, to phosphorylate serine 2 residues present in the RNAPII C-terminal domain (CTD), converting a nonphosphorylated to a hyperphosphorylated RNAPII form that engages in productive elongation. The effects of dCA on transcription initiation and elongation from the 5'LTR by RNAPII were analyzed by qRT-PCR and chromatin immunoprecipitation (ChiP).

Figure 3A:
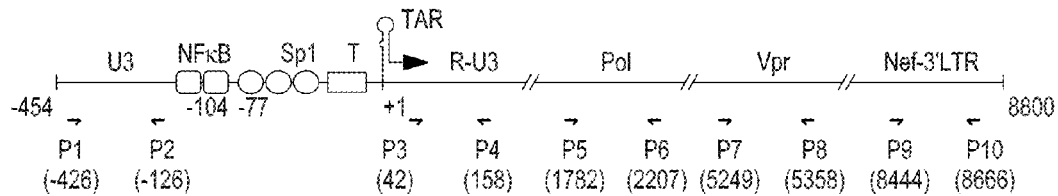
FIGS. 3A-3C: RNAPII elongation from viral promoter is inhibited by dCA.
Figure 3B:
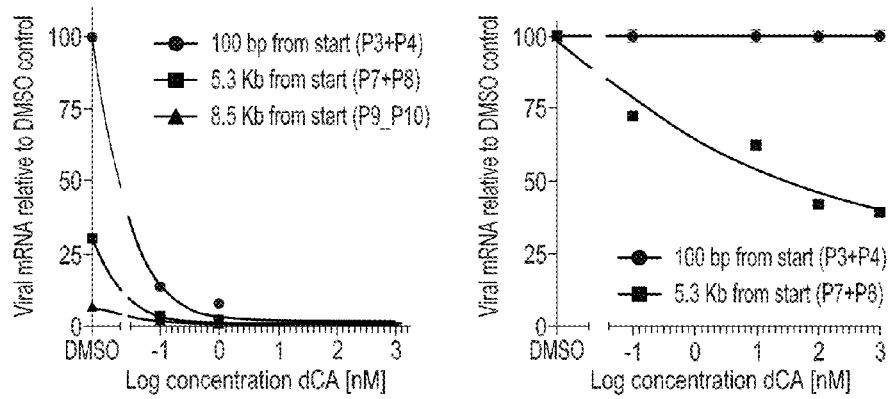

For these studies, the amounts of viral RNA present at different distances from the promoter were measured using sets of oligonucleotide primer pairs specific to quantify transcripts made up to 100 bp, 5.3 kb or 8.5 kb from the transcription start site (FIG. 3A). It was observed that even in the absence of drug, elongation from the HIV-1 viral promoter is not very efficient. In the presence of DMSO alone only 30% of 5.3 kb long transcripts and 6% of 8.5 kb long transcripts were produced (FIG. 3B—left panel). The addition of dCA further decreased the production of longer viral RNA species in a dose-dependent manner (FIG. 3B), supporting the notion that dCA inhibits elongation from the viral promoter.

Figure 3C:
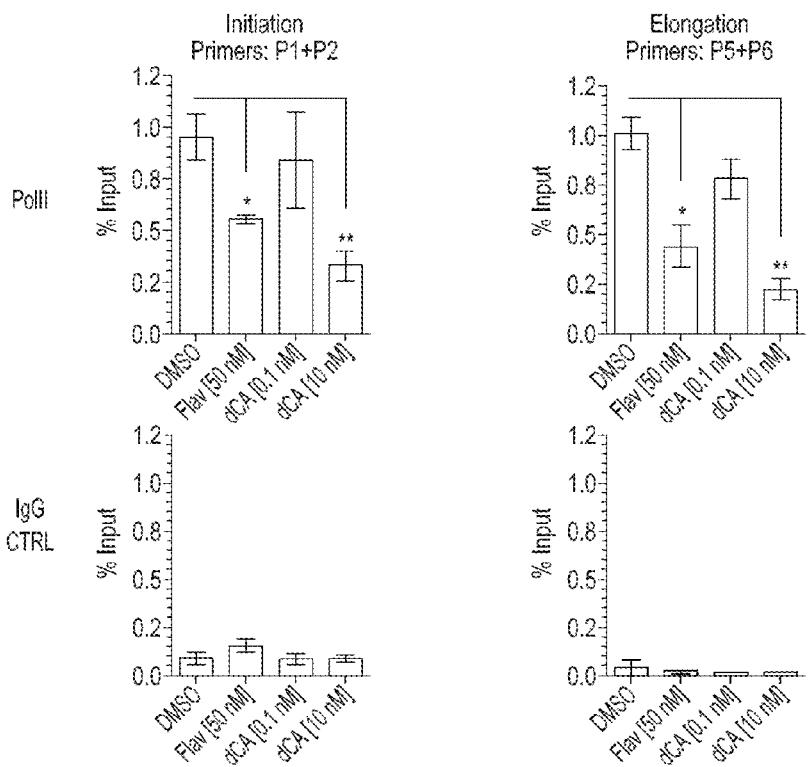
Figure 12:
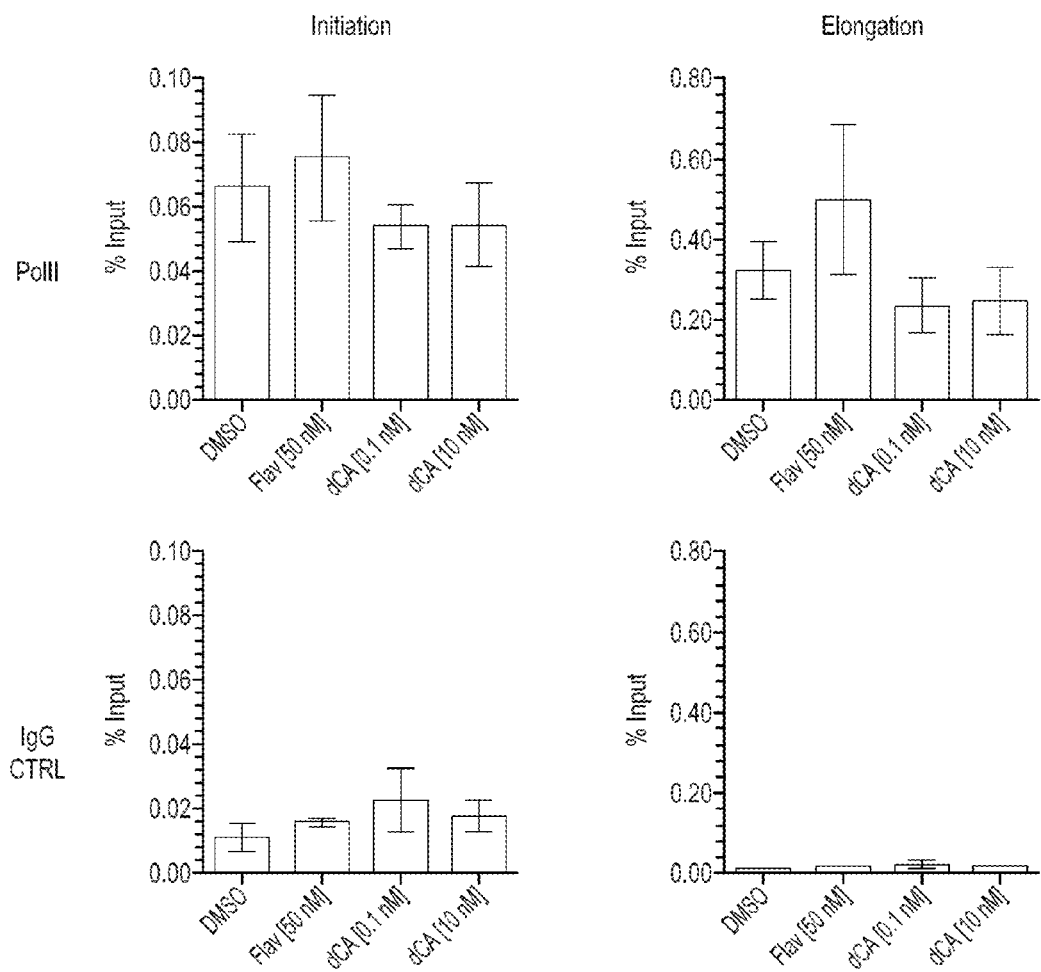
FIG. 12: ChIP assay of the GAPDH promoter and ORF. HeLa-CD4 cells chronically infected with pNL4-3 were treated with dCA for 4 days and Flavopiridol (Flav) for 6 h followed by protein-DNA crosslinking. Lysates were sonicated, the crosslinks were reversed and RNAPII was immunoprecipitated. DNA was measured by qPCR using primers specific for GAPDH promoter or ORF regions. ChIP values are represented as percentages of input. Error bars, ±s.d. (n=3).

Using chromatin immunoprecipitation (ChiP) with an anti-RNAPII antibody and qPCR, the effect of dCA on RNAPII occupancy of the 5'LTR promoter or viral ORF in HeLa-CD4 cells chronically infected with HIV-1 pNL43 was measured with the indicated primers (FIG. 3A). Association of RNAPII with the HIV promoter and ORF was significantly decreased in the presence of dCA, in a dose-dependent manner, while the occupancy of the GAPDH promoter and ORF was not affected (FIG. 3C and FIG. 12). Flavopiridol (Flav), a CDK9 inhibitor, was used as a positive control and DMSO served as negative control. These results provide evidence that dCA might block not only elongation but also initiation of transcription in chronically infected cells. As transcription is reduced and less Tat protein is made, the LTR promoter would tend to shut off with time, leading to reduced initiation. Furthermore, dCA might reduce Tat mediated recruitment of chromatin-remodeling proteins, such as the histone acetyltransferases (HATs) p300/CBP, to the promoter region. Together these results clearly show dCA's ability to inhibit RNAPII transcription from the HIV-1 provirus.

Figure 4A:
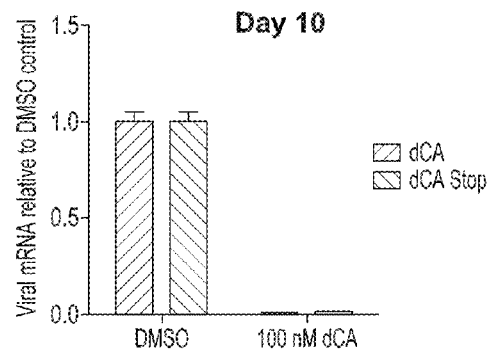
FIGS. 4A-4B: No viral rebound upon termination of dCA treatment.
Figure 4B:
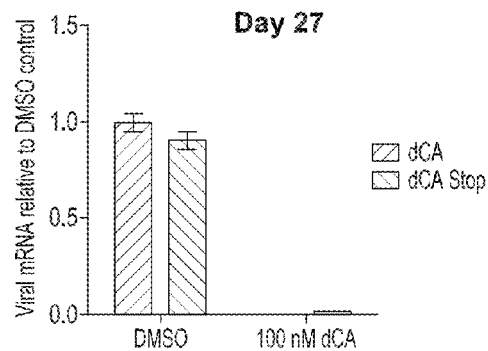

To determine whether virus production by cells treated with dCA rebounds after withdrawal of the drug, HeLa-CD4 cells chronically infected with pNL43 for 2 months were treated with dCA and viral RNA levels were measured by qRT-PCR at several time points after terminating treatment. No virus rebound was observed even 27 days after the treatment was stopped (FIGS. 4A, 4B), contrary to what is normally observed with ARVs. Overall, these provide evidence that dCA promotes rapid and permanent silencing of the HIV promoter, which may drastically limit the emergence of dCA-resistant viruses.

Potency and Scope of Didehydro-Cortistatin A Inhibition:

The potency of dCA inhibition was compared with that of nine compounds from four major ARVs (FIGS. 5A-5D). In a two-day acute infection assay with HeLa-CD4-LTR-LacZ cells, dCA exhibited a 1.5-3 log lower $EC_{50}$ than all other ARVs. Although dCA only reduces infectivity by 75-80% (versus 95-100% for the NNRTIs and INIs) this value is comparable to the NRTIs and is better than the PIs (~30%). PIs show low efficacy in this short 48 h assay as they act only upon spreading from the initial infection. Given that dCA blocks a post-integration event, this result is unsurpassing and it compares favorably with late acting compounds such as PIs. The results were similar when viral production was determined by RT-PCR of viral RNA in HeLa-CD4 cells infected and treated for four days with one compound from each class of inhibitors (FIG. 5E). Again, dCA consistently showed lower $EC_{50}$ values (<0.1 nM) with maximum inhibition around 80% while other ARVs showed complete inhibition, albeit with 100 fold or higher $EC_{50}$.

Figure 5A:
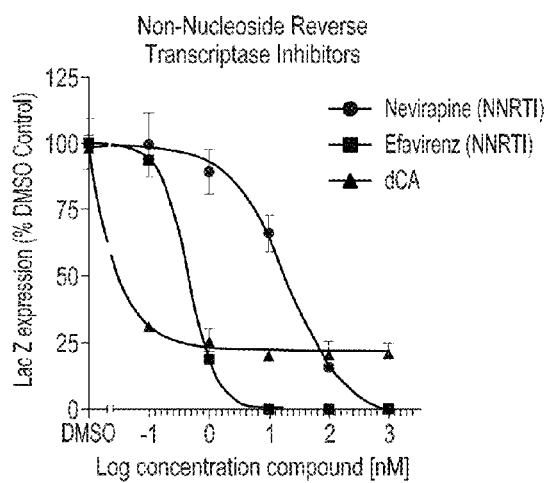
Figure 5B:
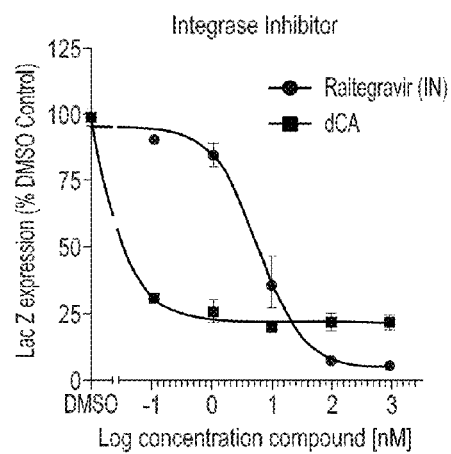
Figure 5F:
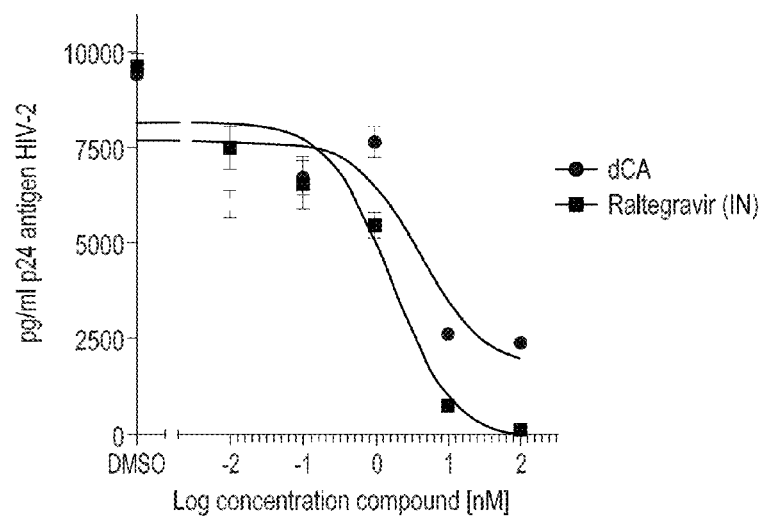
Figure 5G:
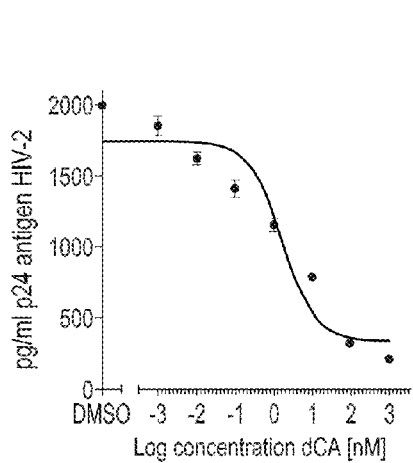

The susceptibility of HIV-2 to dCA inhibition was tested. dCA inhibited acute infection of HeLa-CD4 cells by HIV-2 (ROD/A) with an $EC_{50}$ of ≈5 nM (FIG. 5F), as well as chronic infection with an $EC_{50}$ of ≈1.7 nM (FIG. 5G), demonstrating the broad potential of dCA. Furthermore, dCA excluded equally well HIV-2 Tat protein from the nucleolus (FIGS. 11B, 11C). The slightly lower efficiency of dCA in blocking HIV-2 replication as compared to HIV-1 might be explained by the fact that unlike the HIV-1 TAR element, which contains a single stem-loop, the HIV-2 TAR element consists of 2 characteristic stem-loop structures, both of which participate in optimal Tat response.

Figure 5H:
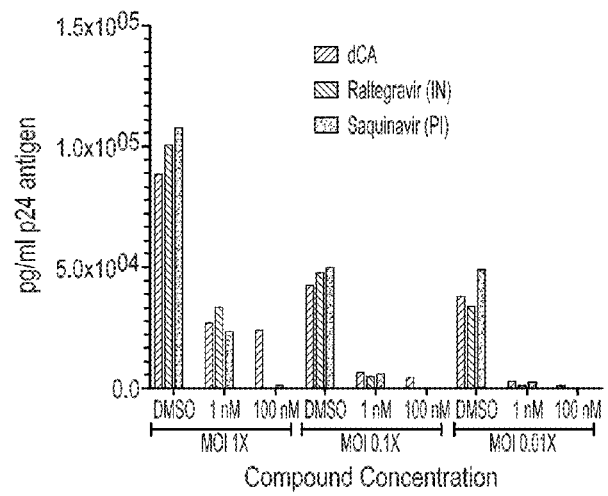
Figure 5I:
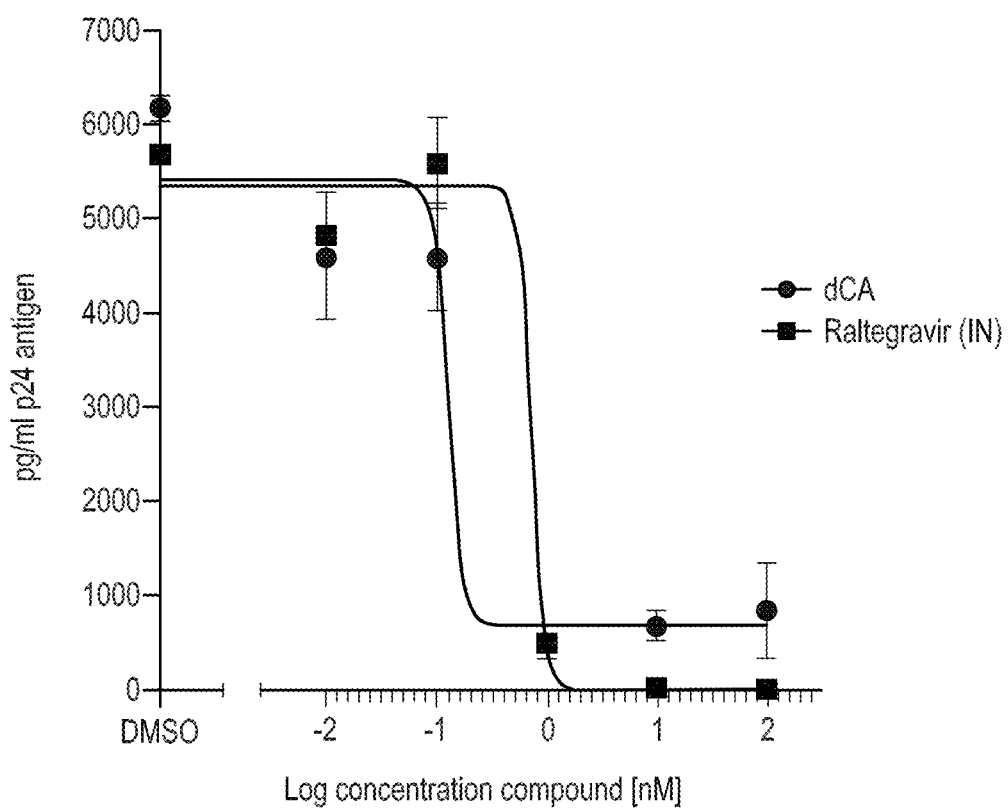
Figure 13A:
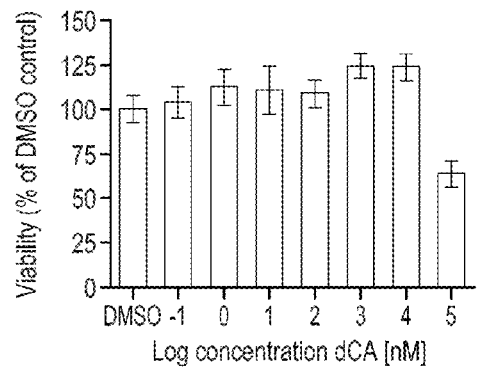
FIGS. 13A-13B: Effect of dCA on cell viability.
Figure 13B:
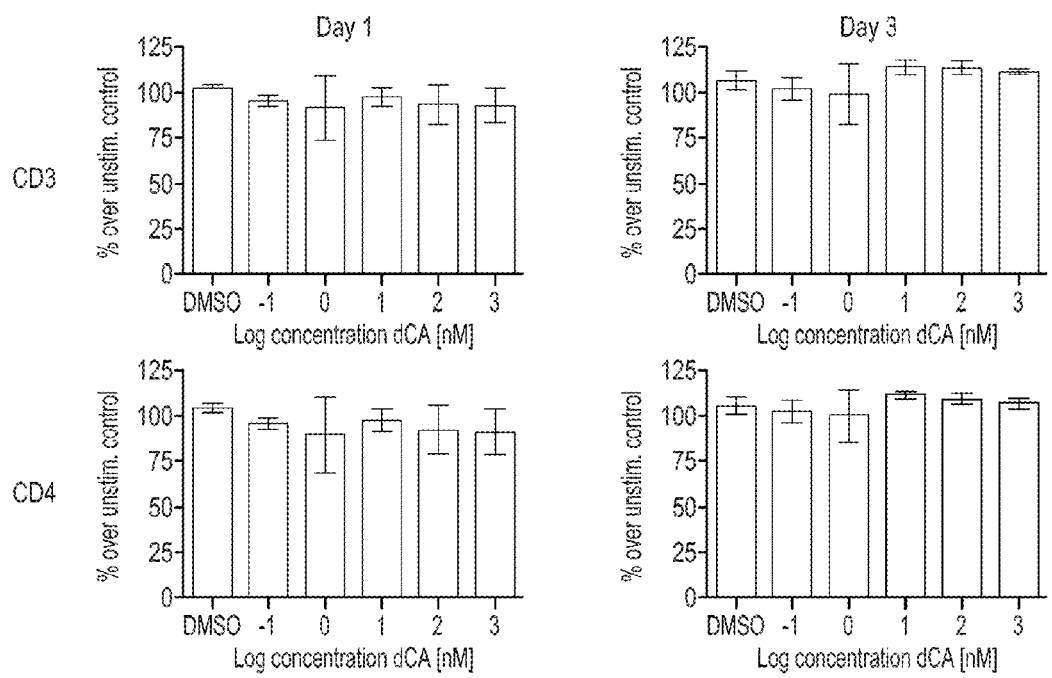

Didehydro-Cortistatin A Inhibits HIV Replication in Primary Cells from Uninfected and Infected Subjects at Different Disease Stages:

The ability of dCA to inhibit HIV-1 replication was measured in freshly isolated uninfected human peripheral blood mononuclear cells (PBMCs) stimulated with mitogen phytohaemagglutinin (PHA) and interleukin 2 (IL-2). PBMCs were infected with pNL43 and treated with raltegravir, saquinavir or dCA, and viral replication measured by p24 ELISA. dCA inhibited replication with an $EC_{50}$ of <1 nM (FIGS. 5H, 5I) in primary cells similar to that obtained with raltegravir and saquinavir, however a maximum inhibition plateau of 86% was observed for dCA. dCA treatment of primary cells did not affect cell viability, as the $CC_{50}$ values was 100 μM, which is higher than what was observed for Hela-CD4 cells (FIGS. 13A, 13B). HIV-1 transcription is intimately linked to T-cell activation due to shared motifs between the HIV-LTR and the regulatory regions in induced genes, namely NF-κB. A large variety of T cell stimuli activate NF-κB, including PHA, IL-2 and tumor necrosis factor alpha (TNF-α). In the absence of Tat-independent promoter activity, such as the activation mediated by NF-κB, dCA inhibition of HIV replication would be expected to be higher.

Figure 6A:
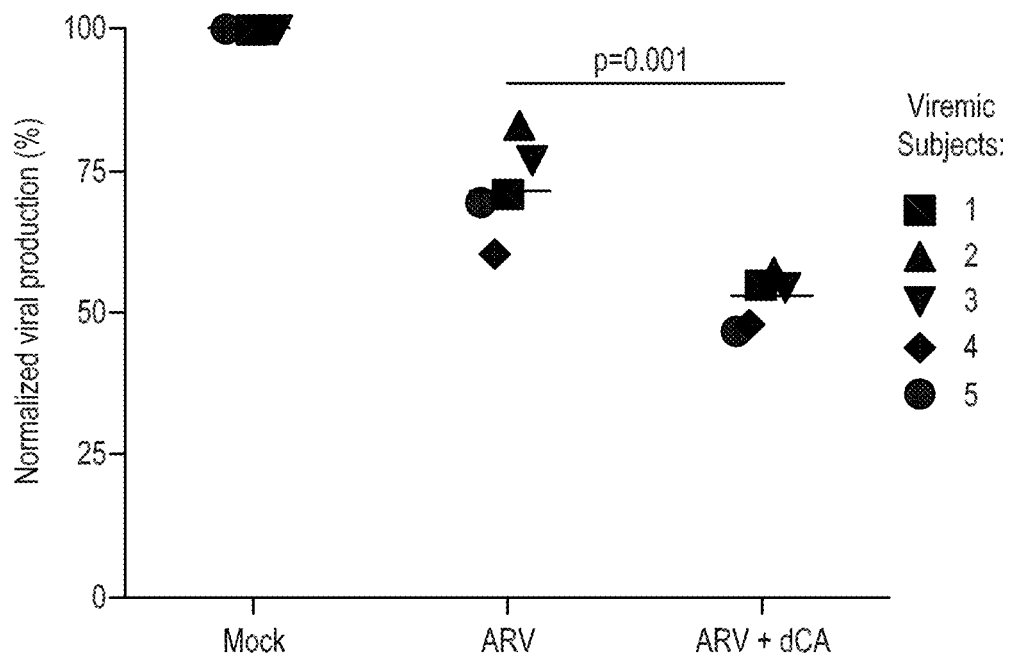
FIGS. 6A-6B: dCA activity on $CD4^+$ T cells from viremic and aviremic HIV-infected subjects.

The potency of dCA was further tested on spontaneous viral output (p24 production) from primary CD4+ T cells isolated from five viremic HIV-infected patients (FIG. 6A). Cells were grown in IL-2 to increase viability. With ARVs alone, which inhibit all new infections, decreased viral production by approximately 25% was observed, and addition of dCA to the ARVs further decreased p24 production by another 20%. dCA thus provides an important additive effect with other ARVs when added to primary CD4+ T cells from HIV-viremic subjects.

Figure 6B:
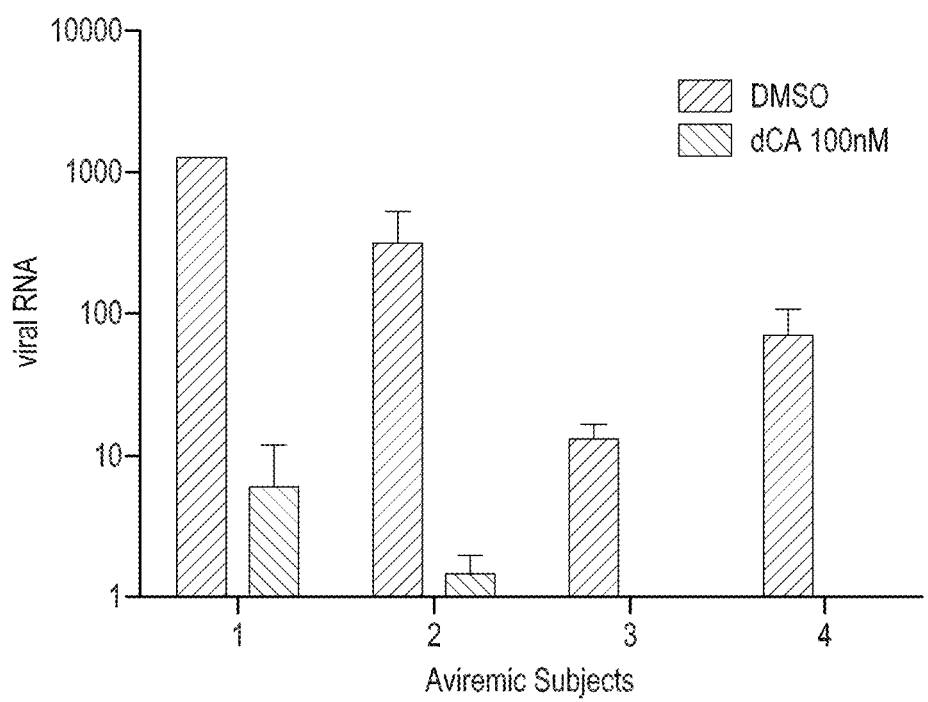

Also investigated was whether dCA could impact residual viremia from virally suppressed subjects (plasma viral load less than 50 copies/mL) receiving HAART. CD4'T cells were isolated from PBMCs of four subjects treated for at least 3 years who spontaneously released viral particles in vitro and grew them in the absence of IL-2. Using an ultrasensitive RT-PCR assay, in the presence of ARVs, a reduction of viral production of 99.7% at day 6 was observed (FIG. 6B). Importantly, dCA did not affect the viability of the cells at the concentrations used. Altogether, these results provide evidence that dCA is a highly potent inhibitor of the residual viral production from CD4+ T cells of virally suppressed subjects. These results also support the prediction that higher HIV-1 inhibition by dCA is observed in the absence of promoter activation by IL-2 (mediated by NF-κB), when replication is mostly dependent on Tat activity.

Didehydro-Cortistatin A Pharmacokinetics:

To evaluate the in vitro and in vivo stability of dCA an analytical LC-MS/MS method was developed (Table 1). In vitro studies compared murine and human hepatic microsomes (150 donor mixed male/female pool). Sunitinib, an FDA-approved kinase inhibitor with favorable human pharmacokinetics, was included as a positive control. dCA was resistant to hepatic oxidative metabolism in both human and mouse (Table 1A). Based on the encouraging microsomal data, follow-up mouse experiments were conducted to evaluate the ability to dose dCA via oral gavage (PO) and intraperitoneal injection (IP). dCA was easily formulated (1 mg/mL in water) due to its high aqueous solubility. C57B16 mice were dosed at 10 mg/kg and drug levels were quantitated in plasma at 1, 6, and 24 h by LC-MS/MS (Table 1B). The results impressively demonstrated that dCA can be given either IP or orally. Drug levels at 1 h after dosing were greater than 1000-fold the $EC_{50}$ value found in the cell-based assays. dCA concentration decreased at 6 and 24 h, but even 24 h post dose, plasma drug levels for all mice were above 30 nM (50-fold above the $EC_{50}$). Most importantly, mice were still healthy after 24 h dCA treatment.

TABLE 1A

Hepatic microsomal stability evaluated by incubating 1 μM with 0.2-1 mg/ml hepatic microsomes. The reaction is initiated by adding NADPH (1 mM). Aliquots are removed at 0, 5, 10, 20, 40 and 60 minutes. At the end of the assay, the samples are analyzed by LC-MS/MS. Data is log transformed and represented as half-life. Sutinib used for comparison.

| Compound ID | Species ($T_{1/2}$ in minutes) | |
|---|---|---|
| | Human | Mouse |
| dCA | 60 | 181 |
| Sunitinib | 77 | 28 |

TABLE 1A

Pharmacokinetics of CA assessed in C57Bl-6 mice. Drug levels measured by LC-MS/MS. A 3 mouse mini-PK assessment generating concentration vs. time profiles used to aid the design of pharmacology experiments. A sample formulations 1 mg/ml CA in water of 10 mg/kg dosed intravenously (IP) via the tail vein and orally by gavage (PO) with blood draws at 1, 6, and 24 hours.

| Time (hr) | Mouse | Plasma Concentration | |
|---|---|---|---|
| | | PO (μM) | IP (μM) |
| 1 | 1 | 0.95 | 2.19 |
| | 2 | 0.78 | 1.96 |
| | 3 | 0.84 | 3.19 |
| | Avg. | 0.85 | 2.45 |
| 6 | 1 | 0.34 | 0.52 |
| | 2 | 0.53 | 0.45 |
| | 3 | 0.71 | 0.9 |
| | Avg. | 0.52 | 0.63 |
| 24 | 1 | 0.03 | 0.04 |
| | 2 | 0.05 | 0.03 |
| | 3 | 0.06 | 0.06 |
| | Avg. | 0.05 | 0.04 |

Discussion

From the findings described herein, dCA is the most potent anti-Tat inhibitor described to date. It has exquisite binding selectivity for the basic domain of HIV Tat, a region also responsible for the Tat-TAR interaction. Importantly, dCA has a drug-like structure, is highly soluble in water, and displays good bioavailability in mice. dCA inhibits both HIV-1 and HIV-2 replication in tissue culture-adapted cells or in primary cells when used at single digit nanomolar concentrations, with no associated toxicity at the cellular level. Even though dCA alone fails to totally inhibit acute HIV infections, due to residual Tat-independent promoter activity, this feature is desirable as it limits off target effects from shared transcription factors binding cellular and viral promoters, such as NF-κB. Furthermore, dCA acts additively with other ARVs. HIV-1 lacking Tat undergoes some basal transcription, however does not sustain a spreading infection. Nonetheless, when chronically infected cells were grown in 100 nM dCA for longer periods of time, 99% of viral replication was inhibited.

dCA reduces both transcriptional initiation and elongation from the viral promoter, which is consistent with inhibiting the Tat-mediated conversion of hypophosphorylated RNA-PII to the hyperphosphorylated, processive form. Furthermore, termination of dCA treatment does not result in immediate virus rebound because the HIV promoter is transcriptionally silenced in the absence of Tat activity. This feature may also be extremely valuable at reducing the emergence of resistant HIV-1 strains.

Tat accumulates in the nucleolus via the basic region but whether its function in this compartment is relevant for pathogenesis is still debated. dCA excludes Tat from the nucleolus, most likely because its association with the Tat basic domain inhibits Tat-RNA interactions that most likely cause nucleolar accumulation. Whether dCA-mediated nucleolar Tat exclusion translates into any significant phenotypic outcome in HIV pathogenesis, other than its effect on transcriptional activity, remains to be addressed.

In an effort to understand the molecular basis of the only reported anti-proliferative and anti-migratory activity of CA against HUVECs, a high throughput kinome binding assay was performed. CA was reported to bind to CDK11

($K_d$=10±2 nM), CDK8 ($K_d$=17±2 nM), and ROCK II kinases ($K_d$=220±2 nM), however no inhibition of kinase activity was ever demonstrated. dCA binding to CDK11 was not confirmed. dCA did not inhibit the kinase activity of CDK11 in vitro nor did it bind to biotinylated dCA. Moreover, inhibition of CDK11 activity would be expected to be toxic, as CDK11 knockdown severely impairs cellular viability, and at the nanomolar concentrations of CA at which it was reported to interact with CDK11. Surprisingly, no toxicity was observed in this study.

Low levels of viral production persist in HIV-infected subjects taking HAART and are a major obstacle for complete eradication of the infection. dCA treatment was extremely successful at reducing viral production by a drastic 99.7% from primary $CD4^+$ T cells isolated from aviremic patients who had been under HAART treatment for a long period of time. Distinct from any currently available ARVs that prevent new rounds of infection, dCA inhibits HIV production from integrated proviral DNA, which by its mode of action may drastically reduce the low levels of persistent viremia observed in treated subjects. With a therapeutic index of over 8000, dCA defines a novel class of HIV anti-viral drugs endowed with the ability to decrease residual viremia during HAART and should be considered as a promising drug to be included in therapeutic eradication strategies.

Example 2: Identification of CA-Associated Cellular Proteins

Figure 14:
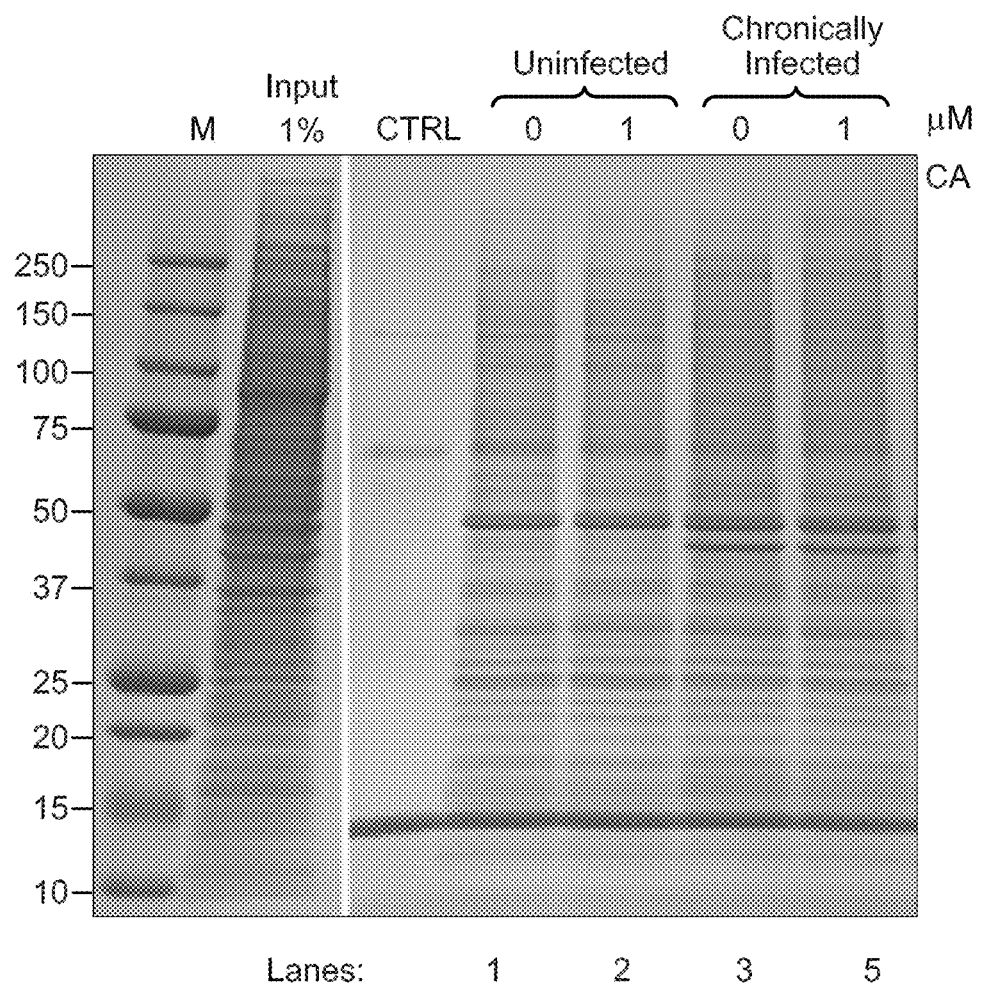
FIG. 14: Bio-CA associated proteins. Pull down assay using DYNABEADS® MYONE™ Streptavidin T1 coated with either biotin (CTRL) or Bio-CA from P42 cellular protein extract infected or not with pNL4-3 and treated or not with 1 μM CA 48 h. After SDS-PAGE analysis and Coomassie staining, gel slices were trypsin-digested and sent to mass spectrometry analysis.

To identify cellular proteins associated with CA, a biotinylated form of the compound (Bio-CA) was used. This derivative did not compromise the viability of the cells, and it showed a 10 fold higher $EC_{50}$ than CA, nevertheless at higher concentration it showed similar efficacy to CA. The Bio-CA was used to cover streptavidin-coated magnetic beads to pull down interacting proteins from either uninfected or chronically infected lysates of cells grown in the presence or absence of CA for 48 hours (FIG. 14D). The identity of the proteins pulled down under the different conditions was determined by HPLC MS/MS analysis. The proteins were identified with a greater than 95% confidence using a proprietary Scripps proteomics software package for protein identification, statistical analysis, and mass/peptide sequence correlation. The HIV proteome was added to the proteomics software search database before analysis. Many proteins were identified in uninfected untreated and in chronically untreated samples (approximately 300), however only 53 were displaced by more than 50% by the presence of CA. Of these 53 proteins, it appears that at least 2 may have a role in HIV-1 replication: DNA-dependent protein kinase catalytic subunit (DNA-PK) and helicase like transcription factor (HLTF).

CA Binds DNA-PK and Tat, but not a TAR-Nonbinding Mutant of Tat.

Figure 15:
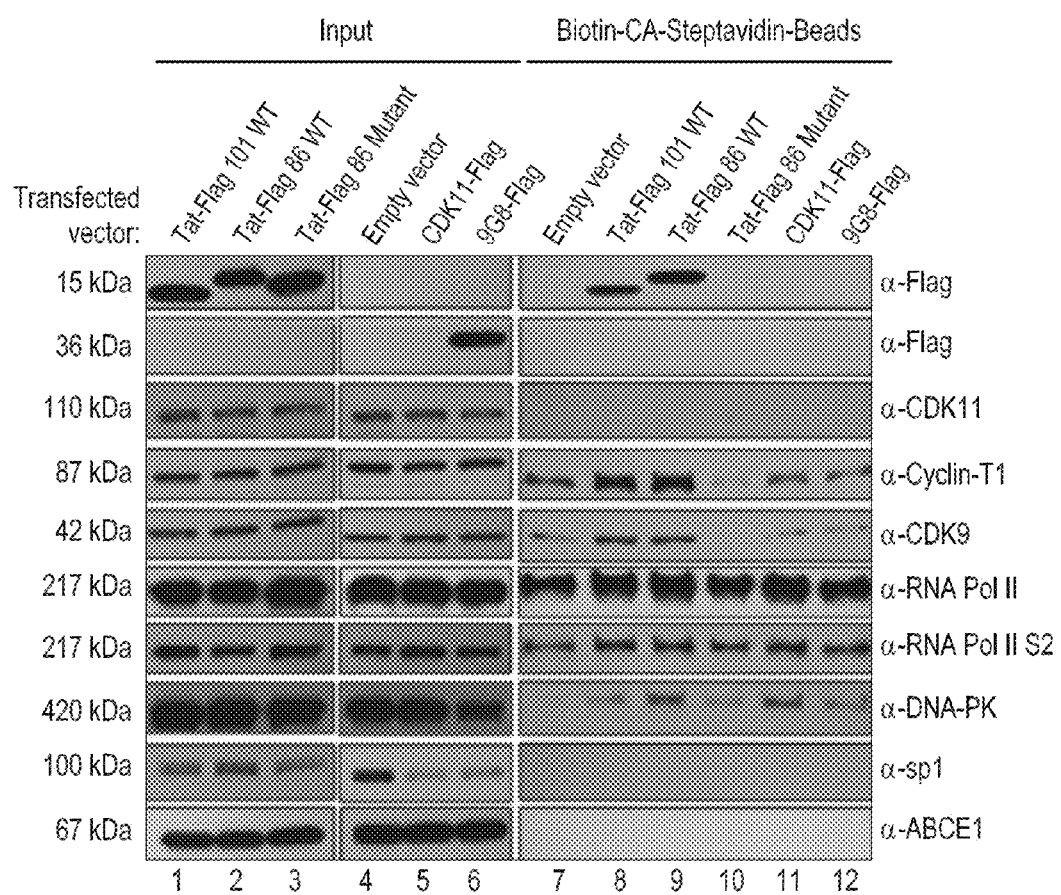
FIG. 15: CA binds Tat but not to TAR-nonbinding mutant of Tat. HEK293T cells were transfected with wt-Tat101-flag, vvtTat86-flag, Tat86mutant-TAR domain, CDK11-flag or 9G8-flag as negative control. Forty hours later, protein extracts were incubated with DYNABEADS® MYONE™ Streptavidin T1 coated with either biotin or Biotinylated-CA. Pulled down proteins analyzed by Western blot with the indicated antibodies.

Using Bio-CA coupled to magnetic streptavidin beads, it was shown that CA interacts with Tat-flag transfected into cells but not with a mutant of Tat that no longer binds TAR. CA did not interact with the RNA binding protein 9G8, ABCE1 protein (used as a negative control), nor with the CDK11, which had been previously reported to interact with CA in an in vitro kinome assay (Cee V J, et al., *Angew Chem Int Ed Engl.* 2009; 48(47):8952-7) (FIG. 15, first 3 rows). DNA-PK seems to interact with CA either in the presence or absence of Tat or Tat mutant (FIG. 15, 4th row). The P-TEFb complex, CDK9 and Cyclin T1, were also shown to interact with CA, and an increased association of these two proteins with CA in the presence of Tat was observed, and a corresponding decrease in the presence of the Tat mutant; these different binding affinities reflect a competition between CA and Tat mutant for P-TEFb binding, as the Tat mutant does not bind to TAR but it is still capable of binding to P-TEFb. CA was also shown to pull down RNA polymerase, which was expected, as P-TEFb and Tat associate with RNAPII; however an interaction between CA and Sp1 was not observed. All the associations between CA and the cellular proteins observed might be direct or indirect, and experiments using recombinant proteins are necessary to determine the nature of these interactions. Altogether, these results provide evidence that Tat-stimulated elongation from the HIV-1 promoter may be one of the mechanisms by which Cortistatin A prevents retroviral replication.

Assessment of Whether CA Inhibits DNA-PK Phosphorylation of Sp1.

DNA-PK was identified as a binding partner of CA by mass spectrometry and further confirmation of this interaction was provided by performing a pull down assay (FIG. 15). Without wishing to be bound by theory, it was hypothesized that part of the mechanism by which CA inhibits HIV replication is by blocking the accrued DNA-PK phosphorylation of Sp1 mediated by Tat with a consequent reduction in both basal and Tat-mediated transcriptional activation of the HIV LTR promoter. Sp1 is thought to be essential for basal transcription and Tat-mediated activation of HIV-1. This is concordant with the fact that Sp1 is upregulated in activated T cells, which compose the primary reservoir for HIV-1 replication. The data so far provides evidence that CA reduces the transcription activity from CMV and MLV promoters. These results indicate that CA acts in a Tat-independent fashion on CMV and MLV promoters, and one possible explanation would be a reduction in Sp1 activity on these promoters (CMV has 11 Sp1 binding sites).

Example 3: Modulation of Neurotoxicity

One of the more notable early events in HIV infection is how rapidly the virus is detected in the central nervous system (CNS). This may result in a variety of clinical abnormalities, including HIV-associated encephalitis (HIVE) and dementia (HAD), which occur in approximately 10-15% of patients chronically infected in the United States (A. V. Albright, et al., *J. Neurovirol.* 9 (2) (2003) 222-227; J. C. McArthur, et al., *Lancet Neurol.* 4 (9) (2005) 543-555). Despite the initial drop in the incidence of cognitive impairment as a result of highly active antiretroviral therapy (HAART), CNS disease is again increasing as HIV-infected individuals are living longer.

In the brain, macrophages/microglia are the primary cells infected by HIV, and these cells can support viral replication. A small percentage of astrocytes can also be infected, but HIV entry (B. Schweighardt, et al., *AIDS Res. Hum, Retroviruses,* 17 (12) (2001) 1133-1142) and replication (C. L. Ong, et al., *J Virol.* 79 (20) (2005) 12763-12772) are inefficient. The contribution of infected astrocytes to CNS disease is not well defined. There is no evidence that neurons are infected with the virus; however, neuronal damage and dropout occur, indicating that neuronal cell death must be the result of indirect mechanisms, such as neurotoxins released by HIV-infected and uninfected cells. One such neurotoxin released by infected cells is the transactivator of the virus, HIV Tat.

HIV Tat, a virally encoded protein that promotes replication, can be released by HIV-infected cells to the extracellular space, cerebrospinal fluid (CSF) and sera. Tat has been detected in the brains of people with HIVE by mRNA and Western blotting analyses (L. Hudson, et al., J. Neurovirol. 6 (2) (2000) 145-155; C. A. Wiley, et al., AIDS 10 (8)(1996) 843-847). It is unclear whether the majority of the detected tat is released by infected cells within the CNS or is specifically transported across the blood-brain barrier (BBB) from the sera, but either way tat is taken up by CNS cells with toxic consequences often resulting in apoptosis, particularly in neurons.

Tat is an 86- to 104-amino-acid viral protein that activates human immunodeficiency virus type 1 expression, modifies several cellular functions, and causes neurotoxicity. Here, the extent was determined as to which peptide fragments of human immunodeficiency virus type 1 BRU $Tat_{1-86}$, produced neurotoxicity, increased levels of intracellular calcium ($[Ca^{2+}]i$), and affected neuronal excitability. $Tat_{31-61}$ but not $Tat_{48-85}$ dose dependently increased cytotoxicity and levels of $[Ca^{2+}]i$ in cultured human fetal brain cells. Similarly, $Tat_{31-61}$ but not $Tat_{48-85}$ depolarized rat hippocampal CA1 neurons in slices of rat brain. The neurotoxicity and increases in $[Ca^{2+}]i$ could be significantly inhibited by non-N-methyl-D-aspartate excitatory amino acid receptor antagonists.

Shorter 15-mer peptides which overlapped by 10 amino acids each and which represented the entire sequence of $Tat_{1-86}$ failed to produce any measurable neurotoxicity. Although it remains to be determined if Tat acts directly on neurons and/or indirectly via glial cells, these findings do provide evidence that Tat neurotoxicity is conformationally dependent, that the active site resides within the first exon of Tat between residues 31 to 61, and that these effects are mediated at least in part by excitatory amino acid receptors.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the Disclosure is provided to allow the reader to quickly ascertain the nature of the technical disclosure. It is submitted with the understanding that it will not be used to interpret or limit the scope or meaning of the following claims.

What is claimed is:

1. A method of treating a retroviral infection in a patient, comprising:

administering to the patient a therapeutically effective amount of an inhibitor of retroviral transcription wherein the inhibitor inhibits retroviral transcription as compared to a control; and, thereby treating a retroviral infection in the patient, wherein the inhibitor of retroviral transcription comprises didehydro cortistatin A; cortistatin A; a compound shown in formula XII wherein the circled X is 7-isoquinoline, R1 and R5 are independently hydrogen or alkyl; or a compound shown in formula XIII, wherein the circled X is 7-isoquinoline, R1 and R5 are independently hydrogen or alkyl, and the carbon attached to by the circled X has a stereochemistry of S (3S):

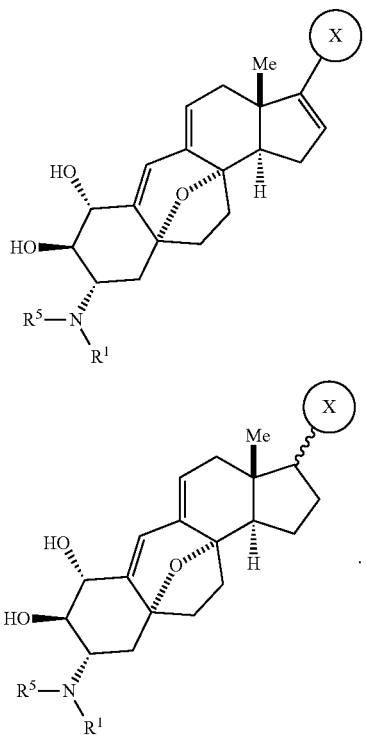

XII

XIII

2. The method of claim 1, wherein the retroviral viral infection is a lentivirus.

3. The method of claim 2, wherein the lentivirus is a human immunodeficiency virus (HIV).

4. The method of claim 1, wherein the inhibitor of retroviral transcription inhibits function or activity of a Trans-Activator of Transcription (Tat), a molecule associated with Trans-Activator of Transcription (Tat), a molecule associated with Transactivation Responsive element (TAR) a Transactivation Responsive element (TAR) and/or interaction between a Trans-Activator of Transcription (Tat) and a Transactivation Responsive element (TAR), DNA-PK or combinations thereof.

5. The method of claim 1, wherein the inhibitor of retroviral transcription comprises a cortistatin agent having a general structure of Formula XII:

Formula XII

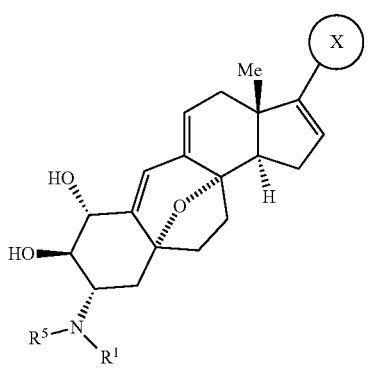

XII

Wherein: X is 7-isoquinoline, R1 and R5 are independently hydrogen or alkyl.

6. The method of claim 1, wherein the inhibitor of retroviral transcription comprises a cortistatin agent having a general structure of Formula XIII:

Formula XIII

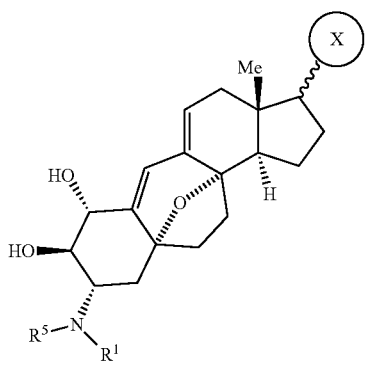

XIII

Wherein: the circled X is 7-isoquinoline, R1 and R5 are independently hydrogen or alkyl, and the carbon attached to by the circled X has a stereochemistry of S (3S).

7. The method of claim of claim 1, wherein the inhibitor of retroviral transcription is a didehydro-cortistatin A (dCA).

8. The method of claim 1, further comprising administering to a patient a therapeutically effective amount of one or more anti-retroviral drugs.

9. A method of inhibiting retroviral production in vitro or in vivo comprising: contacting a cell or administering to a patient an effective amount of an inhibitor of retroviral replication; and modulating retroviral replication in vitro or in vivo, wherein the inhibitor of retroviral transcription comprises didehydro cortistatin A; cortistatin A; a compound shown in formula XII wherein the circle X is 7-isoquinoline, R1 and R5 are independently hydrogen or alkyl; or a compound shown in formula XIII, wherein circle X is 7-isoquinoline, R1 and R5 are independently hydrogen or alkyl, and the carbon attached to by the circle X has a stereochemistry of S (3S):

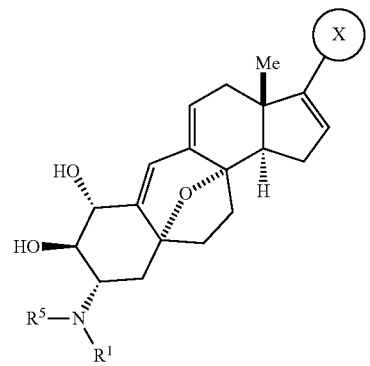

XII

XIII

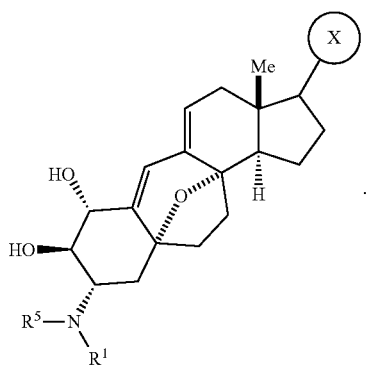

10. The method of claim 9, wherein the retrovirus is a human immunodeficiency virus (HIV).

11. The method of claim 9, wherein the inhibitor of retroviral transcription inhibits function or activity of a Trans-Activator of Transcription (Tat), a molecule associated with Trans-Activator of Transcription (Tat), a molecule associated with Transactivation Responsive element (TAR) a Transactivation Responsive element (TAR) and/or interaction between a Trans-Activator of Transcription (Tat) and a Transactivation Responsive element (TAR), DNA-PK or combinations thereof.

12. The method of claim 9, optionally comprising contacting a cell or administering to a patient infected with a retrovirus a therapeutically effective amount of one or more anti-retroviral drugs.

13. The method of claim of claim 9, wherein the inhibitor of retroviral transcription is a didehydro-cortistatin A (dCA).

14. A method of treating neurotoxicity in a patient infected with a retrovirus, comprising:
administering to the patient a therapeutically effective amount of an agent which modulates function or activity of a Trans-Activator of Transcription (Tat), a molecule associated with Trans-Activator of Transcription (Tat), a molecule associated with Transactivation Responsive element (TAR) a Transactivation Responsive element (TAR) and/or interaction between a Trans-Activator of Transcription (Tat) and a Transactivation Responsive element (TAR), or DNA-PK; and
treating neurotoxicity in a patient infected with a retrovirus, wherein the agent comprises didehydro cortistatin A; cortistatin A; a compound shown in formula XII wherein the circled X is 7-isoquinoline, R1 and R5 are independently hydrogen or alkyl; or a compound shown in formula XIII, wherein the circled X is 7-isoquinoline, R1 and R5 are independently hydrogen or alkyl, and the carbon attached to by the circled X has a stereochemistry of S (3S):

XII

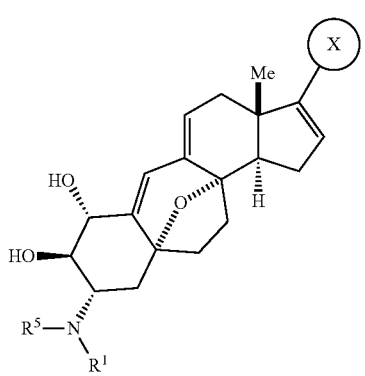

XIII

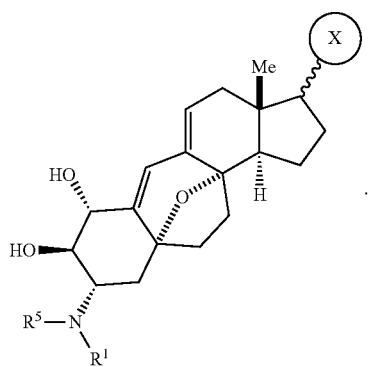

* * * * *